US008900316B2

(12) United States Patent
Lenz et al.

(10) Patent No.: US 8,900,316 B2
(45) Date of Patent: Dec. 2, 2014

(54) CRUCIATE-RETAINING KNEE PROSTHESIS

(75) Inventors: Nathaniel M. Lenz, Southaven, MS (US); Richard Michael Smith, Memphis, TN (US); Zachary Christopher Wilkinson, Germantown, TN (US); Brian W. McKinnon, Bartlett, TN (US); Abraham B. Salehi, Bartlett, TN (US); Jonathan Kirk Nielsen, Dana Point, CA (US); Michael D. Ries, Tiburton, CA (US); Gerald J. Jerry, St. Clair, MI (US)

(73) Assignee: Smith & Nephew, Inc., Memphis, TN (US)

( * ) Notice: Subject to any disclaimer, the term of this patent is extended or adjusted under 35 U.S.C. 154(b) by 305 days.

(21) Appl. No.: 13/016,175

(22) Filed: Jan. 28, 2011

(65) Prior Publication Data

US 2011/0190898 A1 Aug. 4, 2011

Related U.S. Application Data

(60) Provisional application No. 61/372,556, filed on Aug. 11, 2010, provisional application No. 61/382,287, filed on Sep. 13, 2010, provisional application No. 61/299,835, filed on Jan. 29, 2010.

(51) Int. Cl.
*A61F 2/38* (2006.01)
*A61F 2/30* (2006.01)

(52) U.S. Cl.
CPC ............ *A61F 2/38* (2013.01); *A61F 2/3859* (2013.01); *A61F 2/389* (2013.01); *A61F 2002/30616* (2013.01); *A61F 2002/30884* (2013.01); *A61F 2002/3895* (2013.01)

USPC ............... 623/20.32; 623/20.14; 623/20.15; 623/20.21; 623/20.38; 623/20.31; 623/20.33; 623/20.34

(58) Field of Classification Search
USPC ............................... 623/20.32–20.34
See application file for complete search history.

(56) References Cited

U.S. PATENT DOCUMENTS 3,748,662 A 7/1973 Helfet
3,774,244 A 11/1973 Walker
(Continued)

FOREIGN PATENT DOCUMENTS

CN 101450014 6/2009
DE 10220591 12/2003
(Continued)

OTHER PUBLICATIONS

International Search Report and Written Opinion for International Application No. PCT/US2011/022922, mailed Oct. 24, 2011, 10 pages.

(Continued)

*Primary Examiner* — David Isabella
*Assistant Examiner* — Jacqueline Woznicki
(74) *Attorney, Agent, or Firm* — Fish & Richardson P.C.

(57) ABSTRACT

Certain embodiments generally provide an improved tibial base member comprising keel portions that allow one or both cruciate ligaments to be preserved. Other embodiments provide improved lateral and/or medial inserts having a mesial lip that helps relieve and/or prevent impingement between the femoral component and the tibial eminence. Other embodiments provide improved femoral components having various chamfers to provide additional clearance with respect to the tibial eminence and posterior cruciate ligament without decreasing bone coverage.

45 Claims, 73 Drawing Sheets

(56) References Cited

U.S. PATENT DOCUMENTS

| | | | |
|---|---|---|---|
| 3,869,731 A | 3/1975 | Waugh et al. | |
| 3,924,277 A | 12/1975 | Freeman et al. | |
| 4,178,641 A | 12/1979 | Grundei et al. | |
| 4,249,270 A | 2/1981 | Bahler et al. | |
| 4,353,135 A | 10/1982 | Forte et al. | |
| 4,659,331 A | 4/1987 | Matthews et al. | |
| 4,714,472 A | 12/1987 | Averill et al. | |
| 4,714,473 A | 12/1987 | Bloebaum | |
| 4,731,086 A | 3/1988 | Whiteside et al. | |
| 4,936,853 A | 6/1990 | Fabian et al. | |
| 4,944,760 A | 7/1990 | Kenna | |
| 4,963,152 A * | 10/1990 | Hofmann et al. | 623/20.31 |
| 5,002,545 A | 3/1991 | Whiteside et al. | |
| 5,037,423 A | 8/1991 | Kenna | |
| 5,137,536 A | 8/1992 | Koshino | |
| 5,271,747 A | 12/1993 | Wagner et al. | |
| 5,282,870 A | 2/1994 | Moser et al. | |
| 5,314,483 A | 5/1994 | Wehrli et al. | |
| 5,326,358 A | 7/1994 | Aubriot et al. | |
| 5,330,533 A | 7/1994 | Walker | |
| 5,356,414 A | 10/1994 | Cohen et al. | |
| 5,358,527 A | 10/1994 | Forte | |
| 5,387,240 A | 2/1995 | Pottenger et al. | |
| 5,405,398 A | 4/1995 | Buford, III et al. | |
| 5,480,446 A | 1/1996 | Goodfellow et al. | |
| 5,514,139 A | 5/1996 | Goldstein et al. | |
| 5,549,684 A | 8/1996 | Amino et al. | |
| 5,549,686 A | 8/1996 | Johnson et al. | |
| 5,571,194 A | 11/1996 | Gabriel | |
| 5,597,379 A | 1/1997 | Haines et al. | |
| 5,609,639 A | 3/1997 | Walker | |
| 5,643,272 A | 7/1997 | Haines et al. | |
| 5,658,342 A | 8/1997 | Draganich et al. | |
| 5,658,344 A | 8/1997 | Hurlburt | |
| 5,669,914 A | 9/1997 | Eckhoff | |
| 5,683,397 A | 11/1997 | Vendrely et al. | |
| 5,702,458 A | 12/1997 | Burstein et al. | |
| 5,702,464 A | 12/1997 | Lackey et al. | |
| 5,702,466 A | 12/1997 | Pappas et al. | |
| 5,755,800 A | 5/1998 | O'Neil et al. | |
| 5,755,801 A | 5/1998 | Walker et al. | |
| 5,755,803 A | 5/1998 | Haines et al. | |
| 5,768,134 A | 6/1998 | Swaelens et al. | |
| 5,782,921 A | 7/1998 | Colleran et al. | |
| 5,810,827 A | 9/1998 | Haines et al. | |
| 5,879,354 A | 3/1999 | Haines et al. | |
| 5,879,392 A | 3/1999 | McMinn | |
| 5,908,424 A | 6/1999 | Bertin et al. | |
| 5,928,285 A | 7/1999 | Bigliani et al. | |
| 5,964,808 A | 10/1999 | Blaha et al. | |
| 6,013,103 A | 1/2000 | Kaufman et al. | |
| 6,056,754 A | 5/2000 | Haines et al. | |
| 6,080,195 A | 6/2000 | Colleran et al. | |
| 6,090,144 A | 7/2000 | Letot et al. | |
| 6,126,692 A | 10/2000 | Robie et al. | |
| 6,152,960 A | 11/2000 | Pappas | |
| 6,162,254 A | 12/2000 | Timoteo | |
| 6,165,223 A | 12/2000 | Metzger et al. | |
| 6,190,415 B1 | 2/2001 | Cooke et al. | |
| 6,197,064 B1 | 3/2001 | Haines et al. | |
| 6,280,476 B1 | 8/2001 | Metzger et al. | |
| 6,299,646 B1 | 10/2001 | Chambat et al. | |
| 6,306,172 B1 | 10/2001 | O'Neil et al. | |
| 6,342,075 B1 | 1/2002 | MacArthur | |
| 6,361,564 B1 | 3/2002 | Marceaux et al. | |
| 6,379,388 B1 | 4/2002 | Ensign et al. | |
| 6,406,497 B2 | 6/2002 | Takei | |
| 6,413,279 B1 | 7/2002 | Metzger et al. | |
| 6,428,577 B1 | 8/2002 | Evans et al. | |
| 6,458,160 B2 | 10/2002 | Biegun et al. | |
| 6,482,209 B1 | 11/2002 | Engh et al. | |
| 6,500,208 B1 | 12/2002 | Metzger et al. | |
| 6,506,215 B1 | 1/2003 | Letot et al. | |
| 6,558,426 B1 | 5/2003 | Masini | |
| 6,582,469 B1 | 6/2003 | Tornier | |
| 6,620,198 B2 | 9/2003 | Burstein et al. | |
| 6,623,526 B1 | 9/2003 | Lloyd | |
| 6,695,848 B2 | 2/2004 | Haines | |
| 6,709,461 B2 | 3/2004 | O'Neil et al. | |
| 6,712,856 B1 | 3/2004 | Carignan et al. | |
| 6,723,102 B2 | 4/2004 | Johnson et al. | |
| 6,755,864 B2 | 6/2004 | Brack et al. | |
| 6,764,516 B2 | 7/2004 | Pappas | |
| 6,770,077 B2 | 8/2004 | Van Zile et al. | |
| 6,783,550 B2 | 8/2004 | MacArthur | |
| 6,905,513 B1 | 6/2005 | Metzger | |
| 6,905,514 B2 | 6/2005 | Carignan et al. | |
| 6,916,340 B2 | 7/2005 | Metzger et al. | |
| 6,916,341 B2 | 7/2005 | Rolston | |
| 6,972,039 B2 | 12/2005 | Metzger et al. | |
| 6,986,791 B1 | 1/2006 | Metzger | |
| 7,037,341 B2 | 5/2006 | Nowakowski | |
| 7,060,101 B2 | 6/2006 | O'Connor et al. | |
| 7,070,622 B1 | 7/2006 | Brown et al. | |
| 7,081,137 B1 | 7/2006 | Servidio | |
| 7,094,259 B2 | 8/2006 | Tarabichi | |
| 7,101,401 B2 | 9/2006 | Brack | |
| 7,104,996 B2 | 9/2006 | Bonutti | |
| 7,105,027 B2 | 9/2006 | Lipman et al. | |
| 7,115,131 B2 | 10/2006 | Engh et al. | |
| 7,175,664 B1 | 2/2007 | Lakin | |
| 7,255,715 B2 | 8/2007 | Metzger | |
| 7,261,740 B2 | 8/2007 | Tuttle et al. | |
| 7,297,165 B1 | 11/2007 | Kriek | |
| 7,326,252 B2 | 2/2008 | Otto et al. | |
| 7,344,541 B2 | 3/2008 | Haines et al. | |
| 7,371,240 B2 | 5/2008 | Pinczewski et al. | |
| 7,387,644 B2 | 6/2008 | Beynnon et al. | |
| 7,422,605 B2 | 9/2008 | Burstein et al. | |
| 7,517,365 B2 | 4/2009 | Carignan et al. | |
| 7,520,901 B2 | 4/2009 | Engh et al. | |
| 7,559,928 B2 | 7/2009 | Johnson et al. | |
| 7,591,854 B2 | 9/2009 | Wasielewski | |
| 7,604,637 B2 | 10/2009 | Johnson et al. | |
| 7,615,054 B1 | 11/2009 | Bonutti | |
| 7,632,283 B2 | 12/2009 | Heldreth | |
| 7,686,812 B2 | 3/2010 | Axelson, Jr. et al. | |
| 7,695,520 B2 | 4/2010 | Metzger et al. | |
| 7,708,782 B2 | 5/2010 | Burstein et al. | |
| 7,758,652 B2 | 7/2010 | Engh et al. | |
| 7,780,672 B2 | 8/2010 | Metzger et al. | |
| 7,850,698 B2 | 12/2010 | Straszheim-Morley et al. | |
| 7,896,922 B2 | 3/2011 | Engh et al. | |
| 8,568,486 B2 * | 10/2013 | Wentorf et al. | 623/20.32 |
| 8,574,304 B2 * | 11/2013 | Wentorf et al. | 623/20.32 |
| 8,591,594 B2 * | 11/2013 | Parisi et al. | 623/20.32 |
| 8,613,775 B2 * | 12/2013 | Wentorf et al. | 623/20.32 |
| 8,758,444 B2 * | 6/2014 | Wentorf et al. | 623/20.32 |
| 2001/0014827 A1 | 8/2001 | Chambat et al. | |
| 2001/0018615 A1 | 8/2001 | Biegun et al. | |
| 2002/0010512 A1 | 1/2002 | Takei | |
| 2002/0029038 A1 | 3/2002 | Haines | |
| 2002/0058997 A1 | 5/2002 | O'Connor et al. | |
| 2002/0072802 A1 | 6/2002 | O'Neil et al. | |
| 2002/0099446 A1 | 7/2002 | MacArthur | |
| 2002/0161447 A1 | 10/2002 | Salehi et al. | |
| 2002/0173797 A1 | 11/2002 | Van Zile et al. | |
| 2002/0193797 A1 | 12/2002 | Johnson et al. | |
| 2002/0198528 A1 | 12/2002 | Engh et al. | |
| 2003/0009232 A1 | 1/2003 | Metzger et al. | |
| 2003/0028196 A1 | 2/2003 | Bonutti | |
| 2003/0033018 A1 | 2/2003 | Merchant | |
| 2003/0093156 A1 | 5/2003 | Metzger et al. | |
| 2003/0153980 A1 | 8/2003 | Brack | |
| 2003/0158606 A1 | 8/2003 | Coon et al. | |
| 2003/0199985 A1 | 10/2003 | Masini | |
| 2003/0236523 A1 | 12/2003 | Johnson et al. | |
| 2004/0006393 A1 | 1/2004 | Burkinshaw | |
| 2004/0044414 A1 | 3/2004 | Nowakowski | |
| 2004/0064073 A1 | 4/2004 | Heldreth | |
| 2004/0064191 A1 | 4/2004 | Wasielewski | |
| 2004/0098133 A1 | 5/2004 | Carignan et al. | |
| 2004/0138755 A1 | 7/2004 | O'Connor et al. | |
| 2004/0162619 A1 | 8/2004 | Blaylock et al. | |

(56) References Cited

U.S. PATENT DOCUMENTS

| | | |
|---|---|---|
| 2004/0167630 A1 | 8/2004 | Rolston |
| 2004/0204760 A1 | 10/2004 | Fitz et al. |
| 2005/0021147 A1 | 1/2005 | Tarabichi |
| 2005/0027365 A1* | 2/2005 | Burstein et al. ............ 623/20.32 |
| 2005/0033424 A1 | 2/2005 | Fell |
| 2005/0055028 A1 | 3/2005 | Haines |
| 2005/0096747 A1 | 5/2005 | Tuttle et al. |
| 2005/0101966 A1 | 5/2005 | Lavallee |
| 2005/0102032 A1 | 5/2005 | Beynnon et al. |
| 2005/0119661 A1 | 6/2005 | Hodgson et al. |
| 2005/0119664 A1 | 6/2005 | Carignan et al. |
| 2005/0149038 A1 | 7/2005 | Haines et al. |
| 2005/0149039 A1 | 7/2005 | Haines et al. |
| 2005/0149040 A1 | 7/2005 | Haines et al. |
| 2005/0165491 A1 | 7/2005 | Diaz |
| 2005/0171545 A1 | 8/2005 | Walsh et al. |
| 2005/0171612 A1 | 8/2005 | Rolston |
| 2005/0187635 A1 | 8/2005 | Metzger |
| 2005/0209702 A1 | 9/2005 | Todd et al. |
| 2005/0246027 A1 | 11/2005 | Metzger et al. |
| 2005/0283250 A1 | 12/2005 | Coon et al. |
| 2005/0283251 A1 | 12/2005 | Coon et al. |
| 2005/0283252 A1 | 12/2005 | Coon et al. |
| 2005/0283253 A1 | 12/2005 | Coon et al. |
| 2006/0004460 A1 | 1/2006 | Engh et al. |
| 2006/0015185 A1 | 1/2006 | Chambat et al. |
| 2006/0178749 A1 | 8/2006 | Pendleton et al. |
| 2006/0184176 A1 | 8/2006 | Straszheim-Morley et al. |
| 2006/0189998 A1 | 8/2006 | Rasmussen |
| 2006/0190087 A1 | 8/2006 | O'Connor et al. |
| 2006/0195195 A1 | 8/2006 | Burstein et al. |
| 2006/0200158 A1 | 9/2006 | Farling et al. |
| 2006/0200162 A1 | 9/2006 | Farling et al. |
| 2006/0212124 A1 | 9/2006 | Siebel |
| 2007/0010884 A1 | 1/2007 | Tuke |
| 2007/0078517 A1 | 4/2007 | Engh et al. |
| 2007/0173848 A1 | 7/2007 | Lennox et al. |
| 2007/0173858 A1 | 7/2007 | Engh et al. |
| 2007/0179627 A1* | 8/2007 | Gustilo et al. ............ 623/20.15 |
| 2007/0185581 A1* | 8/2007 | Akizuki et al. ............ 623/20.32 |
| 2007/0233138 A1 | 10/2007 | Figueroa et al. |
| 2007/0233139 A1 | 10/2007 | Metcalfe et al. |
| 2007/0233140 A1 | 10/2007 | Metzger et al. |
| 2007/0260253 A1 | 11/2007 | Johnson et al. |
| 2007/0260322 A1 | 11/2007 | Nowakowski |
| 2007/0276394 A1 | 11/2007 | Johnson et al. |
| 2007/0282451 A1 | 12/2007 | Metzger et al. |
| 2007/0288030 A1 | 12/2007 | Metzger et al. |
| 2008/0004701 A1 | 1/2008 | Axelson, Jr. et al. |
| 2008/0027556 A1 | 1/2008 | Metzger |
| 2008/0027557 A1 | 1/2008 | Tuke |
| 2008/0033567 A1 | 2/2008 | Stchur |
| 2008/0058945 A1 | 3/2008 | Hajaj et al. |
| 2008/0058949 A1 | 3/2008 | Dees, Jr. et al. |
| 2008/0114370 A1 | 5/2008 | Schoenefeld |
| 2008/0119940 A1 | 5/2008 | Otto et al. |
| 2008/0154270 A1 | 6/2008 | Haines et al. |
| 2008/0161815 A1 | 7/2008 | Schoenefeld et al. |
| 2008/0215059 A1 | 9/2008 | Carignan et al. |
| 2008/0257363 A1 | 10/2008 | Schoenefeld et al. |
| 2008/0262624 A1 | 10/2008 | White et al. |
| 2008/0300690 A1 | 12/2008 | Burstein et al. |
| 2008/0312659 A1 | 12/2008 | Metzger et al. |
| 2009/0024131 A1 | 1/2009 | Metzger et al. |
| 2009/0043309 A1 | 2/2009 | Rasmussen |
| 2009/0043310 A1 | 2/2009 | Rasmussen |
| 2009/0043396 A1 | 2/2009 | Komistek |
| 2009/0125351 A1 | 5/2009 | Davis, Jr. et al. |
| 2009/0132055 A1 | 5/2009 | Ferro |
| 2009/0151736 A1 | 6/2009 | Belcher et al. |
| 2009/0163922 A1 | 6/2009 | Meridew et al. |
| 2009/0164022 A1 | 6/2009 | Masini |
| 2009/0204221 A1 | 8/2009 | Walker |
| 2009/0222014 A1 | 9/2009 | Bojarski et al. |
| 2009/0222103 A1 | 9/2009 | Fitz et al. |
| 2009/0222665 A1 | 9/2009 | Sheehan |
| 2009/0228111 A1 | 9/2009 | Otto |
| 2009/0254093 A1 | 10/2009 | White et al. |
| 2009/0254367 A1 | 10/2009 | Belcher et al. |
| 2009/0265012 A1 | 10/2009 | Engh et al. |
| 2009/0307893 A1 | 12/2009 | Burdulis, Jr. et al. |
| 2009/0319047 A1 | 12/2009 | Walker |
| 2009/0319048 A1 | 12/2009 | Shah et al. |
| 2009/0319049 A1 | 12/2009 | Shah et al. |
| 2009/0326664 A1 | 12/2009 | Wagner et al. |
| 2009/0326667 A1 | 12/2009 | Williams et al. |
| 2010/0010635 A1 | 1/2010 | Straszheim-Morley et al. |
| 2010/0016977 A1 | 1/2010 | Masini |
| 2010/0016980 A1 | 1/2010 | Donno et al. |
| 2010/0087829 A1 | 4/2010 | Metzger et al. |
| 2010/0094301 A1 | 4/2010 | Dees, Jr. et al. |
| 2010/0100192 A1 | 4/2010 | Haines et al. |
| 2010/0131071 A1 | 5/2010 | O'Connor et al. |
| 2010/0152782 A1 | 6/2010 | Stone et al. |
| 2010/0160919 A1 | 6/2010 | Axelson, Jr. et al. |
| 2010/0185203 A1 | 7/2010 | Haines |
| 2010/0198224 A1 | 8/2010 | Metzger et al. |
| 2010/0280624 A1 | 11/2010 | Engh et al. |
| 2010/0305711 A1 | 12/2010 | McKinnon et al. |
| 2010/0324692 A1 | 12/2010 | Uthgenannt et al. |
| 2010/0331847 A1 | 12/2010 | Wilkinson et al. |
| 2010/0331848 A1 | 12/2010 | Smith et al. |
| 2011/0015636 A1 | 1/2011 | Katrana et al. |
| 2011/0015639 A1 | 1/2011 | Metzger et al. |
| 2011/0015749 A1 | 1/2011 | Engh et al. |
| 2011/0029091 A1* | 2/2011 | Bojarski et al. ............ 623/20.32 |
| 2011/0046735 A1 | 2/2011 | Metzger et al. |
| 2011/0054478 A1 | 3/2011 | Vanasse et al. |
| 2011/0060340 A1 | 3/2011 | Dees, Jr. et al. |
| 2011/0071533 A1 | 3/2011 | Metzger et al. |
| 2011/0082559 A1 | 4/2011 | Hartdegen et al. |
| 2011/0251694 A1* | 10/2011 | Wasielewski ............... 623/19.11 |
| 2012/0022659 A1* | 1/2012 | Wentorf ...................... 623/20.32 |
| 2012/0022660 A1* | 1/2012 | Wentorf ...................... 623/20.32 |
| 2013/0024001 A1* | 1/2013 | Wentorf et al. ............ 623/20.32 |
| 2013/0131820 A1* | 5/2013 | Wentorf et al. ............ 623/20.34 |
| 2014/0025175 A1* | 1/2014 | Wentorf et al. ............ 623/20.32 |
| 2014/0025177 A1* | 1/2014 | Wentorf et al. ............ 623/20.32 |

FOREIGN PATENT DOCUMENTS

| | | |
|---|---|---|
| DE | 69918894 | 8/2005 |
| DE | 60304233 | 1/2007 |
| EP | 0189253 | 7/1986 |
| EP | 0336774 | 10/1989 |
| EP | 0592750 | 4/1994 |
| EP | 0627202 | 12/1994 |
| EP | 0672397 | 9/1995 |
| EP | 0674887 | 10/1995 |
| EP | 0709074 | 5/1996 |
| EP | 0950387 | 10/1999 |
| EP | 0956836 | 11/1999 |
| EP | 1136045 | 9/2001 |
| EP | 1327423 | 7/2003 |
| EP | 2155120 | 11/2008 |
| FR | 2685632 | 7/1993 |
| FR | 2835178 | 8/2003 |
| GB | 2312166 | 10/1997 |
| GB | 2312377 | 10/1997 |
| GB | 2403416 | 1/2005 |
| GB | 2422110 | 7/2006 |
| GB | 2429648 | 3/2007 |
| JP | 1011541 | 1/1989 |
| WO | WO9729704 | 8/1997 |
| WO | WO2008/144393 | 11/2008 |
| WO | WO2009/068951 | 6/2009 |
| WO | WO2009/088238 | 7/2009 |
| WO | WO2009/105495 | 8/2009 |
| WO | WO2009/105496 | 8/2009 |

(56) References Cited

FOREIGN PATENT DOCUMENTS

| WO | WO2009/158318 | 12/2009 |
| WO | WO2010/006677 | 1/2010 |
| WO | WO2010/010536 | 1/2010 |

OTHER PUBLICATIONS

Chiu, et al., "Bilateral total knee arthroplasty: One mobile-bearing and one fixed-bearing," *Journal of Orthopaedic Surgery*, 9(1):45-50 (2001).

Brochure entitled Online Orthopaedics, Total Knee Replacement, LCS® Complete Mobile-Bearing Knee System, pp. 1-4 (May 1, 2010) http://www.orthopodsurgeon.com/kneereplace.html Accessed Jul. 23, 2010.

Brochure entitled LCS® My knee. My life™ Family Brochure, DePuy, a Johnson & Johnson company, 20 pages (2008).

Brochure entitled Stryker Joint Replacement Scorpio NRG Non Restricted Geometry, Cruciate Retaining Knee System, Posterior Stabilized Knee System, 52 pages (Undated).

Brochure entitled Stryker Orthopaedics Scorpio NRG The Evolution of a High Performance Knee System, 16 pages (2007).

Brochure entitled Triathlon™ Knee System Design Rationale Surgical Instrumentation and Implants Knee Technology Designed for Natural Motion, 16 pages (2004) Stryker.

International Search Report and Written Opinion in International Application No. PCT/US2011/022922, mailed Oct. 24, 2011.

International Preliminary Report on Patentability in International Application No. PCT/US2011/022922, mailed Jul. 31, 2012.

Buechel, FF, "NJ LCS Unicompartmental Knee System with Porocoat: Surgical Procedure," Oct. 24, 1994, Bates No. DEP00004117-DEP00004130, 15 pages.

Buechel, FF, "NJ LCS Unicompartmental Knee System with Porocoat," 1994, Bates No. DEP00004142-DEP00004152, 11 pages.

Engh, G.A., et al., "The AMK Total Knee System, Design Rationale and Surgical Procedure," Published by DePuy, 1989, Bates No. DEP00004153-DEP00004201, 50 pages.

Whiteside Ortholoc Total Knee System: Surgical Procedure, Dow Corning Wright, pp. WMT000001-WMT000040, Jun. 1985, 41 pages.

Whiteside Ortholoc Total Knee System, Dow Corning Wright, 1983, pp. ZH0001 09679-ZH0001 09690, 13 pages.

\* cited by examiner

80 DEGREES

90 DEGREES

100 DEGREES

110 DEGREES

120 DEGREES

130 DEGREES

140 DEGREES

150 DEGREES

CRUCIATE-RETAINING KNEE PROSTHESIS

CROSS REFERENCE TO RELATED APPLICATIONS

This application is a non-provisional application of U.S. Provisional Application Ser. No. 61/372,556 filed on Aug. 11, 2010 and titled "Cruciate-Retaining Knee Prosthesis," U.S. Provisional Application Ser. No. 61/382,287 filed on Sep. 13, 2010 and titled "Cruciate-Retaining Prosthesis," and U.S. Provisional Application Ser. No. 61/299,835 filed on Jan. 29, 2010 and titled "Bi-Cruciate Retaining Tibial Implant," the contents of all three of which are hereby incorporated by reference.

RELATED FIELDS

Prostheses for use in knee arthroplasty, such as tibial and/or femoral implants, which may in some instances facilitate the retention of one or both cruciate ligaments.

BACKGROUND

In total knee arthroplasty, the convention is to resect the entire proximal tibia to create a plateau surface on which a tibial base prosthesis can be implanted. Such conventional resection techniques typically sacrifice one or both of the anterior cruciate ligament (ACL) and the posterior cruciate ligament (PCL) since the resections removed the bony attachment site for those ligaments (the "tibial eminence"). Often, PCL and ACL functions are replaced by the prosthesis, which may utilize a stabilizing post on the tibial insert and a corresponding receptacle on the femoral component or increased sagittal conformity. While these prostheses generally restore anterior-posterior stability, they may not feel as "natural" as a normal knee and are less tissue-conserving.

If any one or both of the cruciate ligaments are salvageable, it is sometimes desirable (especially for young and active patients) to conserve either or both the ACL and PCL, in order to preserve natural biomechanics, range of motion, and feeling.

In current PCL-sparing knee implants, a posterior portion of the tibial insert and/or tibial base member may have a slight cut-out to provide space for the PCL and its attachment site on a remaining portion of the tibial eminence. A surgeon must remain careful not to resect portions of bone adjacent the PCL attachment areas. The ACL is generally sacrificed when using these so-called posterior cruciate-retaining prostheses.

Alternatively, a surgeon may attempt to preserve both the ACL and PCL, which is sometimes accomplished by installing two unicondylar implants. The tibial eminence and cruciate ligaments attached thereto are left intact. The medial and lateral tibial plateau areas are resected and replaced with separate unicondylar tibial trays and corresponding inserts. One disadvantage of implanting two separate unicondylar implants includes the difficulty in properly aligning the two implants in relation to each other. If the two implants are not aligned properly, wear may be accelerated, mechanical axis alignment may be compromised, and femoral motion may feel unnatural to the patient. Surgical implantation time may also be increased due to the added complexity of installing two implants instead of one.

In lieu of two separate unicondylar implants, surgeons have the alternative option of preserving both the ACL and PCL by implanting a single bi-cruciate retaining implant, which comprises a single tibial bearing member (which may be an insert) and/or tibial base member. Prior art bi-cruciate retaining implants are essentially formed of an insert and a base member, each having two unicondylar portions joined by a thin anterior bridge which connects the two. The thin anterior bridges may fail to support the high torsional loading experienced by active patients, and past implants have been known to eventually bend or shear in half over time, requiring premature revision surgery. Even minor bending and shearing experienced by such prior art devices may reduce performance and eventually cause loosening or de-laminating of the implant from the bone on either or both of the medial and lateral sides.

Additional problems with prior bi-cruciate retaining designs include fracture of the bone adjacent to the area connecting the ACL to the tibia (i.e., the anterior tibial eminence). Such fractures are especially common when bone portions anterior to the ACL attachment point are removed in order to provide enough space for the medial and lateral side portions to be connected by said thin anterior bridge.

SUMMARY

When compared to prior art designs, at least some of the embodiments of the cruciate-retaining tibial prostheses described herein provide greater rigidity, torsional and bending stiffness, and resistance to torsional flexing, bending, and/or shearing between medial and lateral tibial portions.

These and other embodiments provide additionally or alternatively a tibial prosthesis for at least partially replacing a proximal portion of a tibia, the tibial prosthesis comprising an inferior surface for contact with a resected surface on the proximal portion of the tibia, and a keel for penetration into a cavity formed in the proximal tibia, wherein the keel extends at an inferior-posterior angle away from the inferior surface, wherein the tibial prosthesis defines a central notch extending between the medial and lateral baseplate portions posterior to the connecting baseplate portion, wherein the central notch has a sufficient width and length to receive a portion of a tibial eminence including an anterior cruciate ligament attachment site and a posterior cruciate ligament attachment site, and wherein the central notch comprises a medial edge and a lateral edge, wherein an angle defined by the medial edge and a base of the anterior keel portion is acute, and wherein an angle defined by the lateral edge and the base of the anterior keel portion is obtuse.

Also disclosed are tibial prostheses wherein a posterior face of the anterior keel portion is offset from a posterior face of the connecting baseplate portion.

Also disclosed are tibial prostheses wherein a superior surface of the tibial prosthesis includes at least one lock member for securing a tibial insert.

Also disclosed are tibial prostheses wherein a superior surface of the tibial prosthesis includes at least two lock members for securing a medial tibial insert and a lateral tibial insert.

Also disclosed are tibial prostheses for at least partially replacing a proximal portion of a tibia, the tibial prosthesis comprising a medial baseplate portion, the medial baseplate portion having a medial inferior surface for contact with a medial resected surface on the proximal portion of the tibia, a lateral baseplate portion, the lateral baseplate portion having a lateral inferior surface for contact with a lateral resected surface on the proximal portion of the tibia, a connecting baseplate portion extending between the medial and lateral baseplate portions, wherein the tibial prosthesis is asymmetric about a midline extending in an anteriorposterior direction between the medial and lateral baseplate portions and the medial baseplate portion extends further anteriorly than the lateral baseplate portion.

Also disclosed are tibial prostheses wherein an area defined by the medial baseplate portion in a transverse plane is greater than an area defined by the lateral baseplate portion in the transverse plane.

Also disclosed are tibial prostheses wherein the tibial prosthesis is a bicruciate-retaining tibial prosthesis.

Also disclosed are tibial prostheses wherein the tibial prosthesis defines a notch extending in a generally anterior-posterior direction between the medial and lateral baseplate portions and is positioned posterior to the connecting baseplate portion; and wherein the notch is of sufficient length to receive at least a portion of an eminence of the tibia including an anterior cruciate ligament attachment site and a posterior cruciate ligament attachment site.

Also disclosed are tibial prostheses wherein the notch comprises a medial edge, a lateral edge, and an anterior edge, wherein an angle defined by the medial and anterior edges is acute, and wherein an angle defined by the lateral and anterior edges is obtuse.

Also disclosed is a tibial prosthesis for at least partially replacing a proximal portion of a tibia, the tibial prosthesis comprising a medial baseplate portion comprising a medial inferior surface for contact with a medial resected surface on the proximal portion of the tibia, a lateral baseplate portion comprising a lateral inferior surface for contact with a lateral resected surface on the proximal portion of the tibia, a connection baseplate portion extending between the medial and lateral baseplate portions, the connection baseplate portion comprises a connection inferior surface, a keel for penetration into a cavity formed in the proximal tibia, wherein the keel extends at an inferior-posterior angle away from at least one of the medial inferior surface, the lateral inferior surface, and the connection inferior surface.

Also disclosed are tibial prostheses wherein the keel includes an anterior keel portion, a medial keel portion extending from the medial inferior surface, and a lateral keel portion extending from the lateral inferior surface, wherein the anterior keel portion extends at the inferior-posterior angle away from the connection inferior surface.

Also disclosed are tibial prostheses wherein at least a part of the anterior keel portion extends in a generally medial-lateral direction on the connection baseplate portion, wherein at least a part of the medial keel portion extends in a generally anterior-posterior direction on the medial baseplate portion, and wherein at least a part of the lateral keel portion extends in a generally anterior-posterior direction on the lateral baseplate portion.

Also disclosed are tibial prostheses wherein the anterior keel portion joins the medial and lateral keel portions at areas of increased thickness.

Also disclosed are tibial prostheses wherein the anterior keel portion joins the medial and lateral keel portions at areas of increased width.

Also disclosed are tibial prostheses wherein the connection baseplate portion increases in thickness in an anterior posterior direction.

Also disclosed are tibial prostheses wherein the medial and lateral keel portions decrease in height as the medial and lateral keel portions extend in an anterior to posterior direction.

Also disclosed are tibial prostheses wherein the anterior keel portion extends across the connection baseplate portion in an anterior-medial to a posterior-lateral direction.

Also disclosed are tibial prostheses wherein a posterior face of the anterior keel portion is offset from a posterior face of the connection baseplate portion.

Also disclosed are tibial prostheses wherein the tibial prosthesis defines a central notch extending between the medial and lateral baseplate portions posterior to the connection baseplate portion, wherein the central notch has a sufficient width and length to receive a portion of a tibial eminence including an anterior cruciate ligament attachment site and a posterior cruciate ligament attachment site.

Also disclosed are tibial prostheses wherein the central notch comprises a medial edge and a lateral edge, wherein an angle defined by the medial edge and a base of the anterior keel portion is acute; and wherein an angle defined by the lateral edge and the base of the anterior keel portion is obtuse.

Also disclosed are tibial prostheses wherein the tibial prosthesis is asymmetric about a midline extending in an anterior-posterior direction between the medial and lateral baseplate portions and the medial baseplate portion extends further anteriorly than the lateral baseplate portion.

These or other embodiments provide additionally or alternatively a tibial prosthesis for at least partially replacing a proximal portion of a tibia, comprising a tibial articulation surface for articulation with a femoral condylar articulation surface, wherein the tibial articulation surface defines a mesial lip extending in an anterior to posterior direction along a mesial edge of the articulation surface; wherein the mesial lip is raised by a height relative to a corresponding central portion of the articulation surface; and wherein the height with which the mesial lip is raised relative to the corresponding central portion decreases in an anterior to posterior direction.

Also disclosed are tibial prostheses wherein the tibial articulation surface is a medial tibial articulation surface and wherein at least a portion of the medial tibial articulation surface is concave in a sagittal plane.

Also disclosed are tibial prostheses wherein an anterior-mesial portion of the medial tibial articulation surface is curved to at least partially conform to the femoral condylar articular surface.

Also disclosed are tibial prostheses wherein a posterior-outer portion of the medial tibial articulation surface is substantially flat and does not substantially conform to the femoral condylar articular surface.

Also disclosed are tibial prostheses wherein the tibial articulation surface is a lateral tibial articulation surface; and wherein the lateral tibial articulation surface is convex in a sagittal plane.

Also disclosed are tibial prostheses wherein an anterior-mesial portion of the lateral tibial articulation surface is curved to at least partially conform to the femoral condylar articular surface.

Also disclosed are tibial prostheses wherein a posterior-outer portion of the lateral tibial articulation surface is substantially flat and does not substantially conform to the femoral condylar articular surface.

Also disclosed are tibial prostheses wherein the tibial prosthesis is a tibial insert; and wherein the tibial insert further comprises an inferior surface that includes at least one lock member for securing to a tibial baseplate.

Also disclosed is a tibial prosthesis for at least partially replacing a proximal portion of a tibia, comprising a tibial articulation surface for articulation with a femoral condylar articulation surface, wherein the tibial articulation surface defines a mesial lip extending in an anterior to posterior direction along a mesial edge of the articulation surface, wherein the mesial lip is raised by a height relative to a corresponding central portion of the articulation surface, and wherein an anterior-mesial portion of the medial tibial articulation surface is curved to at least partially conform to the femoral condylar articular surface, and wherein a posterior-outer portion of the medial tibial articulation surface is substantially flat and does not substantially conform to the femoral condylar articular surface.

Also disclosed is a tibial prosthesis for at least partially replacing a proximal portion of a tibia, comprising: a tibial articulation surface for articulation with a femoral condylar articulation surface, wherein an anterior-mesial portion of the tibial articulation surface at least partially conforms to the femoral condylar articulation surface and a posterior-outer portion of the tibial articulation surface does not substantially conform to the femoral condylar articulation surface.

Also disclosed are tibial prostheses wherein the anterior-mesial portion is curved to at least partially conform to the femoral condylar articulation surface.

Also disclosed are tibial prostheses wherein the posterior-outer portion is substantially flat such that the posterior-outer portion does not substantially conform to the femoral condylar articulation surface.

Also disclosed are tibial prostheses wherein the tibial articulation surface is a medial tibial articulation surface; and wherein the medial tibial articulation surface is concave in a sagittal plane.

Also disclosed are tibial prostheses, wherein the tibial articulation surface is a lateral tibial articulation surface; and wherein the lateral tibial articulation surface is convex in a sagittal plane.

According to other embodiments, a tibial prosthesis for at least partially replacing a proximal portion of a tibia is also provided, the tibial prosthesis comprising: a tibial articulation surface for articulation with a femoral condylar articulation surface, wherein the tibial articulation surface defines a mesial lip extending in an anterior to posterior direction along a mesial edge of the articulation surface, wherein the mesial lip is raised by a height relative to a corresponding central portion of the articulation surface, wherein the height with which the mesial lip is raised relative to the corresponding central portion decreases in an anterior to posterior direction, an anterior-mesial portion of the tibial articulation surface at least partially conforms to the femoral condylar articulation surface and a posterior-outer portion of the tibial articulation surface does not substantially conform to the femoral condylar articulation surface.

Also disclosed are tibial prostheses wherein the anterior-mesial portion is curved to at least partially conform to the femoral condylar articulation surface.

Also disclosed are tibial prostheses wherein the posterior-outer portion is substantially flat such that the posterior-outer portion does not substantially conform to the femoral condylar articulation surface.

Also disclosed are tibial prostheses further comprising at least one tibial articulation surface for articulation with a femoral condylar articulation surface of a femoral component, wherein the femoral component comprises a medial condyle and a lateral condyle and wherein at least one of the medial condyle and the lateral condyle comprises a posterolateral chamfer.

Also disclosed are tibial prostheses wherein the at least one tibial articulation surface generally slopes in an anterior-posterior direction.

Also disclosed are tibial prostheses wherein the at least one tibial articulation surface comprises a medial articulation surface and a lateral articulation surface, and wherein a slope of the medial articulation surface in the anterior-posterior direction is different from a slope of the lateral articulation surface in the anterior-posterior direction.

Also disclosed are tibial prostheses wherein the medial articulation surface is associated with a medial insert and the lateral articulation surface is associated with a lateral insert, wherein a thickness of the medial insert at an anterior portion of the medial insert is different than a thickness of the lateral insert at a posterior portion of the lateral insert.

Also disclosed are tibial prostheses wherein the thickness of the medial insert at the anterior portion of the medial insert is greater than the thickness of the medial insert at a posterior portion of the medial insert.

Also disclosed are tibial prostheses wherein a thickness of the medial insert at a posterior portion of the medial insert is different than a thickness of the lateral insert at a posterior portion of the lateral insert.

Also disclosed are tibial prostheses wherein the thickness of the lateral insert at the anterior portion of the lateral insert is greater than the thickness of the lateral insert at a posterior portion of the lateral insert.

Also disclosed are tibial prostheses wherein the at least one tibial articulation surface generally slopes in a medial-lateral direction.

Also disclosed are tibial prostheses wherein the at least one tibial articulation surface comprises a medial articulation surface and a lateral articulation surface, and wherein a slope of the medial articulation surface in the medial-lateral direction is different from a slope of the lateral articulation surface in the medial-lateral direction.

Also disclosed are tibial prostheses wherein the medial articulation surface is associated with a medial insert and the lateral articulation surface is associated with a lateral insert, wherein a thickness of the medial insert at an anterior portion of the medial insert is greater than a thickness of the lateral insert at an anterior portion of the lateral insert, and wherein the thickness of the medial insert at a posterior portion of the medial insert is different than the thickness of the lateral insert at a posterior portion of the lateral insert.

Also disclosed are tibial prostheses wherein the anterior keel portion is positioned anteriorly on the connection inferior surface to engage anterior cortical bone when implanted in a patient.

Also disclosed are femoral components having various chamfers to provide additional clearance with respect to the tibial eminence and PCL without decreasing bone coverage. In some embodiments, the medial and/or lateral condyles of the femoral component comprise a posterolateral chamfer. In some embodiments, an anterior flange of the femoral component may comprise an anterolateral chamfer on the lateral and/or medial sides.

Also disclosed are tibial prostheses further comprising at least one tibial articulation surface for articulation with a femoral condylar articulation surface of a femoral component, wherein the femoral component comprises a medial condyle and a lateral condyle and wherein at least one of the medial condyle and the lateral condyle comprises a posterolateral chamfer.

Further areas of applicability will become apparent from the detailed description provided hereinafter. It should be understood that the detailed description and specific examples, while indicating certain embodiments of the invention, are intended for purposes of illustration only and are not intended to limit the scope of the invention.

BRIEF DESCRIPTION OF THE DRAWINGS

The accompanying drawings, which are incorporated in and form a part of the specification, illustrate embodiments of the invention and together with the written description serve to explain the principles, characteristics, and features of the embodiments. It should be noted that while most or all of the drawings contained herein generally illustrate implants configured for use with a patient's left knee, mirrored implants for use with a patient's right knee and symmetrically configured implants for use with both left and right knees are also envisaged.

In the drawings.

DETAILED DESCRIPTION

The following description is merely exemplary in nature of certain selected embodiments and is in no way intended to limit the invention, its application, or uses.

1. Tibial Base Members

FIGS. 1-46 and 97-98 show various, non-limiting embodiments of tibial base members, some of the features of which are discussed below.

Figure 1:
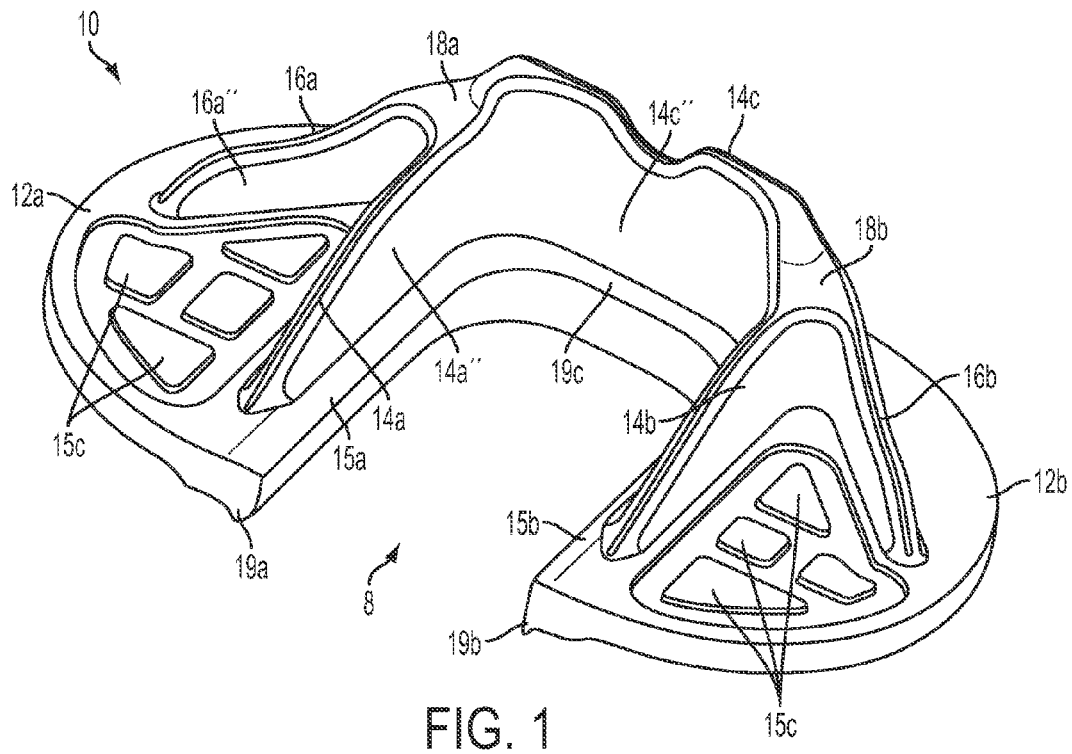
FIGS. 1-3 are bottom isometric views of a tibial base member according to a first embodiment that employs one or more bone ingrowth or cement mantle structures and a plurality of keel portions.
Figure 2:
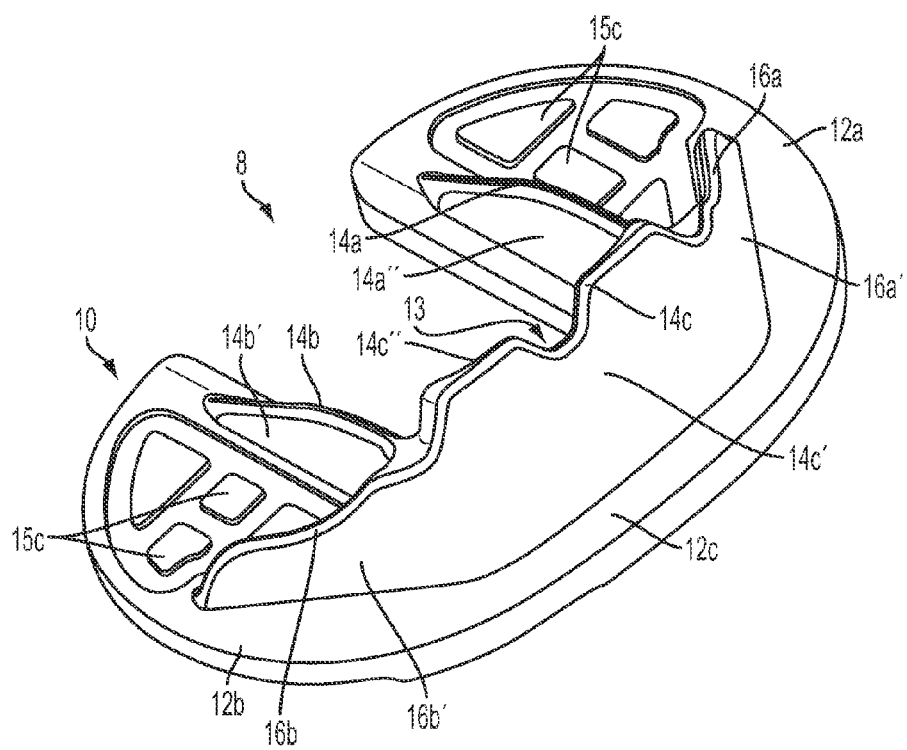
Figure 3:
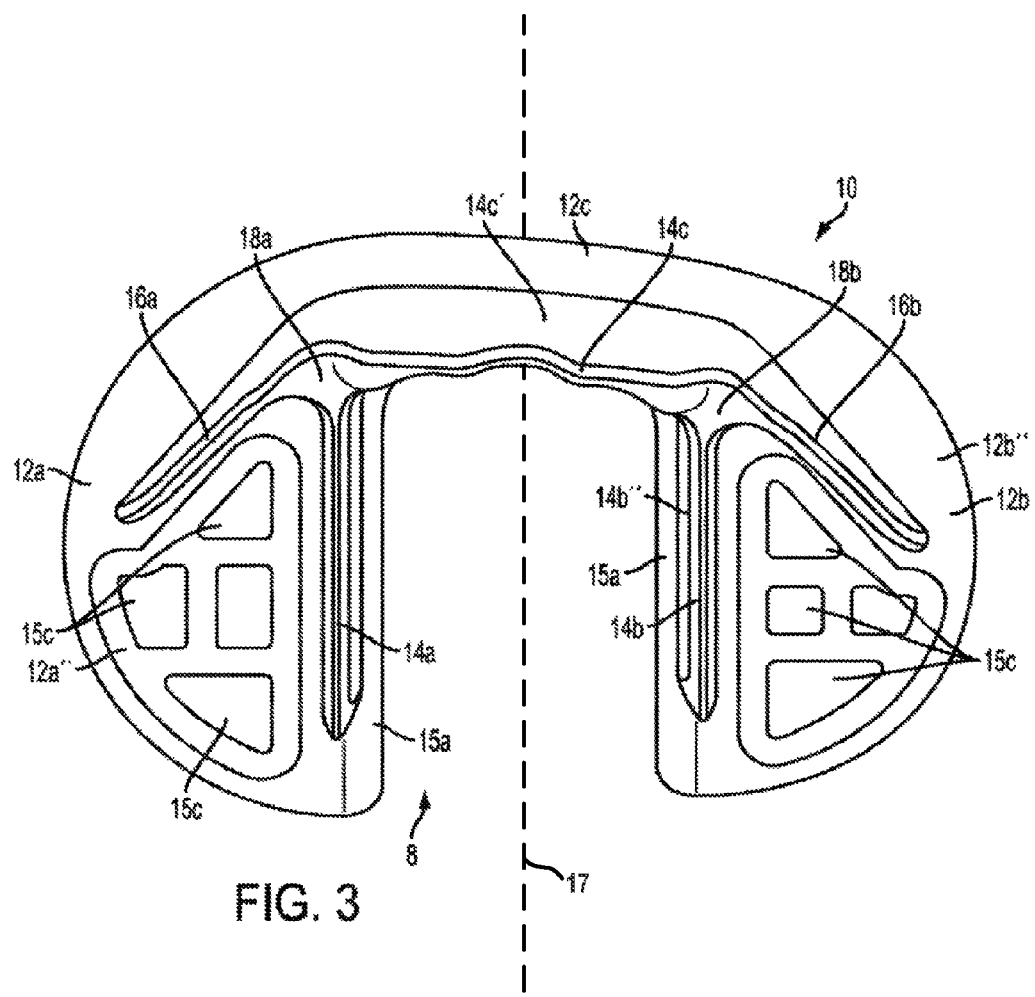
Figure 4:
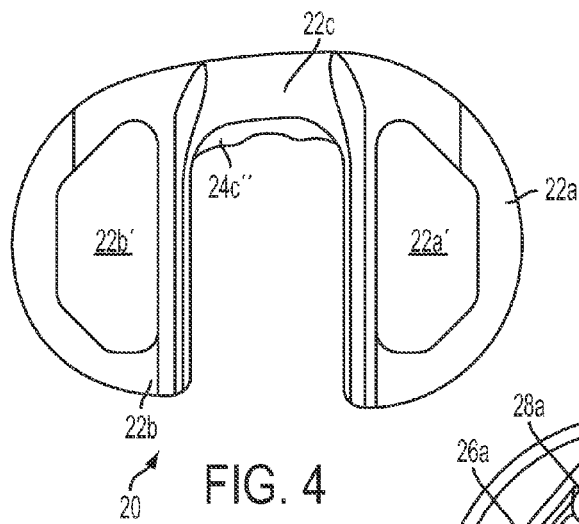
FIGS. 4-7 illustrate a tibial base member according to a second embodiment that includes an underside recess for receiving a cement mantle.
Figure 5:
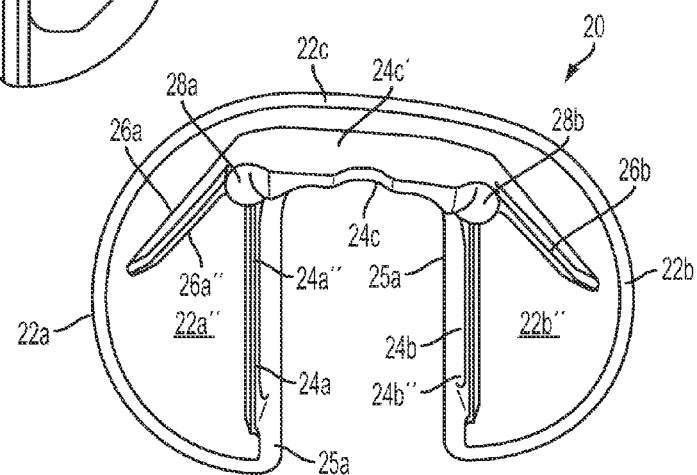
Figure 6:
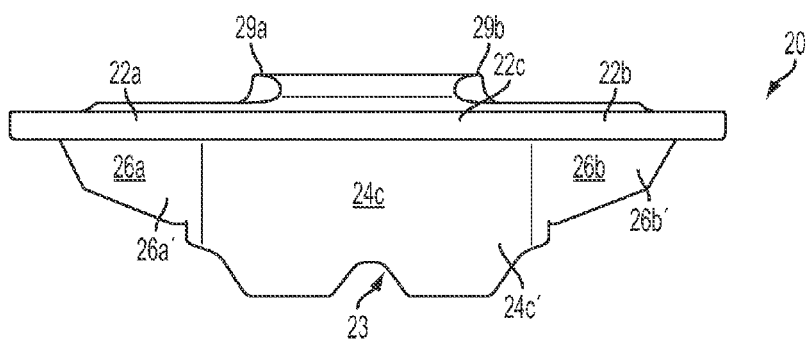

FIGS. 1-3 show the underside of a first embodiment of a tibial base member. Generally, base member 10 includes a medial portion 12a, a lateral portion 12b, and a connecting portion 12c. In this particular embodiment, the base member 10 has an asymmetric shape in some aspects about midline 17. For instance, as shown in FIG. 3, the medial portion 12a is larger than the lateral portion 12b and aspects of the medial portion 12a extend further anteriorly relative to lateral portion 12b. In other embodiments, the base member may reflect other asymmetries or may be symmetric.

The base member 10 of FIGS. 1-3 includes lips 15a and 15b defining a notch, for example, a central notch or cutout portion 8, between medial portion 12a and lateral portion 12b, which may provide clearance for a preserved tibial eminence, or portions thereof. In the embodiment shown in FIGS. 1-3, the central cutout portion 8 is approximately one-quarter to one-third of the tibial medial-lateral width and is thus configured to allow a majority of the tibial eminence to protrude through, although, in some embodiments, it may be desirable to resect at least anterior portions of the eminence. For instance, in some embodiments, an anterior portion of the tibial eminence may be resected flush with the medial and lateral tibial bone resections to provide space for the connecting portion 12c. The amount of tibial bone removed to provide room for a connecting portion 12c may, in some embodiments, be in the range of ⅕ to ⅛ of the total anterior-to-posterior dimension of the tibial eminence prior to bone preparation. In this particular embodiment, the connecting portion 12c is designed to preserve and protect bone around the ACL attachment point, as well as eliminate stress-risers.

As shown, the central cutout portion 8 is generally centered in a medial-lateral direction of the tibial base member 10, which facilitates maintaining the medial/lateral widths of the medial 12a and lateral 12b portions to be generally the same (and, in some embodiments, the medial/lateral widths of inserts used in conjunction with the base member 10). In other embodiments, it is not necessary for the medial 12a and lateral 12b portions to be the same in medial/lateral dimensions.

The base member 10 shown in FIGS. 1-3 includes a keel extending distally therefrom. In some embodiments, the keel may facilitate securing and retaining the base member to the patient's tibia. In some embodiments, the keel may add strength, torsional rigidity and stability to the base member. In the particular embodiment shown, keel portions 14a and 16a extend from the medial portion 12a of base member, keel portions 14b and 16b extend from the lateral portion 12b, and keel portion 14c extends from the connecting portion 12c.

In some embodiments, the keel portions may extend at an angle between approximately 90 degrees and appropriately 45 degrees with respect to the underside of the base member 10, although more or less pronounced angles are also possible. In some embodiments, the keel portions may extend distally at the same general angle or may extend at a different angles with respect to one another. In some embodiments, the keel portions may be symmetric with respect to one another, or may be asymmetrically configured to suit bony anatomy or for other reasons. Other base member embodiments (discussed below) may have more or less keel portions than the base member 10 of FIGS. 1-3 and/or have keel portions of different configurations.

In the particular embodiment of FIGS. 1-3, and as shown best in FIG. 3, the anterior fin 14c angles in a medial-lateral direction such that medial portions of the anterior fin 14c are positioned further anteriorly than lateral portions. Anterior fin 14c also slopes in an anterior/superior to posterior/inferior direction, some of the reasons for which are disclosed in connection with later embodiments described herein. Anterior fin 16c also includes a distal notch 13 (see FIG. 2) to optimize flexibility, reduce material, improve stress distribution, and/or provide additional rotational stability.

The base member of FIGS. 1-3 includes keel portions 16a, 16b extending distally from the medial 12a and lateral 12b portions of base member 10, which, in some embodiments, may improve stability and/or rigidity of the base member 10 against forces that may be exerted thereon, such as forces having at least a component in an anterior and/or posterior direction. Enhanced stability in the anterior-posterior direction may be desirable in some, although not necessarily all, embodiments because certain femoral components (such as femoral component 400 shown in FIGS. 67A-D) may, in some instances and uses, impart such forces on the tibial components used therewith. In some embodiments, the insertion angle and positioning of the one or more keel portions 16a, 16b may be optimized in space for best fixation and best tibial fit, as well as anterior-posterior and rotational stability within the bone. Geometries for the keel portions 16a, 16b other than those shown explicitly in the Figures are also contemplated.

Tibial base member 10 according to some embodiments may have surface finishes that are optimized for use with cemented or uncemented techniques. In some embodiments, the base members have smooth or polished surfaces, or may have a grit blasted surface finish, or other rough surface finishes and textures such as ridges, grooves, steps, flutes, spines, barbs, and combinations thereof. Bottom or distal surfaces of medial portion 12a and lateral portion 12b may also comprise bone ingrowth structures such as a porous ingrowth surfaces with or without hydroxyapatite. In some embodiments, one or more pockets may be provided on the distal or inferior undersurface of base member to accommodate a cement mantle for cemented techniques. The one or more pockets may include means for increasing surface area of contact between the implant and a cement mantle such as a waffle pattern, grooves, ridges, indentations, undercuts, porous portions, protrusions, or bumps 15c, which may be a porous metal material or surface-treated portion of the structure.

The keel portions 14a, 14b, 14c, 16a, and 16b shown in FIGS. 1-3 include outer face surfaces 14a', 14b', 14c', 16a', 16b' respectively and inner face surfaces 14a", 14b", 14c", 16a", 16b" respectively. In some embodiments, these face surfaces may contain porous ingrowth surfaces, roughened surface treatments, hydroxyapatite, or biologics for improved fixation. In some embodiments, inner 14a", 14b", 14c", 16a", 16b" and outer 14a', 14b', 14c', 16a', 16b' face surfaces may be parallel to each other, or may extend at acute angles relative to each other. While shown to be generally planar, face surfaces 14a", 14b", 14c", 16a", 16b", 14a', 14b', 14c', 16a', 16b' of keel portions 14a, 14b, 14c, 16a, 16b, respectively, may be more complex B-spline or arcuate surfaces.

The base member 10 of FIGS. 1-3 includes blends or reinforcing members 18 located between the anterior keel portion 14c and the medial keel portion 14a and the lateral keel portion 14b, which may, in some embodiments, help to minimize the amount of bone removal necessary to accommodate the implant. For instance, on the medial side, strategic blending of the reinforcing member 18a helps keep the bottom edge of the keel portions away from cortical tibial bone. In this way, reinforcing members 18 form transitional areas between the anterior keel portion 14c and the medial keel portion 14a, and between the anterior keel portion 14c and the lateral keel portion 14b.

FIGS. 4-7 illustrate another embodiment of a tibial base member—base member 20. Like the embodiment of FIGS. 1-3, tibial base member 20 includes a medial portion 22a from which a medial fin 24a extends, a lateral portion 22b from which a lateral fin 24b extends, and a connection (or anterior) portion 22c from which an anterior fin 24c extends. Base member 20 may also comprise oblique medial fin 26a and oblique lateral fin 26b. Like the embodiment of FIGS. 1-3, anterior fin 24c may include a distal notch 23 (shown in FIG. 6). Superior surfaces of the base member 20 may comprise a medial locking portion 22a' and lateral locking portion 22b' in the form of recesses that are configured to receive medial and lateral inserts, respectively. Base member 20 also includes medial bone contacting surface 22a" and lateral bone contacting surface 22b" for a cement mantle or which may be a porous ingrowth surface.

Reinforcement members 28a, 28b are generally cylindrical in shape to facilitate bone preparation. For example, drills or small diameter reamers may be used to prepare the bone to accept the thicker regions that form the intersections between the keel portions 24a, 24c, and 24b. Cylindrical and smooth arcuate shapes for the reinforcing member 28a, 28b generally increase the strength at the corners of the cutout between medial 24a and lateral 24b portions, which, in some embodiments, may be high stress areas.

FIGS. 8-11 illustrate a third embodiment, tibial base member 30, which has similar features as the base members 10 and 20 described above. Base member 30 includes a medial eminence lip 39a, a lateral eminence lip 39b, and an anterior eminence lip 39c, shown in FIGS. 8 and 11, which may be provided around the eminence cutout area to increase the overall strength of the base member 30 along its inside edges. This added strength may be particularly important in some embodiments to resist torsional or other forces exerted on the base member 30 when it is loaded posteriorly.

Figure 14:
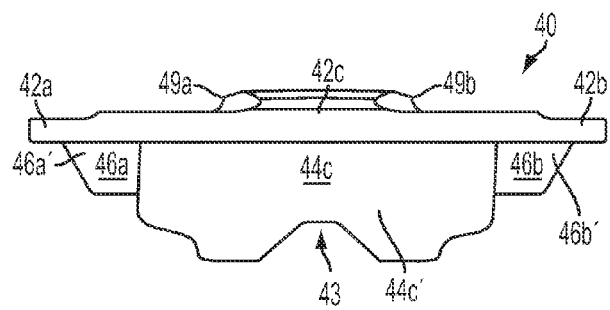
Figure 15:
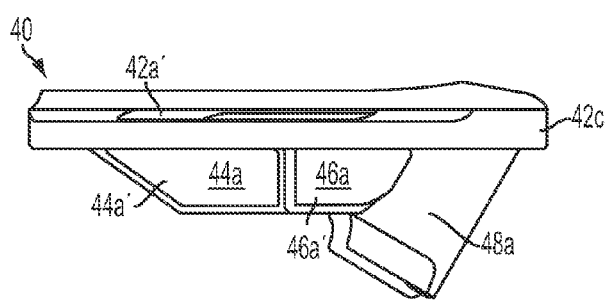
Figure 16:
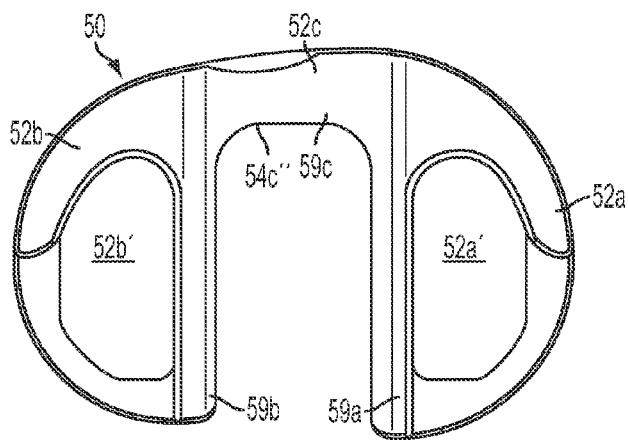
FIGS. 16-19 illustrate a tibial base member according to a fifth embodiment.

FIGS. 12-15 illustrate a fourth embodiment, base member 40, which has similar features as the base members described above with some variations. As one example, as shown in FIG. 14, notch 43 is more pronounced. The configuration of reinforcing members 48a, 48b is also different, as reinforcing members 48a, 48b extend posteriorly and also extend further in a distal direction than the keel portions, such as medial keel portion 44a, as shown in FIG. 15.

Figure 17:
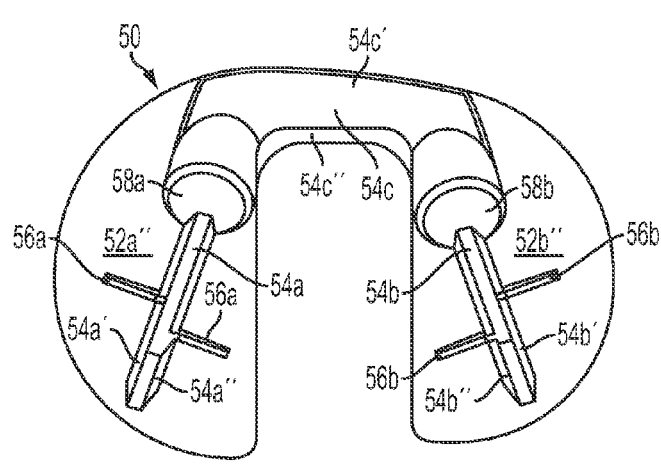
Figure 18:
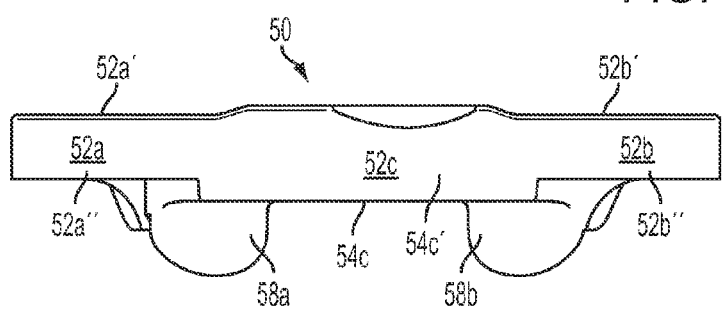
Figure 19:
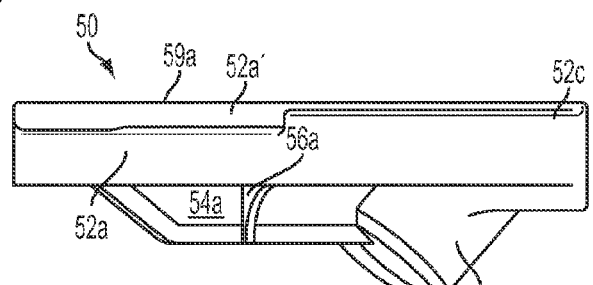
Figure 20:
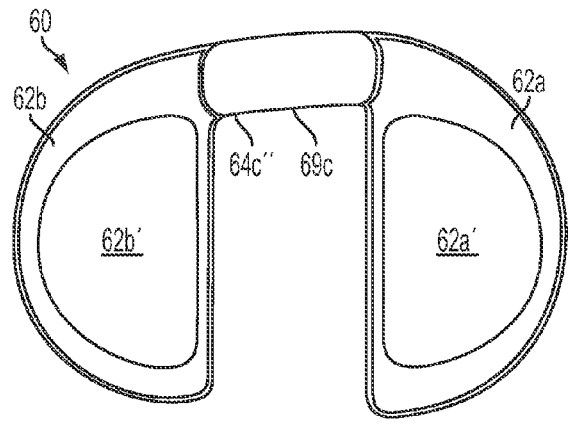
FIGS. 20-23 illustrate a tibial base member according to a sixth embodiment.
Figure 21:
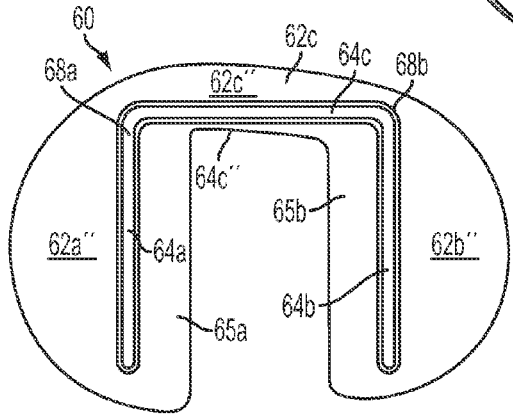

FIGS. 16-19 illustrate a fifth embodiment, base member 50, which also has similar features as the base members described above with some variations. As one example, as shown in FIG. 17, the reinforcing members 58a and 58b are more pronounced. Moreover, as shown in FIG. 17, oblique fins 56a and 56b are positioned differently with respect to medial and lateral portions 52a, 52b than in other embodiments.

Figure 22:
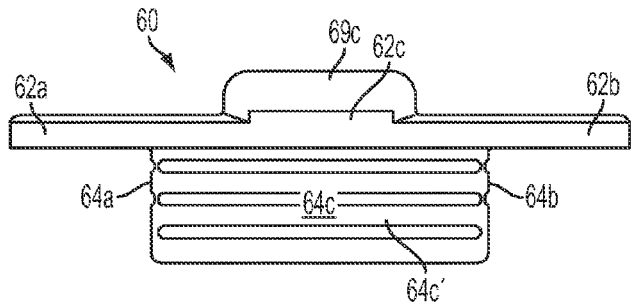
Figure 23:
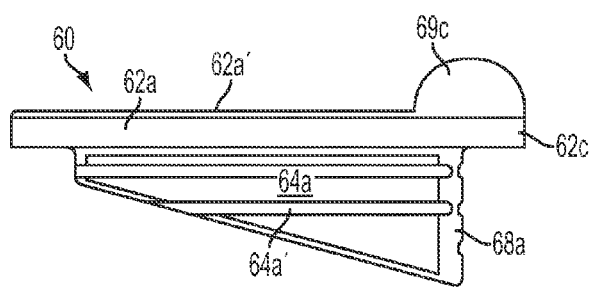
Figure 24:
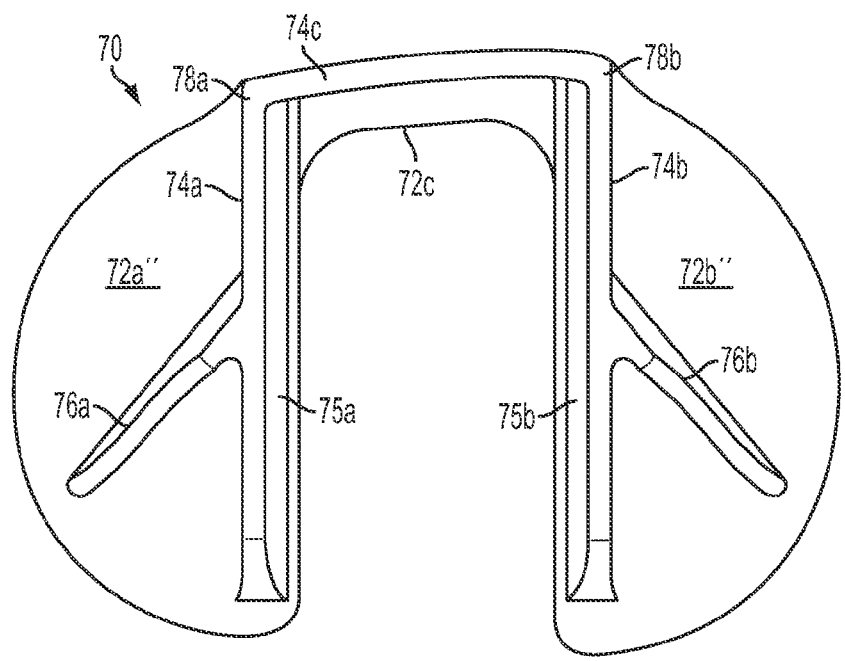
FIGS. 24-29 illustrate a tibial base member according to a seventh embodiment, the base member having an anterior wall portion configured to contact an external portion of cortical bone adjacent to the anterior cortex of the tibia.
Figure 25:
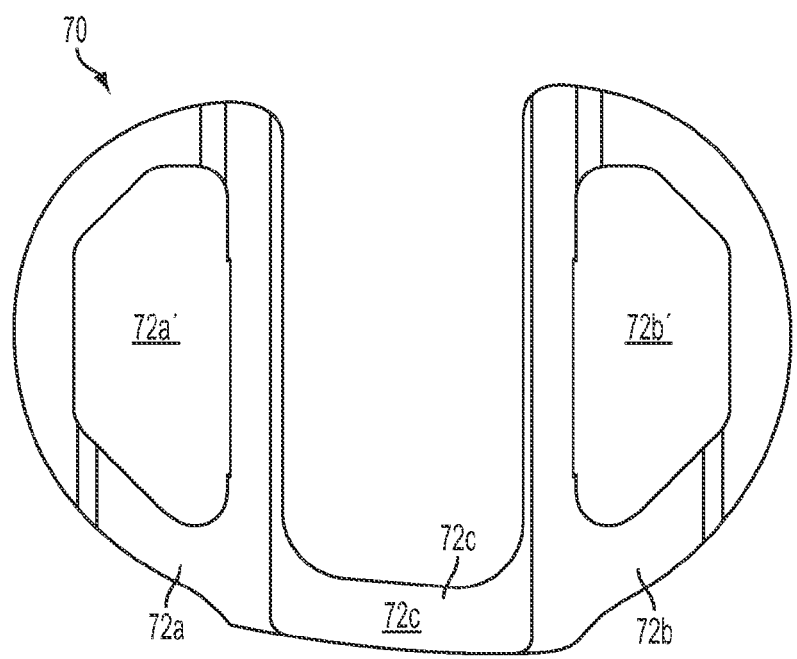
Figure 26:
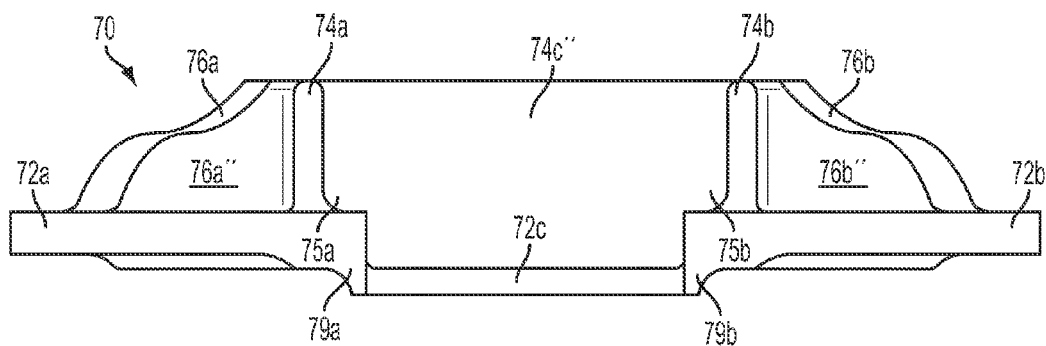
Figure 27:
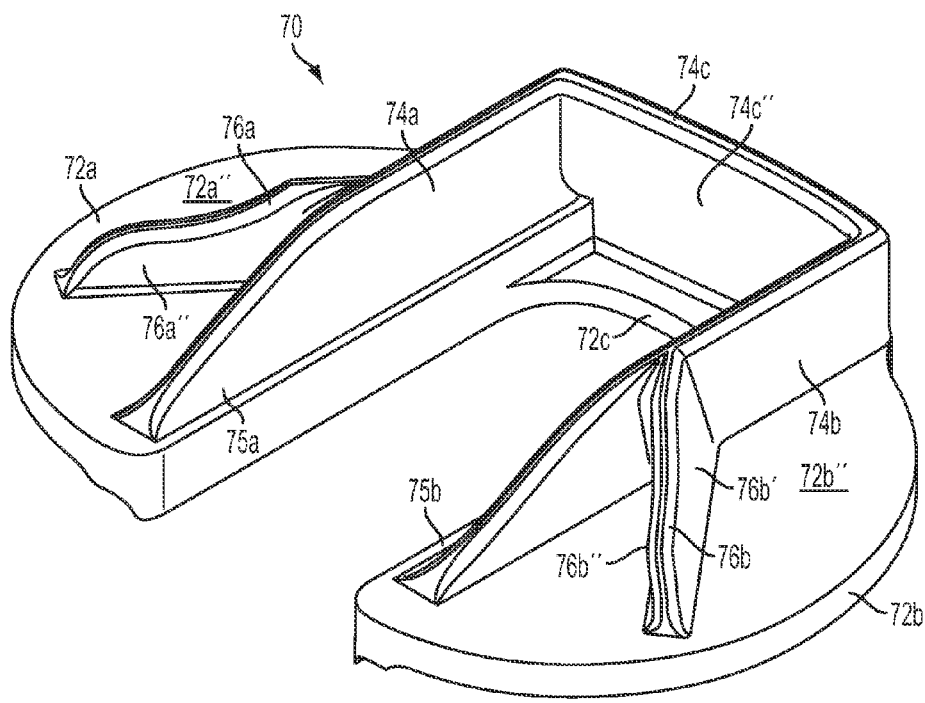
Figure 28:
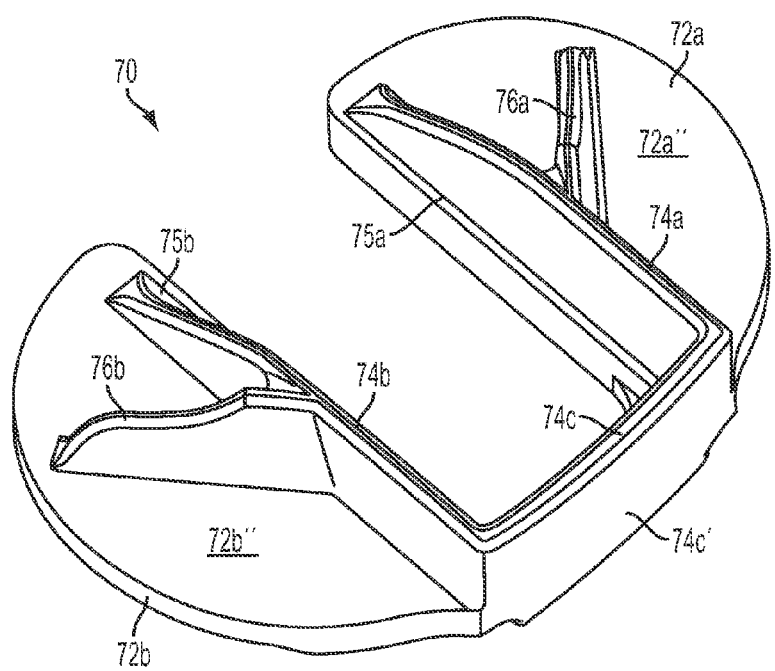
Figure 29:
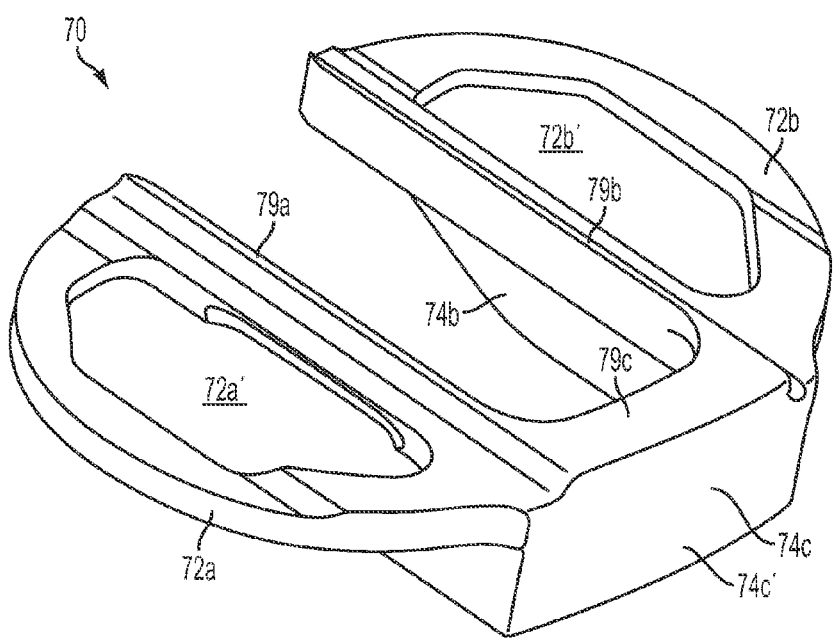

FIGS. 20-23 illustrate a six embodiment, base member 60, which has similar features as the base members described above with some variations. For instance, base member 60 includes a medial fin 64a, an anterior fin 64c, and a lateral fin 64b, but does not include oblique fins. As shown in FIG. 22, anterior fin 64c includes grooves or other surface modifications. Base member 60 also includes an anterior eminence lip 69c, which extends proximally from a superior surface of the base member (as shown in FIGS. 22-23).

FIGS. 24-29 illustrate a seventh embodiment, base member 70, which has similar features as the base members described above with some variations. Base member 70 includes a medial fin 74a, an anterior fin 74c, a lateral fin 74b, and oblique fins 76a, 76b, which extend at an angle from medial and lateral fins 74a, 74b, respectively. Anterior fin 74c is positioned more anteriorly than in other embodiments, so as to engage anterior cortical bone on its inner surface 74c" and sit on an external cortical bone surface adjacent to the anterior cortex. Base member 70 includes a medial eminence lip 79a, a lateral eminence lip 79b, and an anterior eminence lip 79c, shown in FIGS. 26 and 29, which may be provided along the medial and lateral sides of the eminence cutout area to increase the overall strength of the base member 70 along inside edges.

Figure 33:
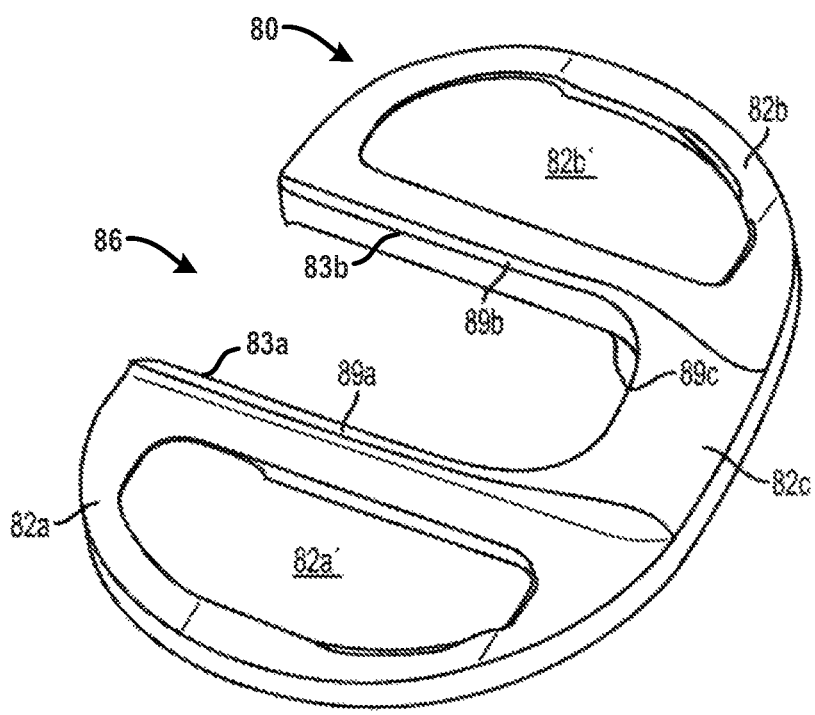
Figure 34:
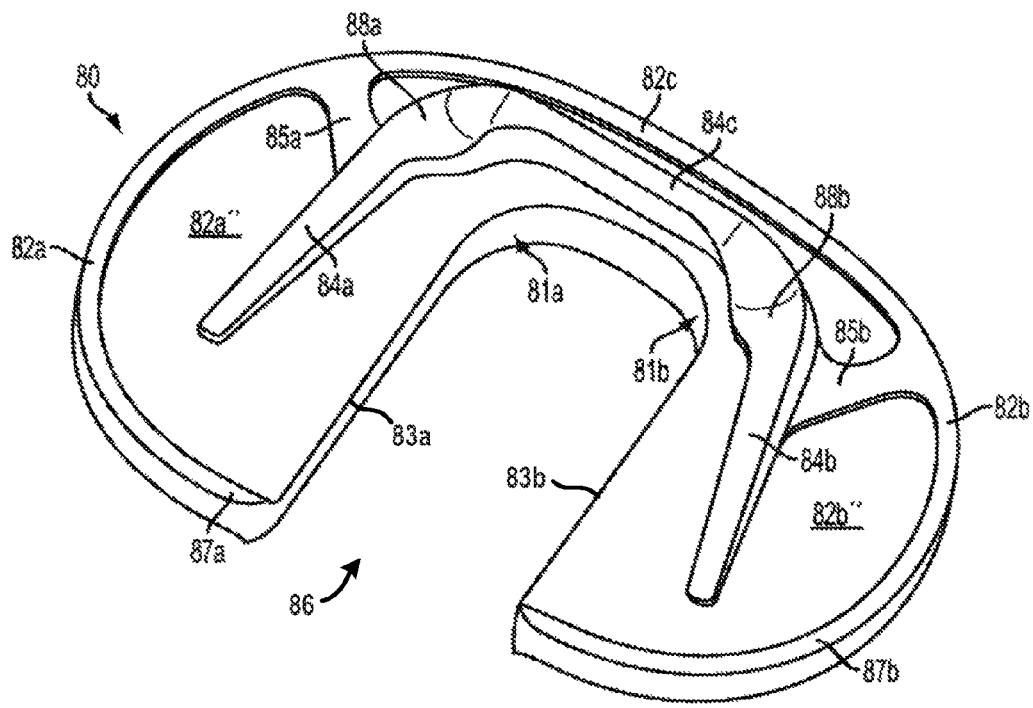
Figure 35:
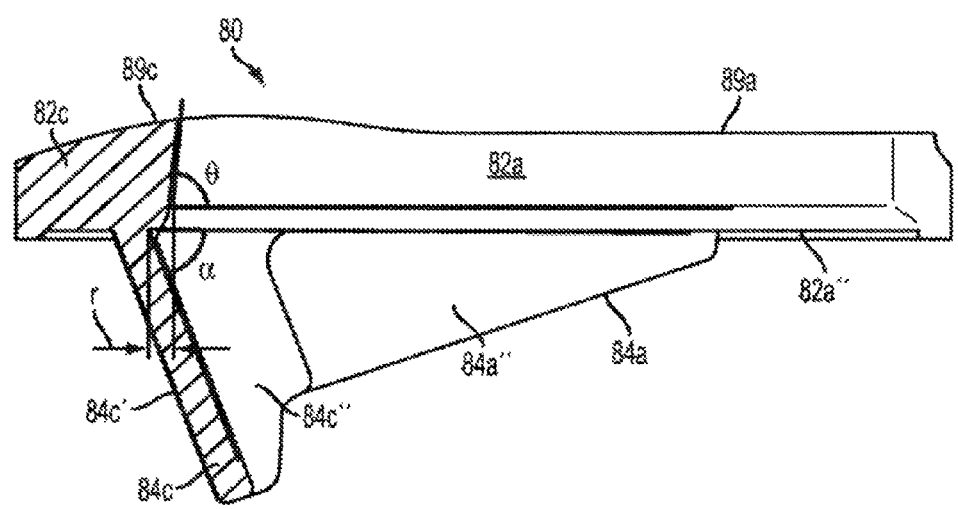
Figure 96:
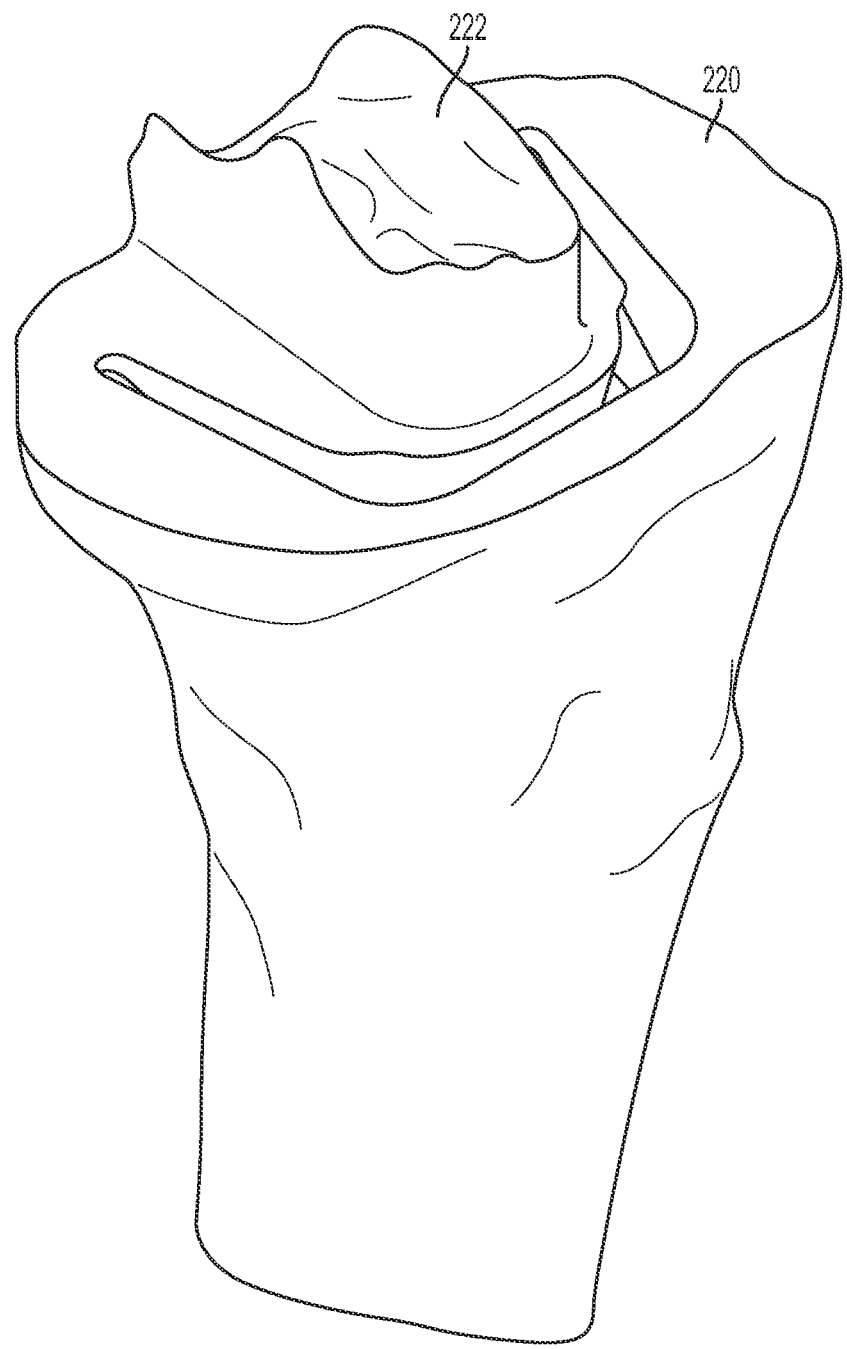
FIG. 96 is a perspective view of a resected tibia prepared to receive the tibial base member of FIGS. 30-35 and 47.

FIGS. 30-35 and 47 illustrate an eighth embodiment, base member 80, having three keel portions—medial keel portion 84a, anterior keel portion 84c, and lateral keel portion 84b. FIG. 96 illustrates a resected tibia 220 prepared to receive the base member 80. As shown in FIG. 96, the tibial eminence 222 is intact. As shown in FIG. 35, anterior keel portion 84c extends further distally than medial and lateral keel portions 84a, 84b, which, in some embodiments, may enhance fixation. In addition, and as with some of the previous embodiments, anterior keel portion 84c is angled and extends in a superior-anterior to inferior-posterior direction (see FIG. 35) in relation to the tibial resection plane and/or the underside of anterior portion 82c, which may, in some embodiments facilitate increasing the depth of the keel portion for strength and fixation without adversely interfering with the anterior cortex of the tibia, and, in some embodiments, without requiring the connecting portion 82c to be located so far posteriorly that it would interfere with the ACL attachment point on the eminence. In some embodiments, the slope of the anterior keel portion 84c helps prevent penetration of the anterior cortical bone of the proximal tibia, or splitting or cracking of the proximal tibia during insertion and impaction. In some embodiments, the slope of the anterior keel portion 84c increases the amount of bone preserved between the anterior fin 84c and the anterior tibial cortical bone. In this particular embodiment, the angle α between the inside surface 84c" of the anterior keel portion 84c and a bone contacting undersurface 82a", 82b" of the base member 80 is between approximately 50 and approximately 90 degrees, and more preferably between approximately 65 and approximately 75 degrees, for example approximately 70 degrees. In some embodiments, medial keel portion 84a and lateral keel portion 84b also extend at an inferior-posterior angle in some aspects, e.g. the top surfaces of those keel portions.

As best shown in FIG. 35, in some embodiments, the posterior face of the anterior connecting portion 84c (which is adjacent to lip 89c) and the posterior side 84c" of the anterior keel portion 84c may not intersect at the level of the proximal tibial resection plane, so as, in some embodiments, help to avoid weakening the anterior portion of the tibial eminence during the anterior keel portion preparation or cause fracture. In other words, the intersection of these two surfaces is offset a predetermined distance (r—shown in FIG. 35) to ensure that preparation of the bone for the anterior keel portion 82c does not compromise the preserved eminence.

As also shown in FIGS. 34 and 35, the angle θ between the lip 89c of the anterior connecting portion 82c and a bone contacting undersurface 82a", 82b" of the base member 80, in this particular embodiment, is between approximately 60 and approximately 90 degrees, and more preferably between approximately 82 and approximately 88 degrees, for example approximately 85 degrees. This angle θ effectively creates an undercut to increase the amount of bone preserved at the anterior base portion of a prepared anterior eminence and thereby reduces bone stresses. In other words, the anterior cut of the eminence is tapered in some embodiments such that the base area of the eminence is greater than its proximal area, which improves the pull-off strength of the eminence 222. The undercut formed by angle θ may also allow bone cement, putty, or other biologic materials to readily flow to the anterior base regions of the eminence 222 thereby strengthening and filling in stress risers that may be located at the corner of the base of the anterior eminence where the anterior eminence bone cut meets the proximal tibial resection. Material placed or packed into and around the undercut angle θ between the bone and the tibial base member 80 may also hold down portions of the bone once implanted, prevent micromotion of the tibial base member 80, and avoid subsidence. As previously stated, the abovementioned angles and other geometric features may be altered to optimally suit a patient's individual anatomy.

Figure 30:
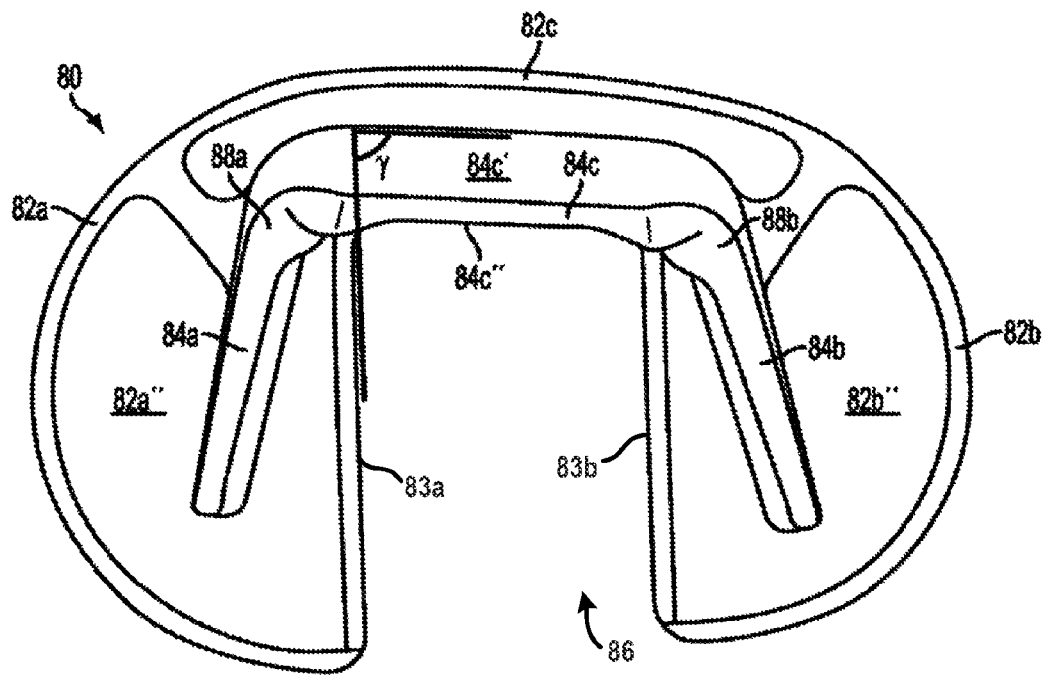
FIGS. 30-35 and 47 illustrate a tibial base member according to an eighth embodiment, the tibial base member having three keel portions.
Figure 31:
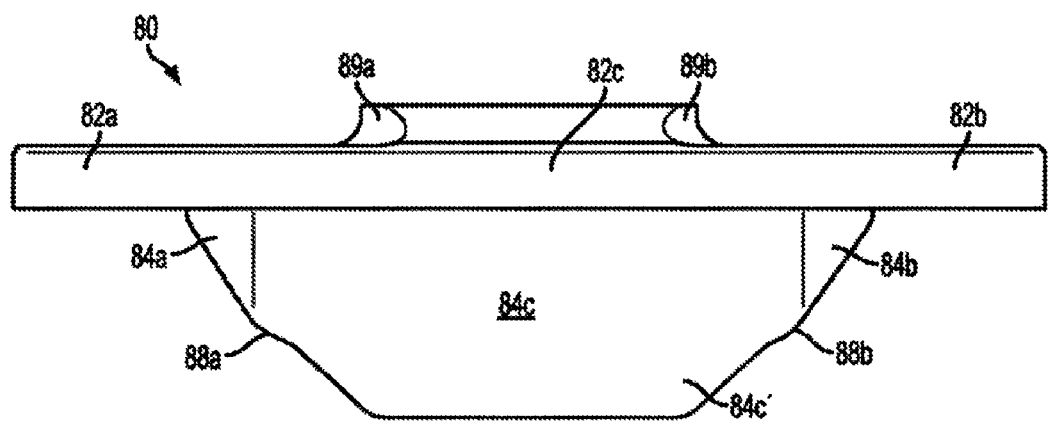
Figure 32:
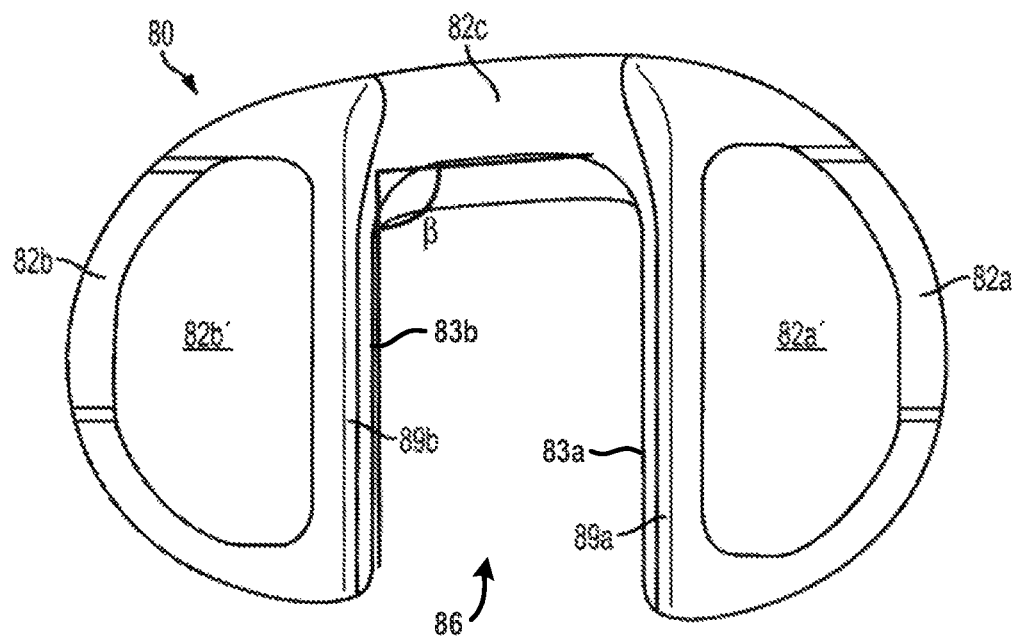

As best shown in FIG. 30, the angle γ between the anterior fin 84c and the medial edge 83a at the inside of the medial portion 82a of this particular embodiment is between approximately 75 and approximately 90 degrees, and more preferably between approximately 82 and approximately 88 degrees, for example approximately 85.5 degrees. As best shown in FIG. 32, the angle β between the anterior connecting portion 82c and the lateral edge 83b at the inside of the lateral portion 82b, in this particular embodiment, is between approximately 90 and approximately 120 degrees, and more preferably between approximately 92 and approximately 98 degrees, for example approximately 95 degrees. In other words, the anterior edge of the central notch or cutout portion 86 between medial 82a and lateral 82b portions is angled such that the medial side of connecting portion 82c lies more anteriorly than the lateral side of the connecting portion 82c. The additional anterior space on the anteromedial side of the central notch or cutout portion 86 of the base member 80, in this particular embodiment, provides better clearance for the ACL, which is generally located more anteriorly on medial sides of the ACL attachment region. The more posteriorly positioned lateral side of connecting portion 82c also avoids interference with the attachment of the posterolateral bundle of the ACL and provides more material on the lateral side for improved strength of the asymmetric design. For custom or patient-specific tibial base members, the abovementioned angles and other geometric features may be altered to optimally suit the patient's individual anatomy. Such changes may be made to satisfy the proper balance between bone conservation and strength.

In the embodiment shown in FIGS. 30-35 and 47, keel portions 84a, 84b, 84c widen or thicken as they approach an intersection with the other keel portions. In some embodiments, such as in the embodiment of FIGS. 30-35, these blends and transitions of the reinforcing members 88a, 88b on the sides of the anterior portion 82c of the base member 80 reduce the stress risers as the top and inside surface portions of the base member 80 transition to the anterior portion 82c from the medial 82a and lateral 82b sides, where material thickness is limited, so as to preserve minimum tibial insert thicknesses and allow the inserts to slide in and engage locking portions 82a', 82b' from the anterior side.

Figure 7:
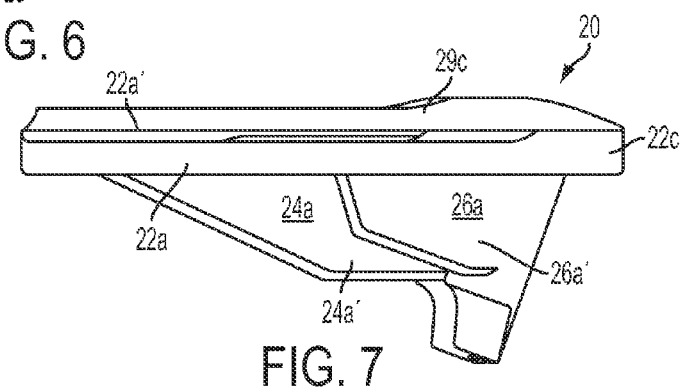
Figure 8:
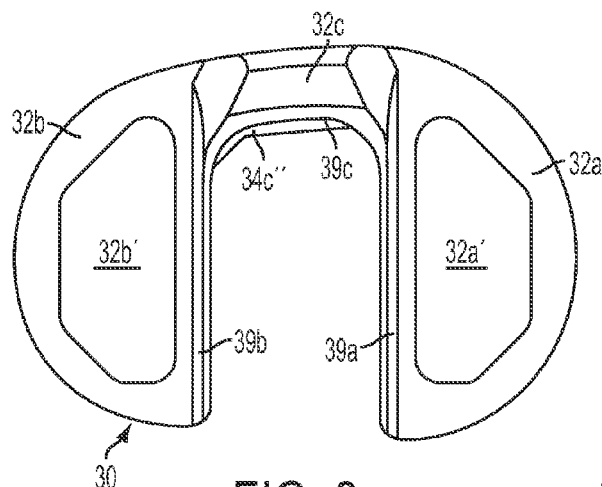
FIGS. 8-11 illustrate a tibial base member according to a third embodiment.
Figure 9:
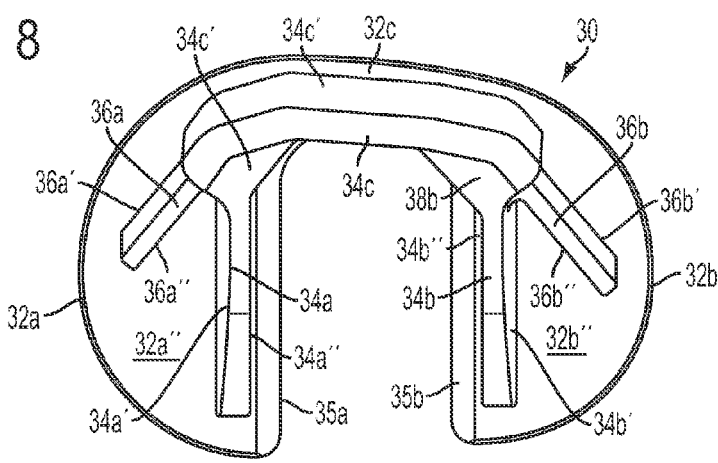
Figure 10:
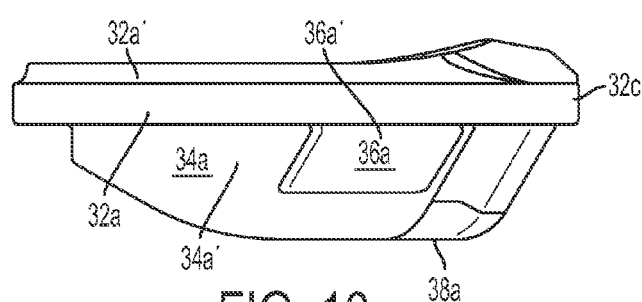
Figure 11:
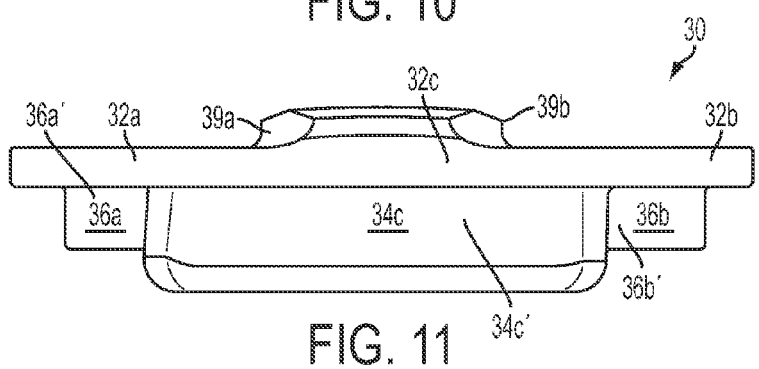
Figure 12:
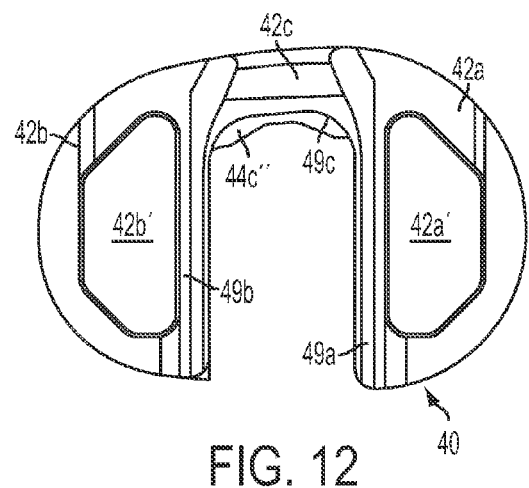
FIGS. 12-15 illustrate a tibial base member according to a fourth embodiment.
Figure 13:
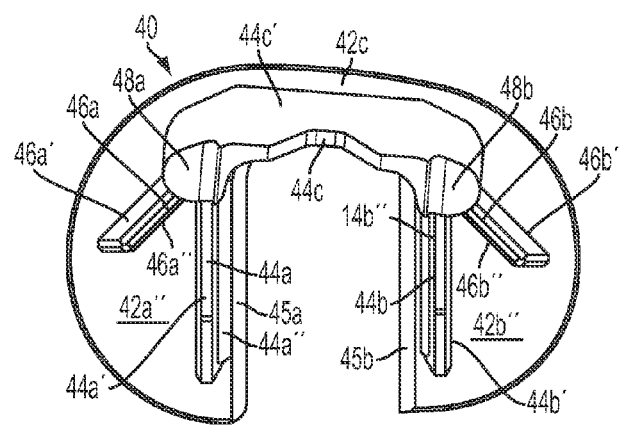

As shown best in FIG. 35, superior-inferior height of the medial 84a and lateral 84b keel portions may generally decrease posteriorly to provide, in some embodiments, an optimized stress distribution and enough flexibility to prevent stress shielding. Moreover, keel portions 84a, 84b, 84c are generally angled in an anterior-posterior direction to provide support for medial 82a and lateral 82b portions of tibial base member 80. The angles and positioning of the keel portions 84a, 84b, 84c in both anterior-posterior and medial-lateral directions, in at least some embodiments, provide at least some degree of balance between: (a) supporting the central portion of each side portion 82a, 82b of the base member 80 during posterior loading of the base member 80; and (b) supporting edge portions of the medial and lateral portions 82a, 82b of the base member 80 during extreme edge loading at either the medial or lateral side of the base member 80. Moreover, the angles and positioning of the keel portions 84a, 84b, 84c can be designed to support such loads without necessitating a relatively wide anterior keel portion 84c, which could otherwise interfere with or protrude through the anterior cortex of the tibia 220 if made too wide. While the illustrations show the lower edge of the angled side keel portions 84a, 84b to be a straight edge, the shape of the distal edges may be curved or stepped in other embodiments such that the depth change of the medial and lateral keel portions 84a, 84b is a non-linear function with respect to posterior distance. Curved or stepped lower edges of side keel portions 84a, 84b (such as shown in the embodiment of FIG. 7) may allow better optimization of stress distributions within the tibial base member 80.

In some embodiments, such as the one illustrated in FIGS. 30-35 and 47, medial and lateral keel portions 84a, 84b may have one or more reinforcing webs 85a, 85b connecting peripheral cement rails 87a, 87b to the keel portions 84a, 84b (FIGS. 34-35). The reinforcement webs 85a, 85b may be strategically located so as to pass under any high stress points, such as at the corners of locking portions 82a', 82b' (FIGS. 32-33), which may be, for example, cutout recesses or pockets located on the proximal side of medial 82a and lateral 84a portions and that are configured to receive medial and lateral tibial inserts 110, 120 (discussed below). Although not illustrated, webs 85a, 85b may also be provided in the top pocket portions of the locking portions 82a', 82b', so long as inferior sides of the tibial inserts 110, 120 are also provided with complementary recesses to afford clearance for the webs 85a, 85b.

As shown in FIG. 34, rounded corners, radiuses, or filets 81a, 81b may be provided between eminence lip portions 89a, 89b, 89c of the tibial base member 80 to form the inside surfaces of the cutout portion configured to receive the tibial eminence. Said rounded corners, radiuses, or filets 81a, 81b may, in some embodiments, reduce the stress risers at those areas thereby overcoming the failures associated with the sharp corners typical of prior bi-cruciate retaining designs. The amount of rounding of the corners, in some embodiments, may avoid causing interference between the implant and the anterior cruciate ligament attachment point on the tibia 220.

Moreover, as with other embodiments, heightened walls or eminence lip portions 89a, 89b, 89c along the medial and lateral sides of the eminence cutout area (see, e.g. FIG. 33) may be provided to increase the overall strength of the base member 80 along inside edges. This added strength may facilitate, in at least some embodiments, resisting stresses and other forces on the base member 80 when loaded posteriorly. Moreover, eminence lip portions 89a, 89b, 89c, when combined with undersurfaces 82a", 82b", may facilitate the creation of a cement mantle and allow the cement mantle to grow along the base of a prepared tibial eminence. This extra cement along the base corners and sides of the tibial eminence and between the eminence and base member 80 may generally improve the resistance to eminence fracture. Heightened walls or eminence lip portions 89a, 89b, 89c may further serve to isolate tibial inserts from both the cement mantle and the vertical walls of the prepared tibial eminence, and also serve as buttresses for stabilization of the tibial inserts in the medial-lateral direction.

The anterior connecting portion 82c may define a generally trapezoidal sagittal shape, both in sagittal cross section (see, e.g. FIG. 35) and when viewed superiorly (see, e.g. FIG. 33). In this embodiment, anterior portion 82c is wider (medial-lateral dimension) towards the posterior. Such geometries may, in some embodiments, assist in limiting stress concentration in the anterior portion 82c and promote a more even distribution of stress by encouraging the stresses to flow more anteriorly to regions where there are fewer stress risers.

In this particular embodiment, the anterior connecting portion 82c of the tibial base member 80 is sloped so as to be thicker (superior-inferior dimension) towards the posterior, which, in some embodiments, may increase strength of the base member 80 proximate the edge of the eminence cutout, while still providing more flexibility on anterior portions of the base member 80 for even stress distribution when the base member 80 is loaded posteriorly. For example, if one of the medial portion 82a or lateral portion 82b is loaded posteriorly more than the other (e.g., in deep flexion), then torsional forces may arise in the anterior portion 82c. In such situations, the flexibility created from a thinner anterior part of the anterior portion 82c more evenly distributes torsional stresses, and the thicker posterior portion of the anterior portion 82c and raised anterior eminence lip 89c provides extra strength and rigidity.

Figure 41:
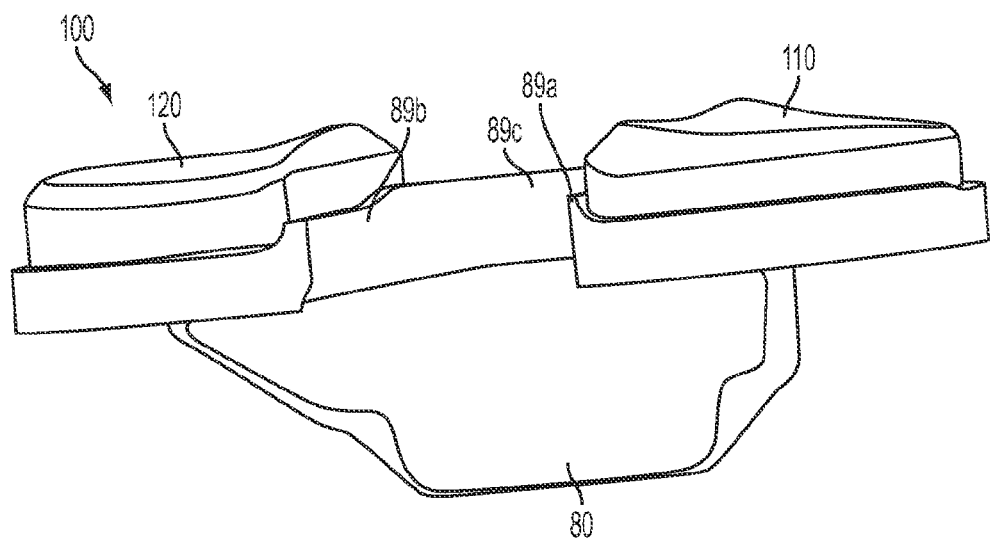
Figure 42:
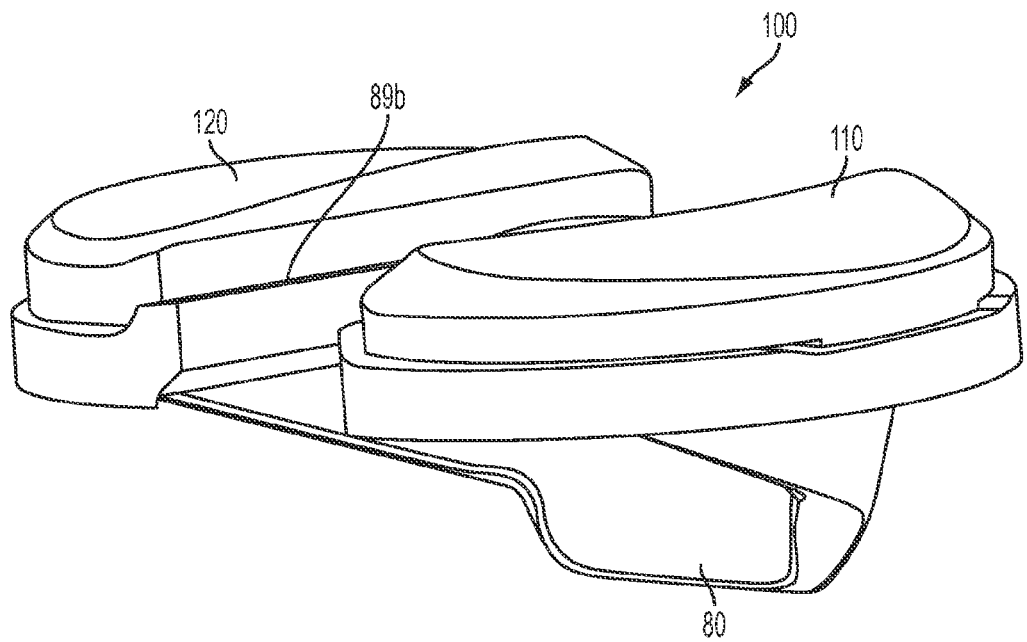
Figure 43:
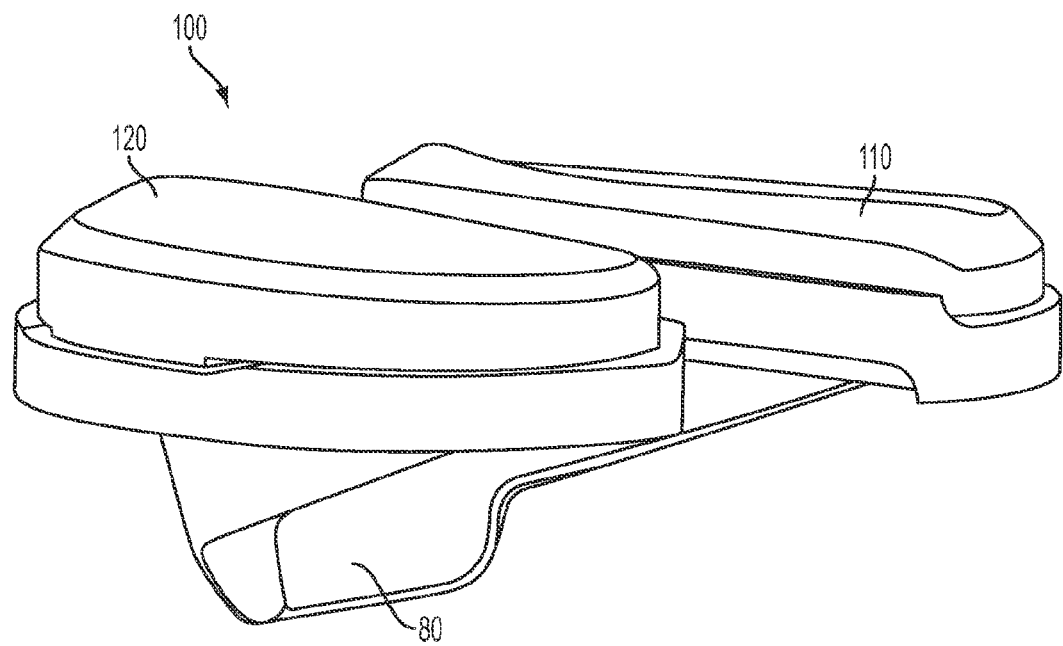
Figure 44:
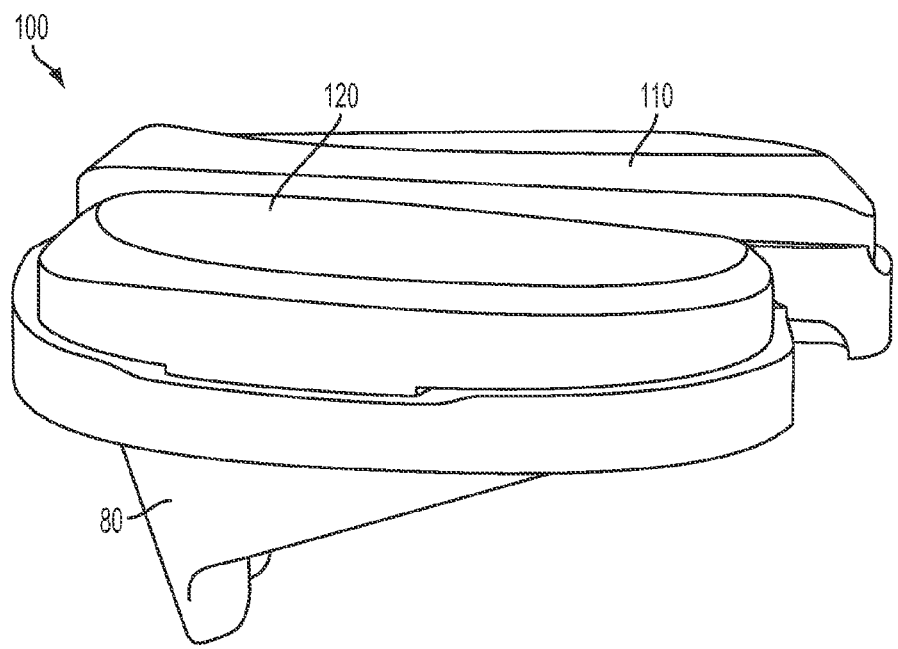
Figure 45:
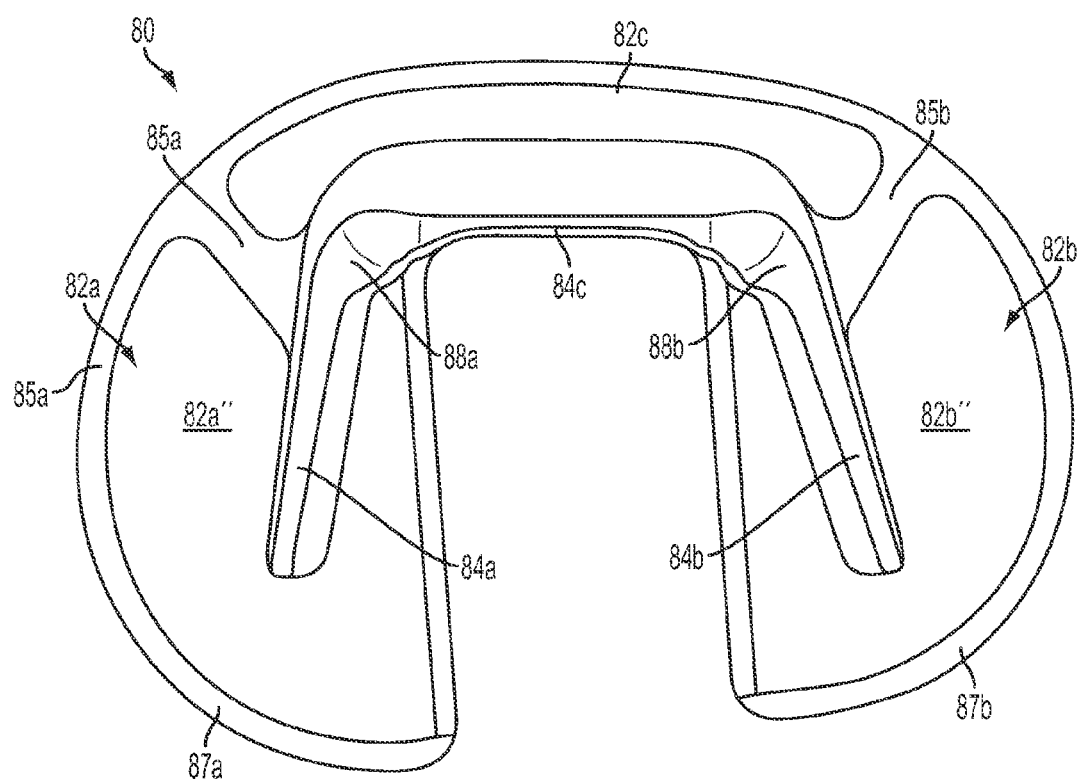
Figure 46:
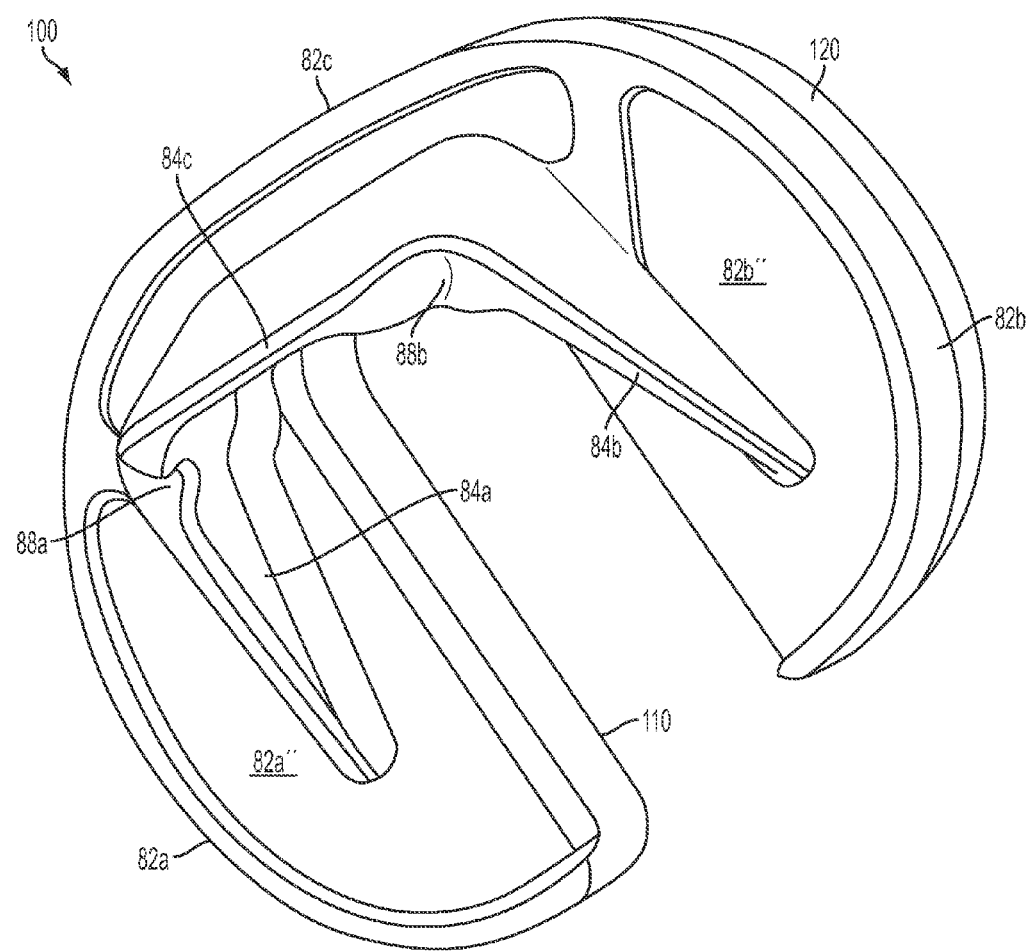
Figure 47:
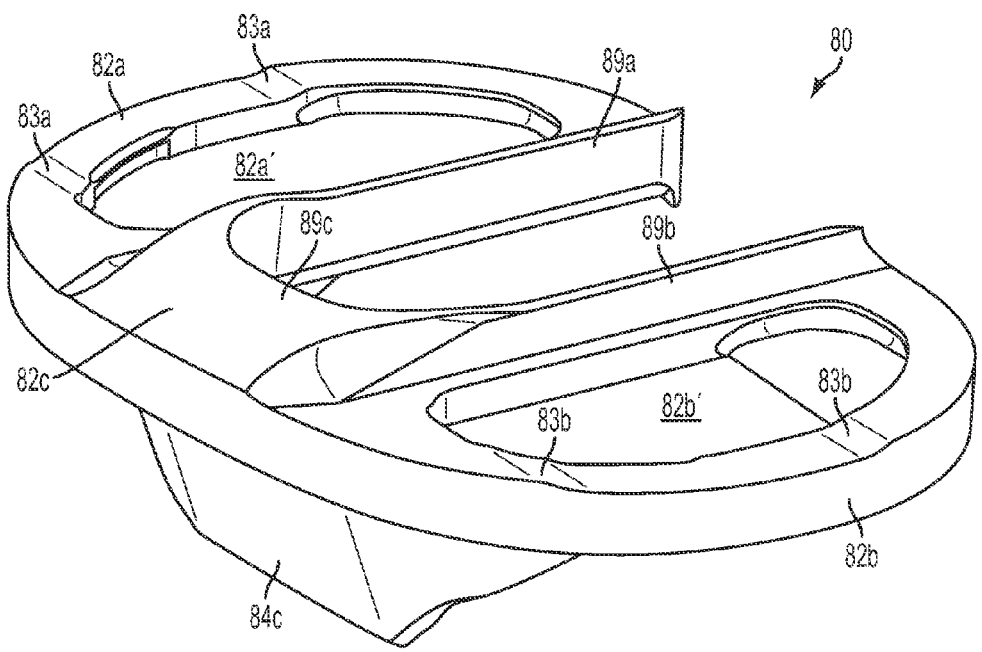
Figure 48:
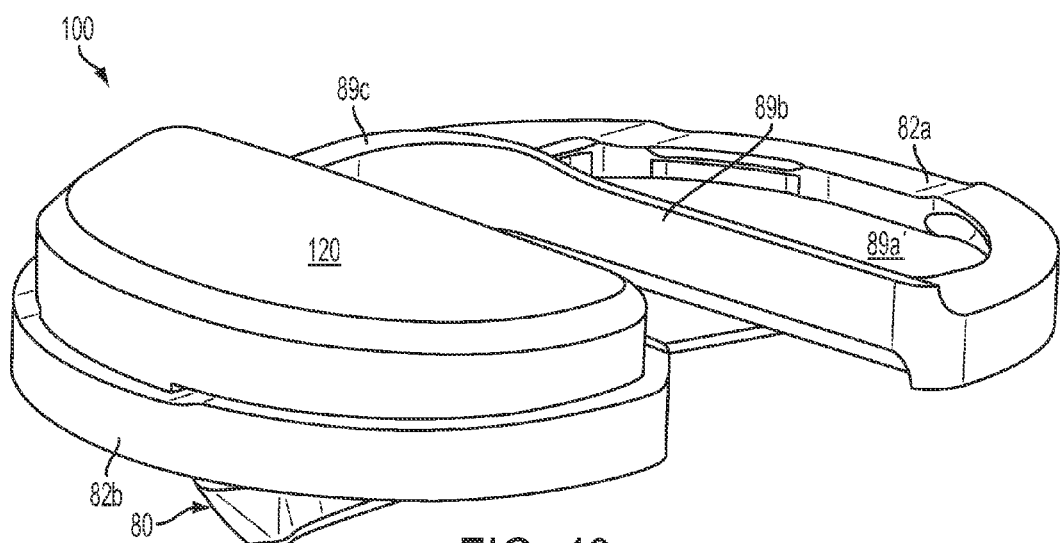
FIG. 48 illustrates a step of assembling the bicruciate-retaining tibial prosthesis shown in FIGS. 38-46.
Figure 49:
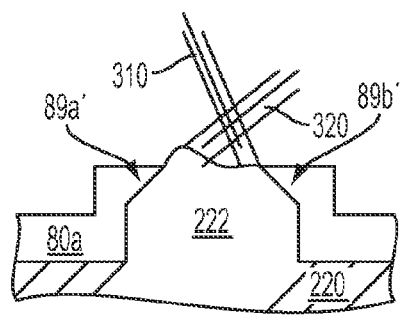
FIGS. 49-52 are frontal coronal cross-sectional views schematically illustrating mating geometries between a tibial base member and a tibial eminence according to various embodiments.
Figure 50:
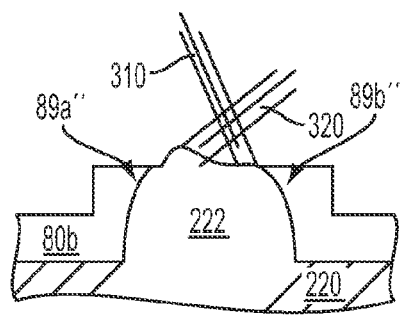
Figure 51:
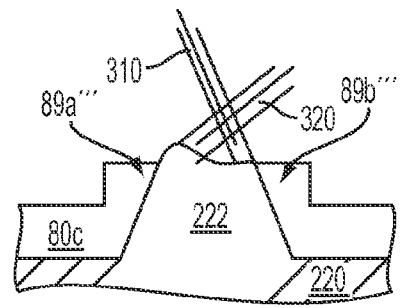
Figure 52:
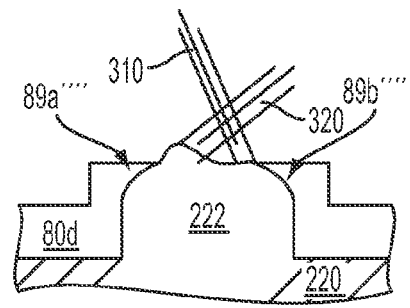

FIG. 41 shows the tibial base member 80 with tibial inserts 110 and 120 mounted thereon. As shown in FIG. 41, the transition from the thicker lip portion 89c of the anterior portion 82c to the more recessed medial 89a and lateral 89b eminence lips provides additional material at the high stress area at the corners of the eminence cutout portion of the base member 80. Therefore, the medial 89a and lateral 89b lips can be shorter than the anterior portion 82c and the anterior eminence lip 89c without adversely affecting the strength of the tibial base member 80. Moreover, reducing the height of the medial 89a and lateral 89b lips could prevent contact between the tops of the lips 89a, 89b and the femoral component 400, especially in instances where thin polymeric inserts 110, 120 are utilized.

Returning to FIGS. 32-33, the upper or proximal side of tibial base member 80 may include a medial plateau locking portion 82a' and a lateral plateau locking portion 82b' each having a lock detail that serves to secure a polymeric tibial insert. Such lock details may include, for instance, one or more undercuts, dovetail joints, male-female connections, grooves, ridges, press-fit connections, barbs, latches, pegs, magnets, and other art-recognized connection means. Lock details may allow moderate rotational or translational movement of the inserts for mobile bearing applications as will be discussed below. FIGS. 38-46 illustrate tibial base member 80 assembled with medial articulating insert 110 and lateral articulating insert 120. In some embodiments, the peripheries of the tibial base member 80 and/or tibial inserts 110, 120 align closely with the periphery of the resected proximal tibia.

While not shown, the upper surfaces of the tibial base member 80 may be configured for use with mobile bearings. In other words, the medial and lateral locking portions, in certain embodiments, may be provided with a means for securing the medial and lateral inserts to the base member, while allowing some finite rotational movement of the inserts. Such means may include, for instance, a male to female connection such as a peg-in-hole configuration or a circular undercut that locks the inserts in 5 degrees of freedom, while still allowing controlled rotation of the inserts relative to the base member. Other means may be provided, such as tracks and followers, which allow controlled translation of the inserts in any one or more of the anterior-posterior and medial-lateral directions.

Figure 36:
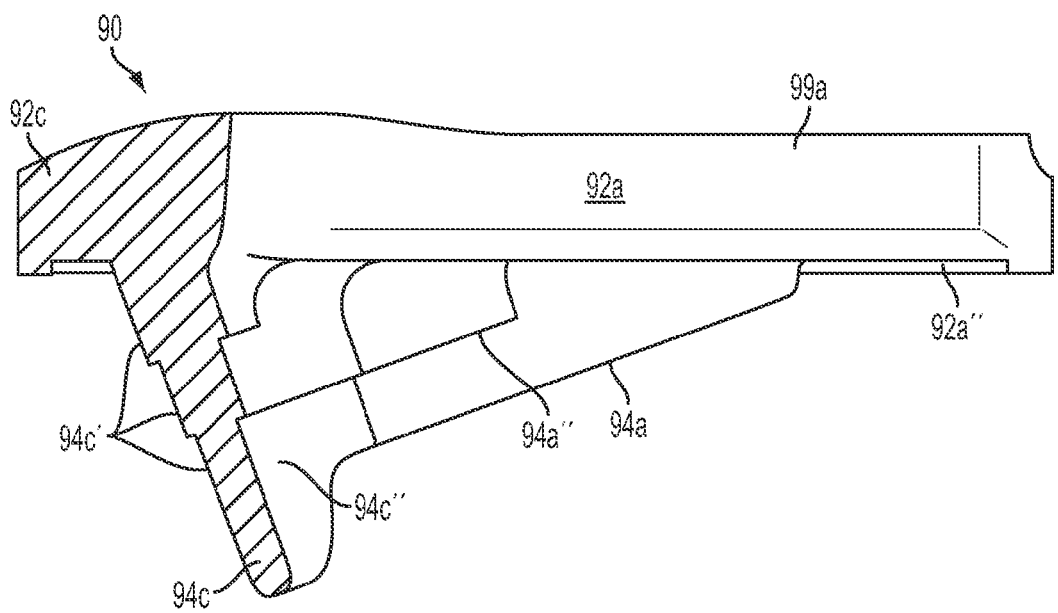
FIGS. 36 and 37 illustrate a tibial base member according to a ninth embodiment, which includes steps, textures, or jagged features provided on the keel portions.
Figure 37:
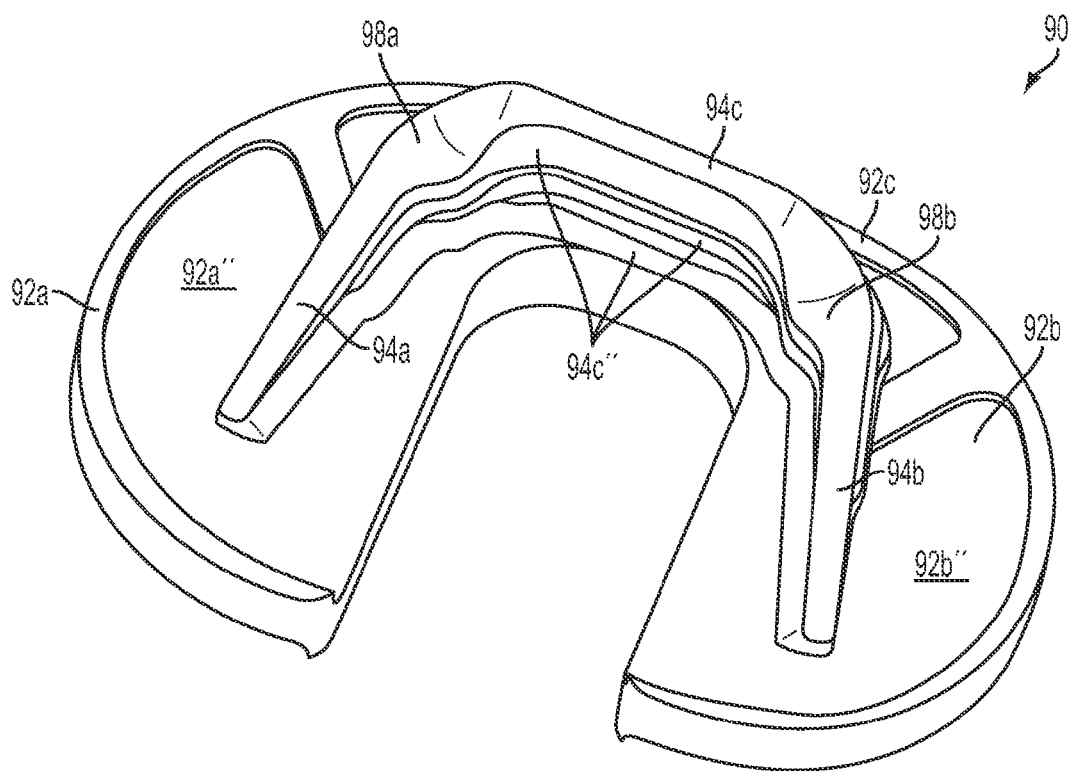
Figure 38:
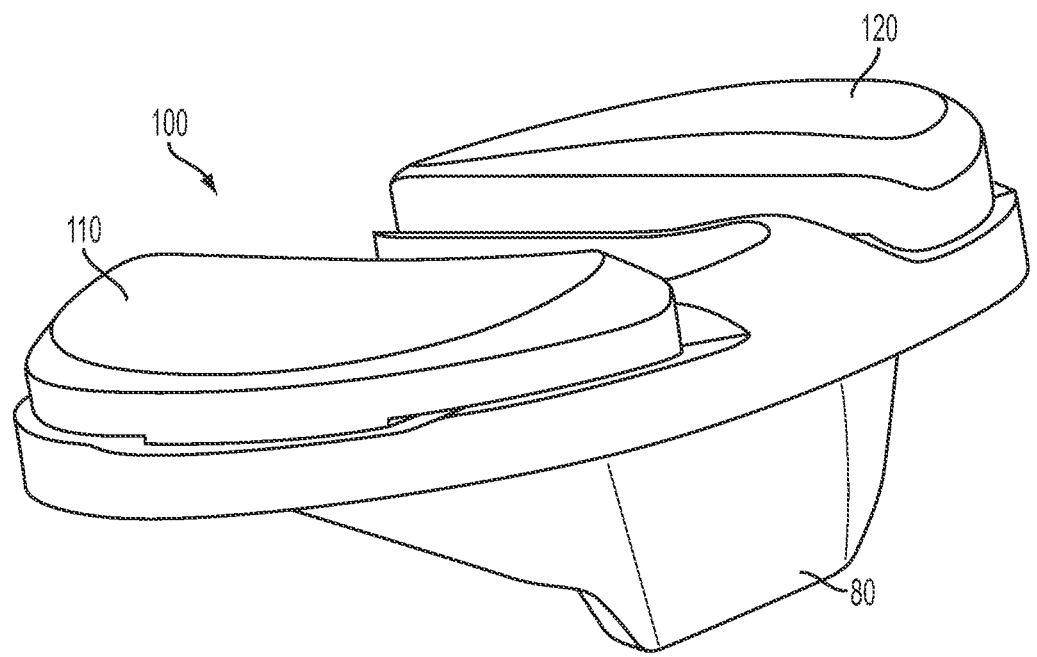
FIGS. 38-46 illustrate the tibial base member of FIGS. 30-35, and 47, shown assembled with medial and lateral articulating tibial inserts.
Figure 39:
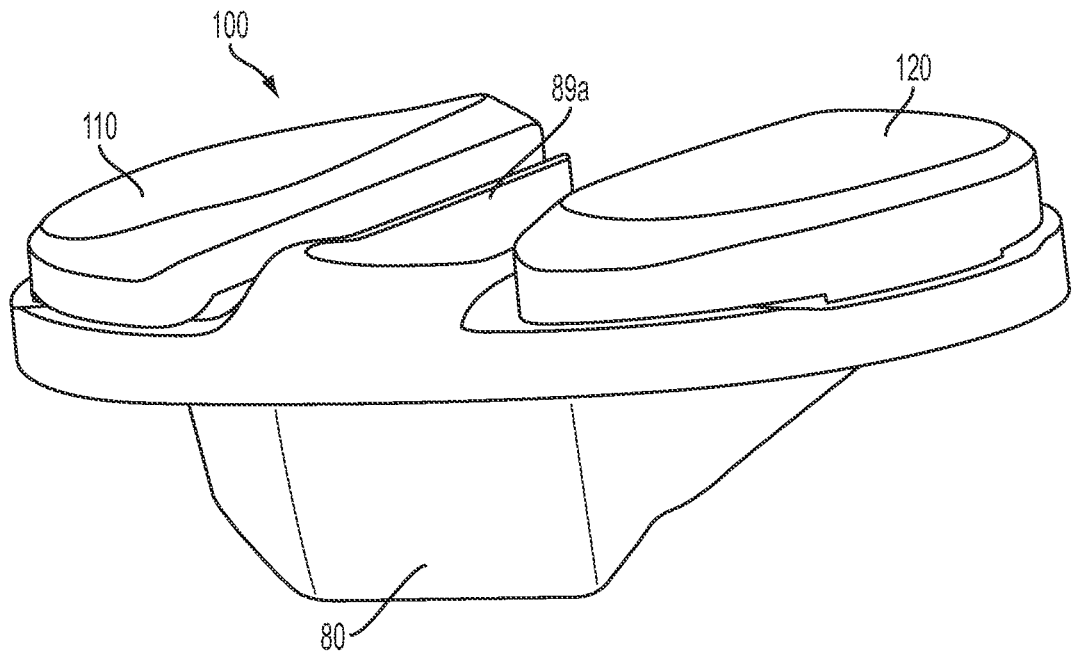
Figure 40:
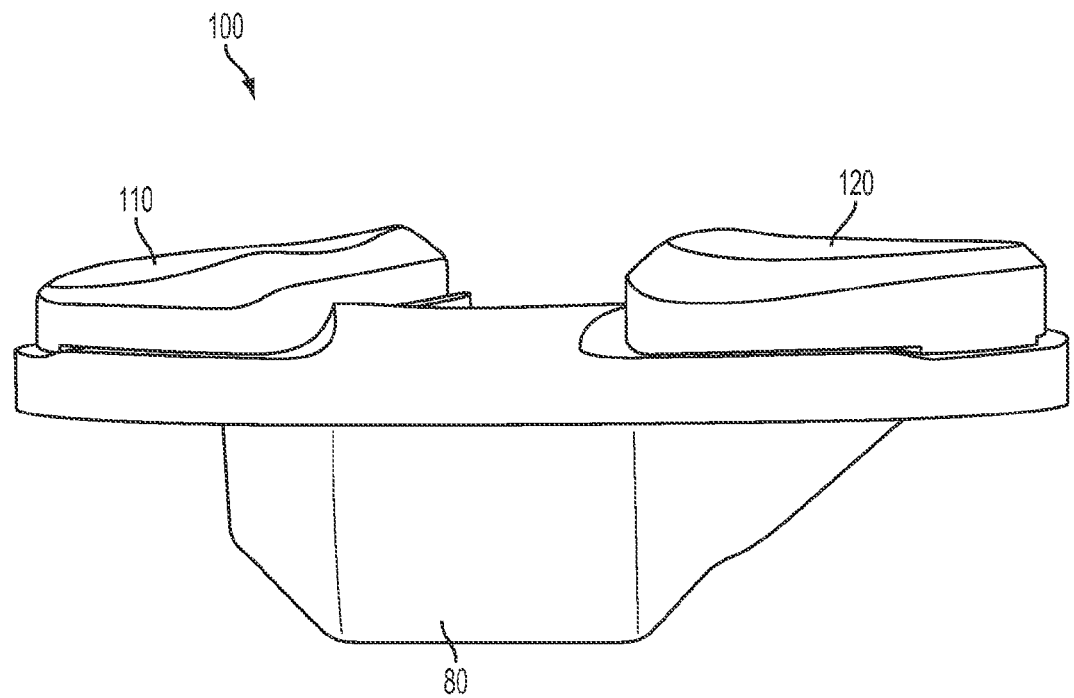

FIGS. 36-37 illustrate a ninth embodiment of a tibial base plate, tibial base plate 90. As with some of the earlier embodiments described herein, the tibial base plate 90 includes keel portions that are swept back. In this particular embodiment, the keel portions 94a, 94b, 94c are stepped to increase bone compression during implant insertion and to create zones of increased stress at the corners of the steps. Base member 90 having stepped keel portions 94a, 94b, 94c may also encourage better fixation for both cemented and cementless applications. Instrumentation used to prepare the tibia to receive a tibial base member may include, in some embodiments, a punch that is or is not stepped to provide more or less interference and press fit engagement.

Figure 97:
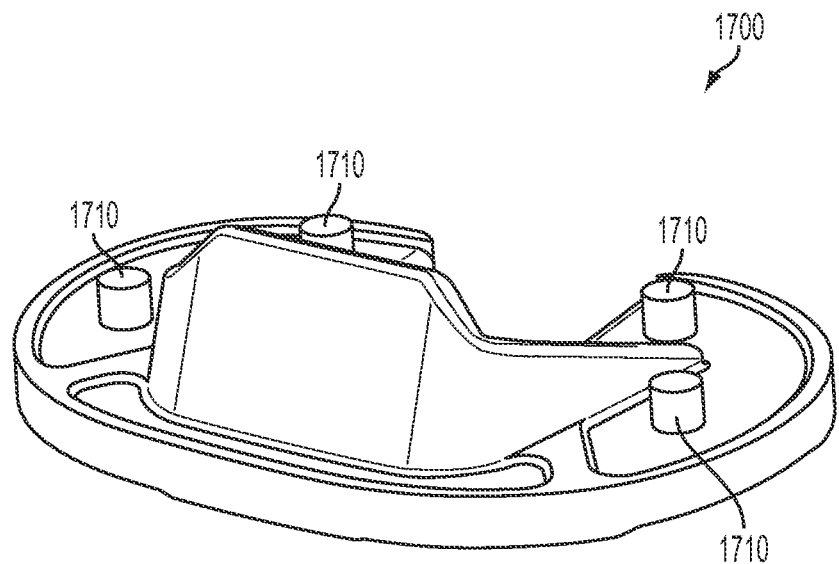
FIGS. 97-98 are bottom isometric views of a tibial base member according to a tenth embodiment that includes one or more pegs.
Figure 98:
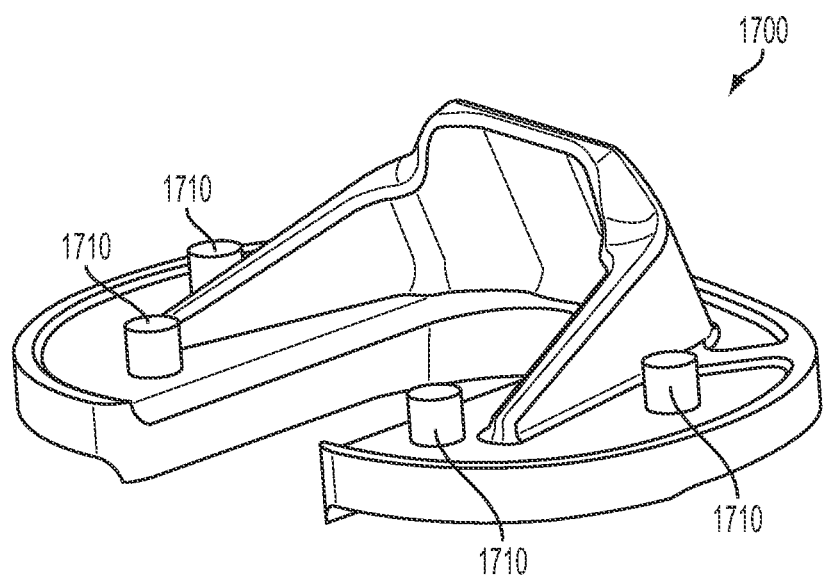
Figure 99:
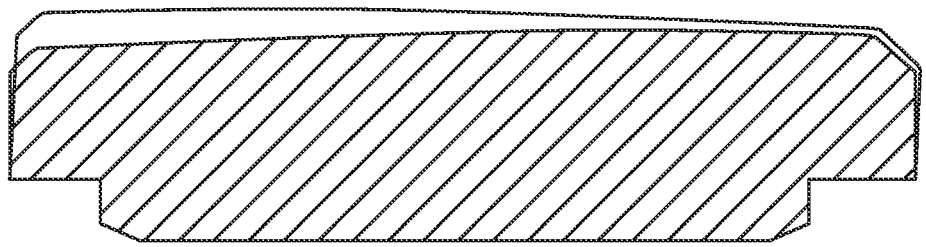
FIG. 99 is a sagittal cross-sectional view of a lateral insert according to an embodiment.
Figure 100:
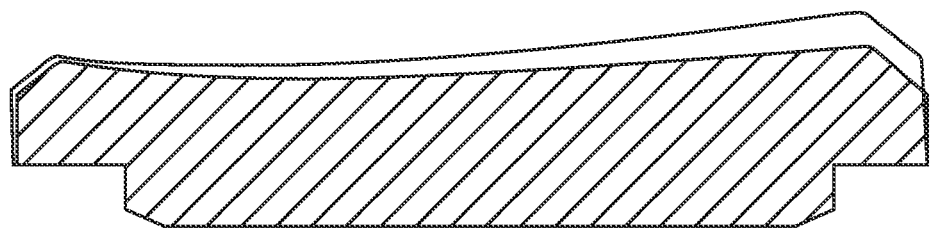
FIG. 100 is a sagittal cross-sectional view of a medial insert according to an embodiment.

FIGS. 97-98 illustrate a tenth embodiment of a tibial base plate, tibial base plate 1700. As with some of the earlier embodiments described herein, the tibial base plate 1700 includes keel portions that are swept back. This particular embodiment also includes pegs 1710 or other suitable structure for providing increased fixation with the prepared tibia 220.

Figure 53:
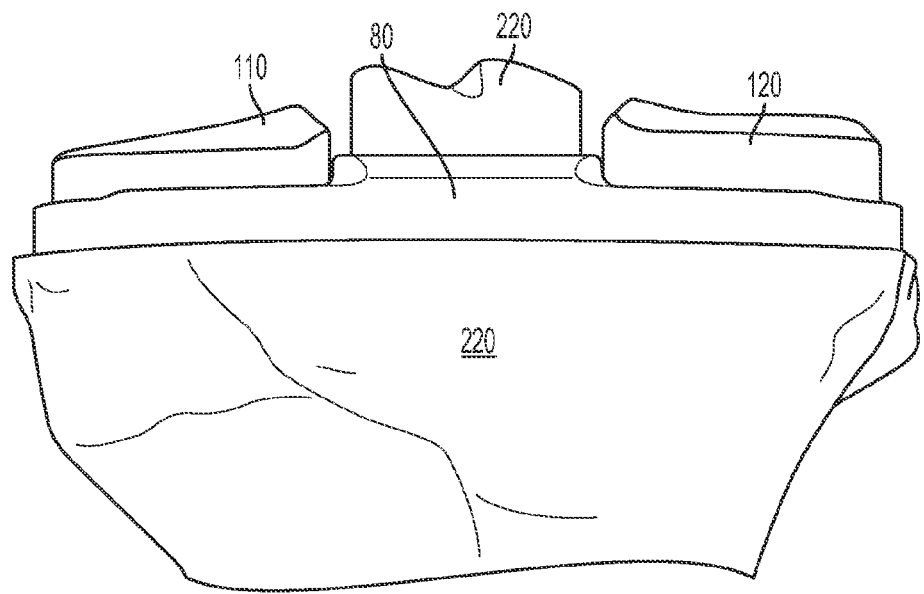
FIG. 53 is a frontal coronal view of a bicruciate-retaining tibial prosthesis shown implanted on a proximal tibia.
Figure 54:
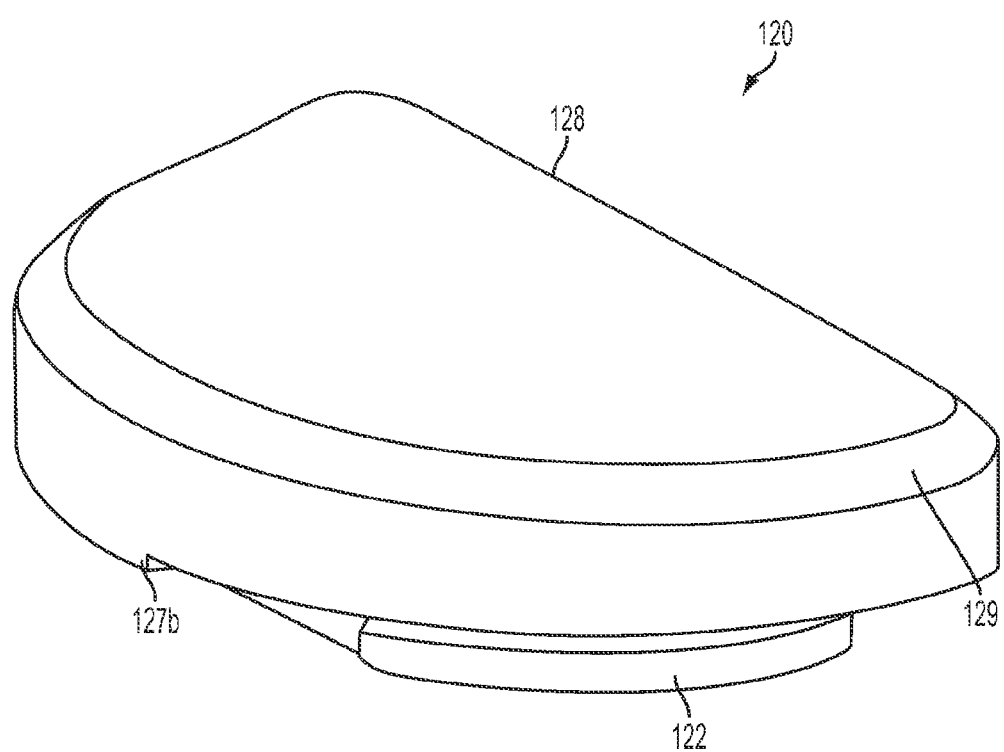
FIGS. 54 and 55 illustrate posterior views of a lateral tibial insert.
Figure 55:
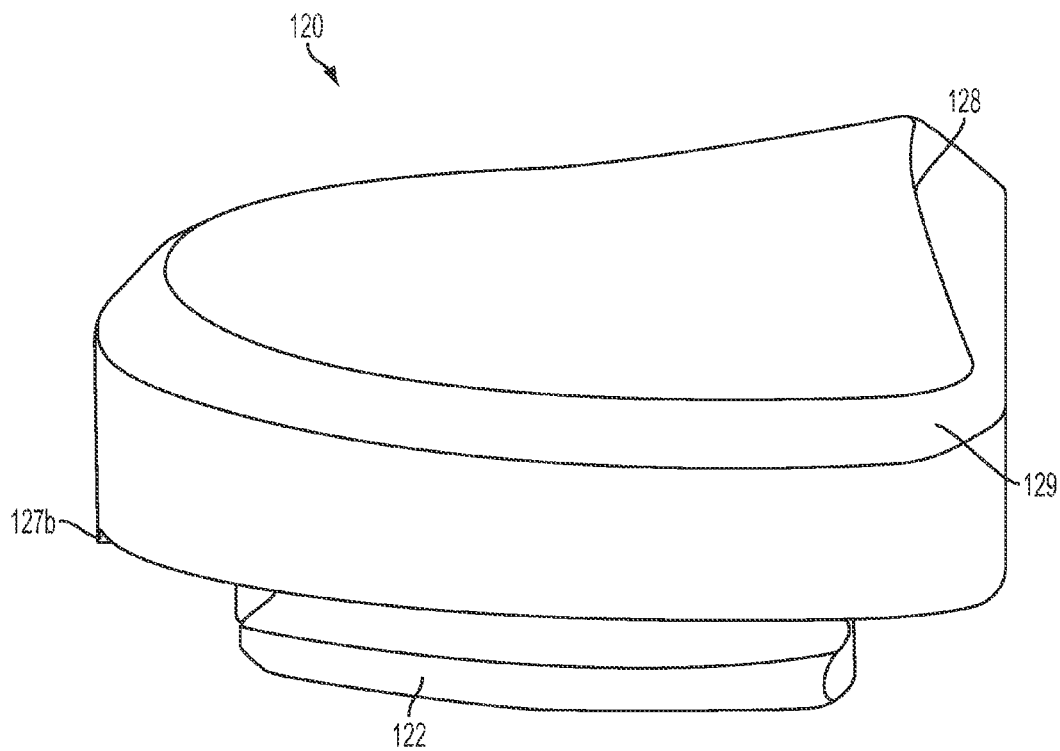

FIGS. 49-52 are front coronal cross-sectional views showing the mating geometries between tibial base members 80a-80d, such base members having medial eminence lips 89a-89a" and a lateral eminence lips 89b'-89b"', respectively, and a tibial eminence 222 of a prepared tibia 220. As shown in the figures, one or both of anterior cruciate ligament (ACL) 310 and posterior cruciate ligament (PLC) 320 are preserved. FIG. 53 is a frontal coronal view of a tibial base member 80 assembled with inserts 110, 120 with respect to a prepared tibia 220 and the tibial eminence 222.

In some embodiments, the relative anterior keel portion length and angle can be optimized based on data collected. It has been found that given a fixed anterior keel portion length, increasing the angle of the anterior keel portion from vertical generally increases the amount that the anterior keel portion undercuts the anterior tibial eminence, and that too much angle can reduce strength of the base member. If too much of the anterior keel portion undercuts the eminence, the eminence may also be compromised. Some of the embodiments of the tibial base member were achieved through a combination of optimizing the shapes to distribute stress more efficiently throughout the base member, refining the target strength by analyzing previous tibial base member designs which were known to fracture, and running computer simulations in an iterative fashion. Input received during cadaver labs was used to identify the amount of and areas for bone removal which were acceptable from an anatomical perspective, and such information was also used to determine the optimal number, geometries, and orientation of keel portions for increased strength and improved initial fixation in various embodiments. The inventors took into consideration manufacturing the same tibial base member design from various materials with high and low fatigue resistance in order to increase the robustness of the design regardless of material strength and properties.

The particular shape of the entire keel selected, combined with the angle of the anterior keel portion, which is in some embodiments is approximately 70 degrees, essentially creates a "self-anchoring" feature. In other words, since the anterior keel portion undercuts the cancellous bone (relative to the proximal tibial plateau), it provides hold down forces to counteract pull-out forces.

Also disclosed are methods of implanting a tibial prosthesis. The method includes the steps of determining a resection depth, determining a preferred spatial orientation for the prosthesis, resecting the medial and lateral tibial plateau bone portions without compromising the tibial eminence and ACL/PCL attached thereto, broaching necessary receiving portions for acceptance of one or more fixation features provided on the underside of the tibial prosthesis, and installing the tibial prosthesis using cemented or cementless techniques.

2. Tibial Inserts

The above described and other embodiments provide improved tibial inserts, such as medial insert 110 and lateral insert 120 illustrated in FIGS. 38-44 as assembled with base member 80. In some embodiments, medial insert 110 is thinner than the lateral insert 120 so as to match the varus joint line present on a femoral component. In some embodiments, for instance, the lateral insert 120 may be approximately 2.5 mm thicker than the medial insert 120, in order to create a 3° varus joint line that matches a 3° varus joint line of the femoral component. The tibial articular geometry of some embodiments generally includes a concave medial portion on the medial insert 110 and a convex lateral portion on the lateral insert 120. A coronal conformity may be present on inner portions of one or both of the inserts 110, 120. This coronal conformity, for instance, may comprise a mesial lip, which, as described further below, may vary in height along the anterior-posterior direction.

FIGS. 54-58 show various views of an embodiment of a lateral insert 120, while FIGS. 59-63 show various views of an embodiment of a medial insert 110.

Figure 56:
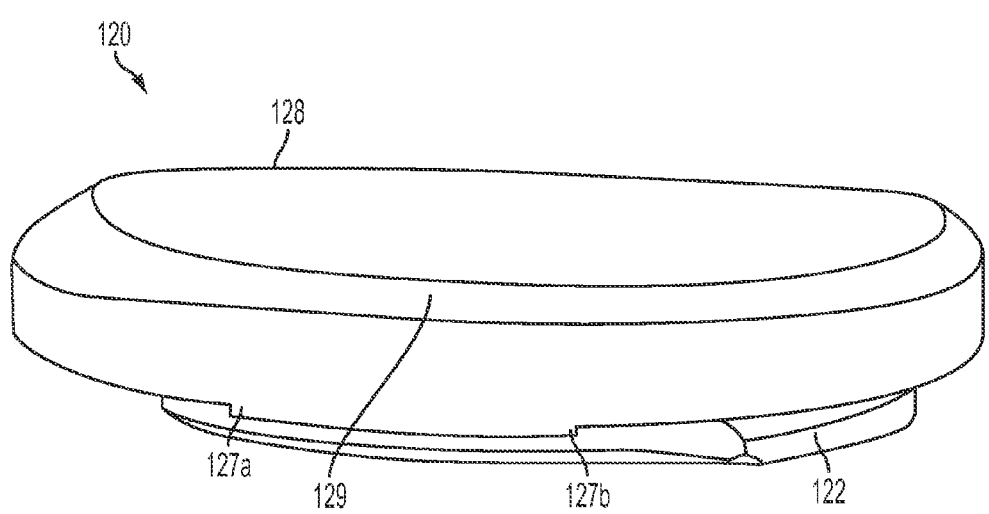
FIG. 56 illustrates a lateral sagittal view of the lateral insert of FIGS. 54 and 55.
Figure 57:
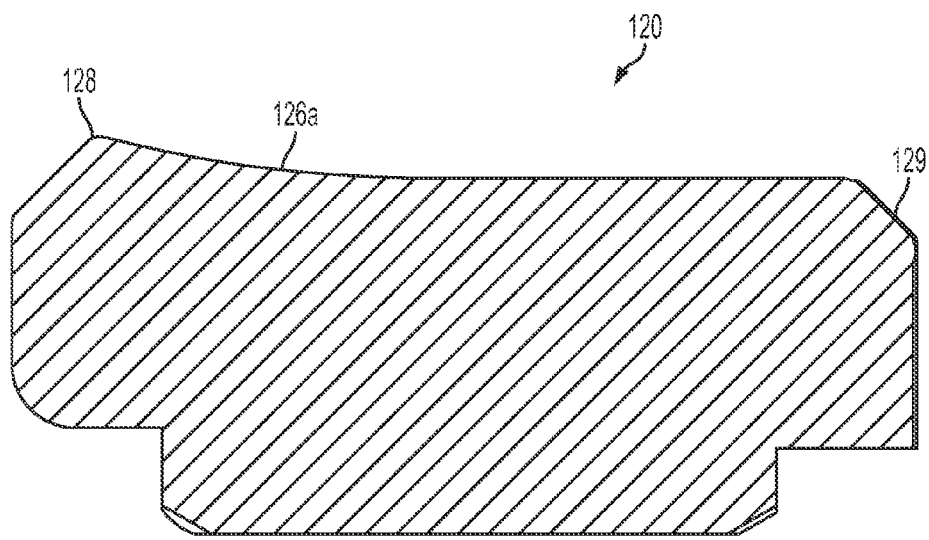
FIG. 57 shows a coronal cross-sectional view of the lateral insert of FIGS. 54-56 when viewed from the anterior side.
Figure 58:
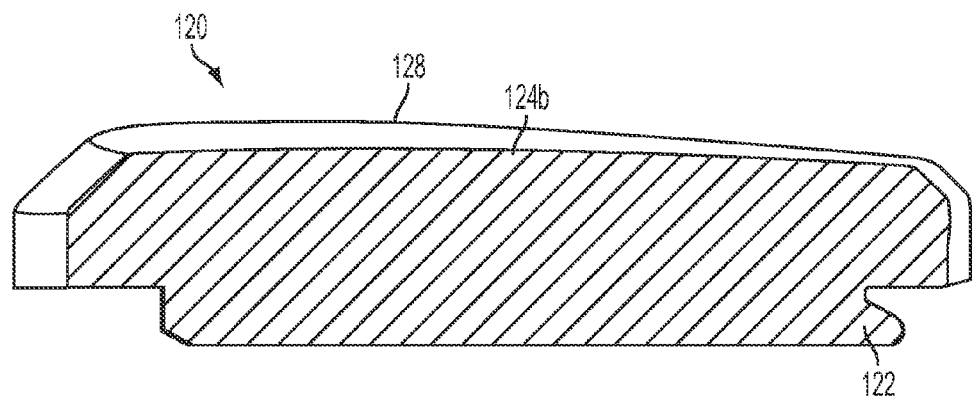
FIG. 58 shows a sagittal cross-sectional view of the lateral insert when viewed from the lateral side.
Figure 59:
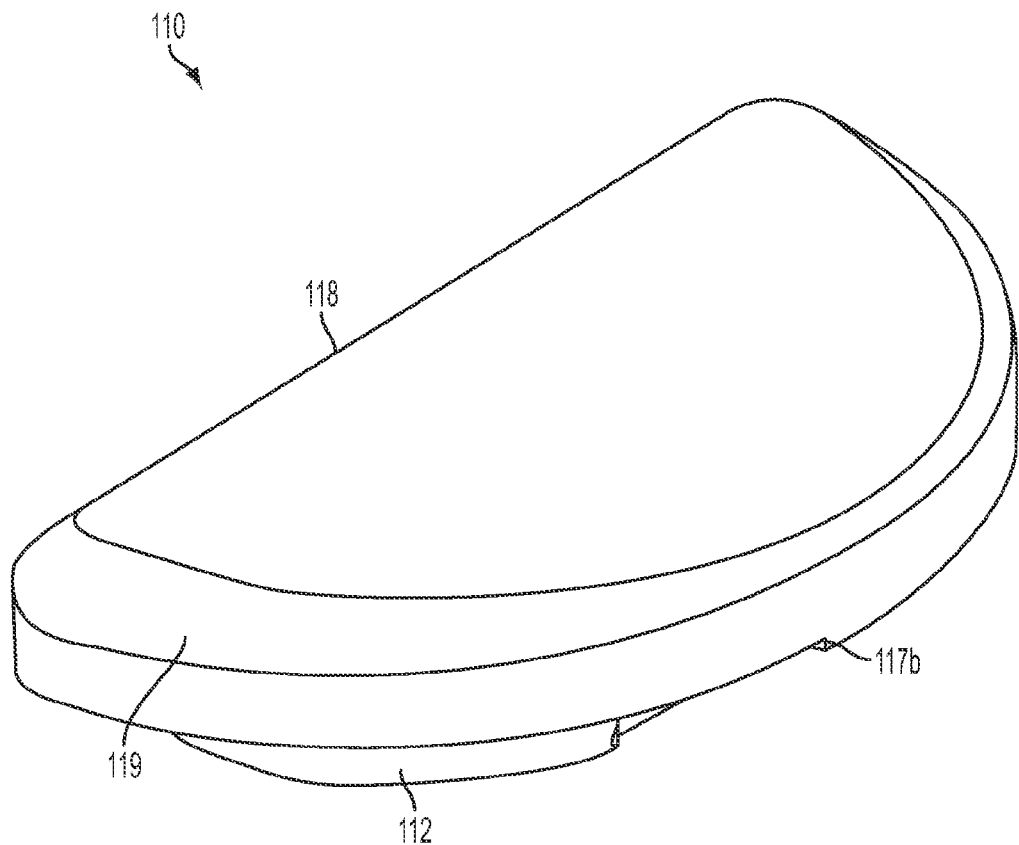
FIGS. 59 and 61 are posterior views of a medial tibial insert.

The lateral insert 120 of FIGS. 54-58 defines a superior articulation surface, defining several different contours in various planes. FIGS. 57 and 58 are cross sections of the lateral insert 120 in certain coronal (FIG. 57) and sagittal (FIG. 58) planes. FIG. 57 illustrates a contour 126a defined by a relatively anterior, coronal cross section of lateral insert 120. FIG. 58 illustrates a contour 124b defined by a relatively middle, sagittal cross section of lateral insert 120. FIGS. 90a-e are a series of sagittal cross sections of an embodiment of a left, lateral insert illustrating the contours of that insert from relatively mesial (e.g. FIG. 90a) to relatively outer (e.g. FIG. 90e) portions of the insert. FIGS. 91a-k are a series of coronal cross sections of the same embodiment as shown in FIGS. 90a-e, the coronal cross sections of FIGS. 91a-k progressing from relatively anterior portions (e.g. FIG. 91a) to relatively posterior portions (e.g. FIG. 91k) of the insert.

As shown in the embodiments of FIGS. 54-58 and 90-91, and as described in further detail below, lateral insert 120 defines a mesial lip 128 and a circumferential chamfer 129. In some embodiments, at least some parts of the anterior portions and contours of the lateral insert 120 are relatively more conforming to a femoral condylar surface than other portions of the insert 120. As shown in FIG. 56, lateral insert 120 may also include peripheral steps 127a, 127b. FIGS. 56 and 58 illustrate a lock mechanism 122 used to secure lateral insert 120 to the tibial base member.

As shown in the embodiments of FIGS. 54-58 and 90-91, mesial lip 128 is raised relative to other portions and contours of the insert 120. As shown in FIG. 58, illustrating a sagittal cross section of the insert 120, such cross section taken through a middle portion of the insert 120, the raised mesial lip 128 extends from anterior to posterior portions of the insert 120. Mesial lip 128, in some embodiments, provides resistance to lateral femoral translation and prevents impingement between the femoral component 400 and the tibial eminence 222. The height of the mesial lip can be selected to provide a desired level of resistance, with a greater height providing more resistance. As shown in these embodiments, the height of the mesial lip relative to other portions of the insert 120 gradually decreases as it extends in an anterior to posterior direction. In the embodiments of FIGS. 54-58 and 90-91, outer side portions (near chamfer 129) of the lateral insert 120 are substantially flat and have little to no coronal conformity with the femoral condylar articulation surfaces. In some embodiments, the maximum height of the mesial lip 128 is between a range of approximately 0.025 inches and approximately 0.125 inches relative to the substantially flat outer side portions. In some embodiments, the maximum height of the mesial lip 128 is between approximately 0.035 inches and approximately 0.065 inches for the lateral insert 120.

Figure 60:
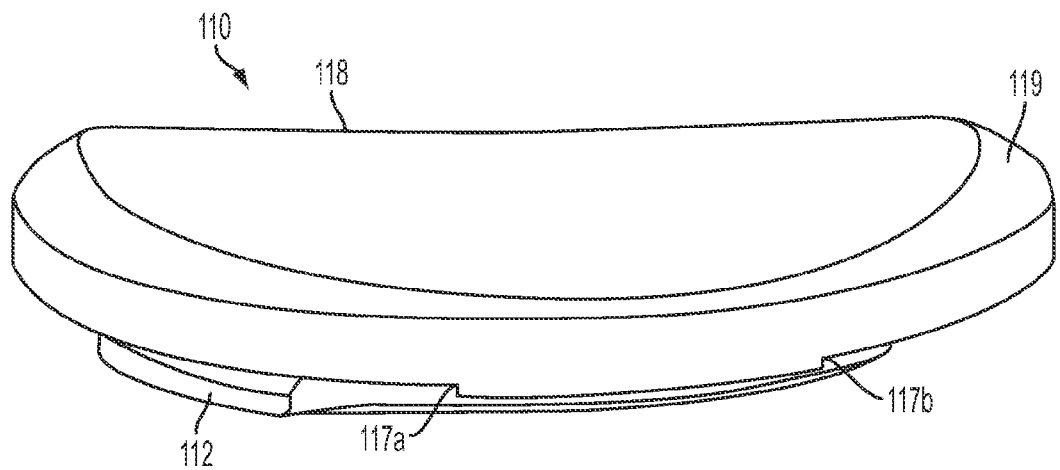
FIG. 60 is a medial sagittal view of the medial insert of FIGS. 59 and 61.
Figure 61:
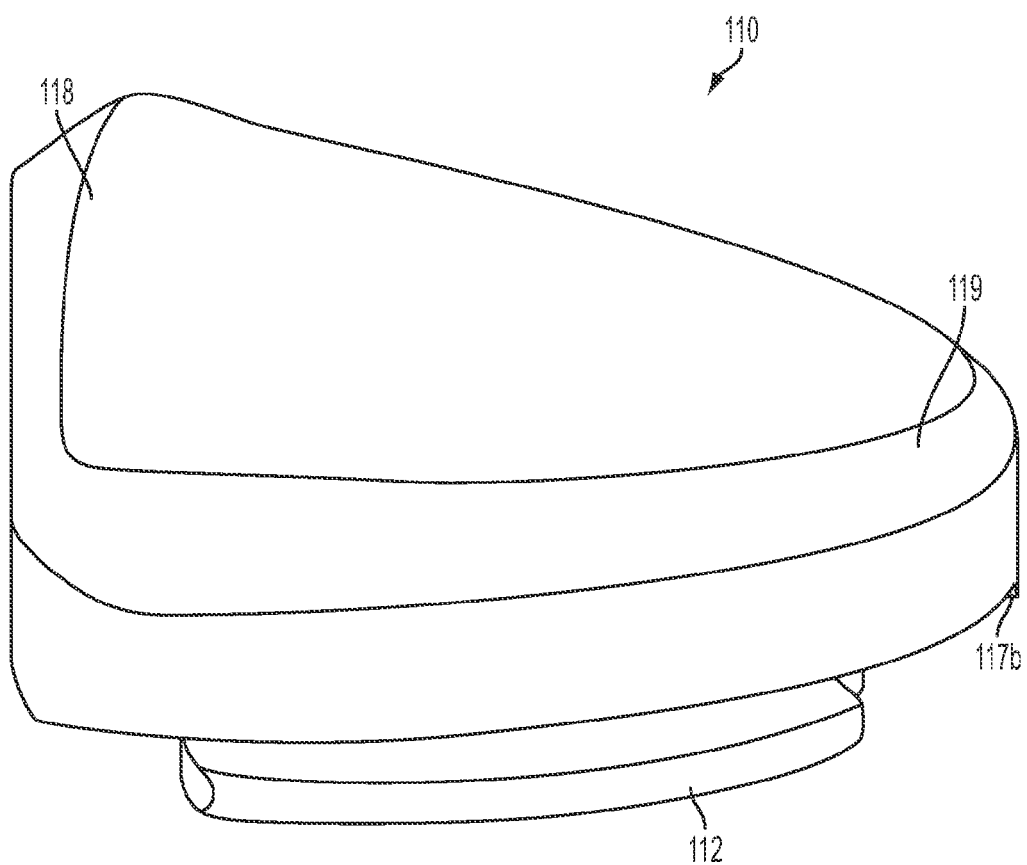
Figure 62:
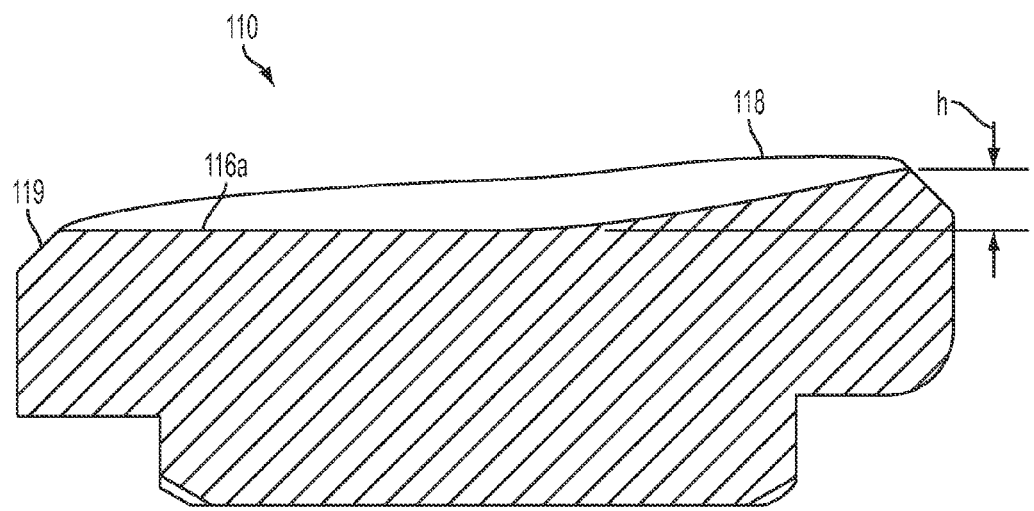
FIG. 62 shows a coronal cross-sectional view of the medial insert when viewed from the anterior side.
Figure 63:
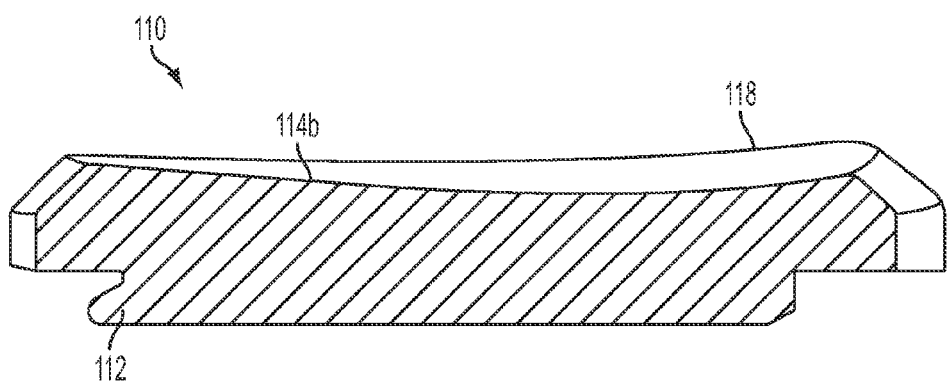
FIG. 63 shows a sagittal transverse cross-sectional view of the medial insert when viewed from the medial side.
Figure 93A:
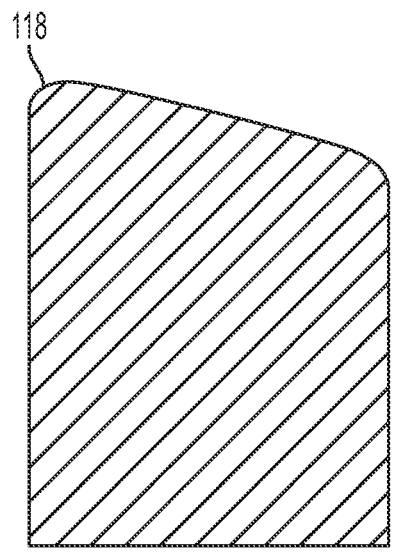
FIGS. 93*a*-93*m* show various coronal cross-sectional views of a medial insert when viewed from the posterior side.
Figure 93B:
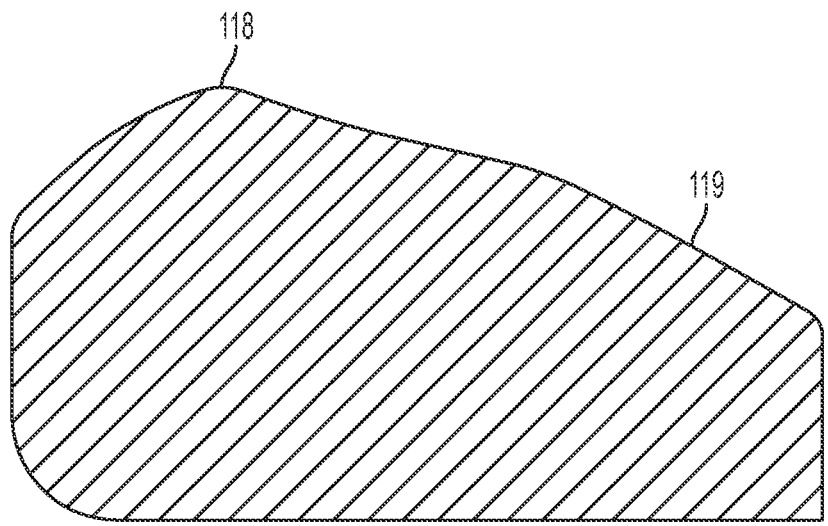
Figure 93C:
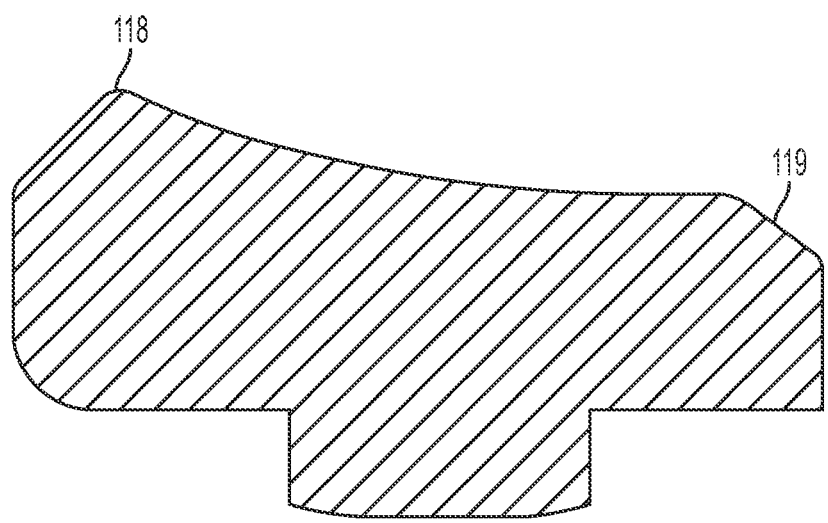
Figure 93D:
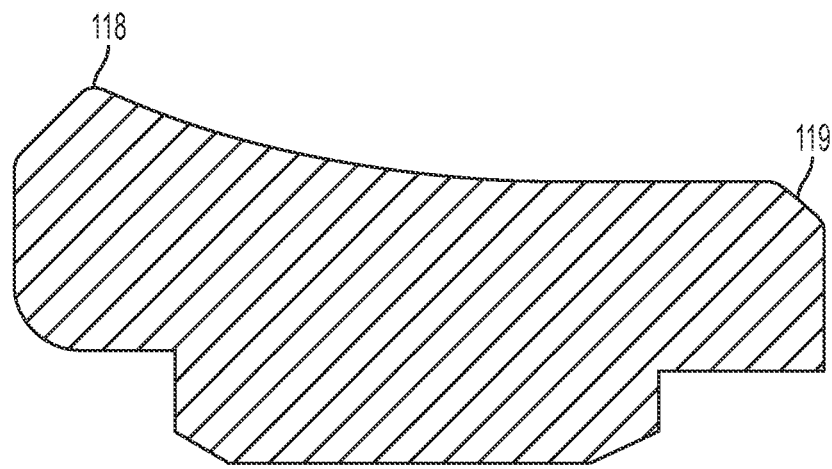
Figure 93E:
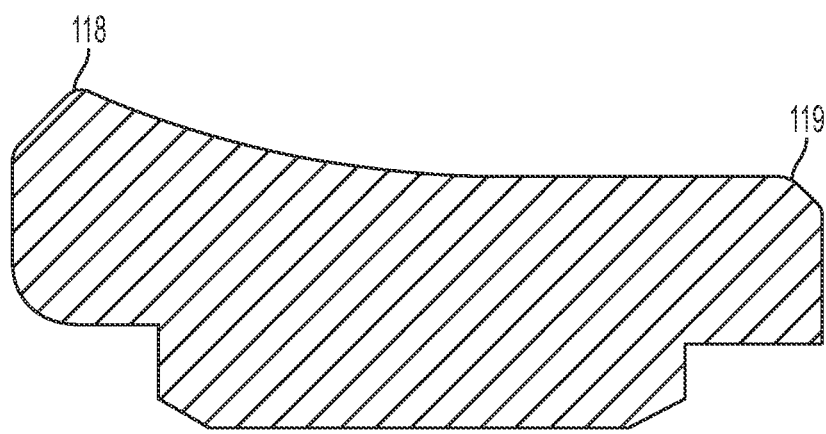
Figure 93F:
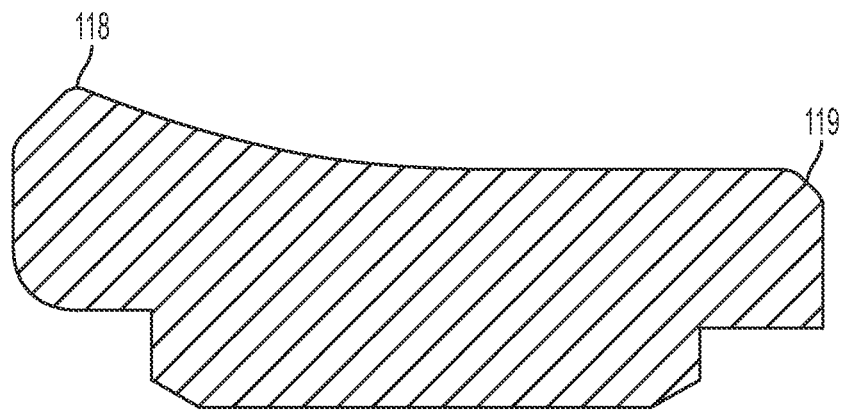
Figure 93G:
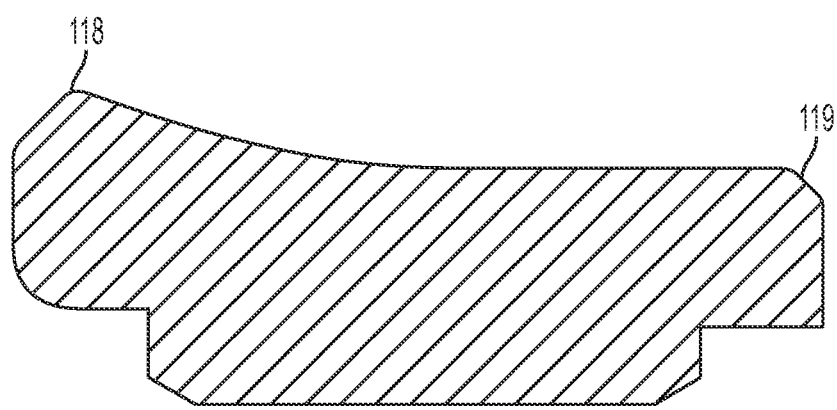
Figure 93H:
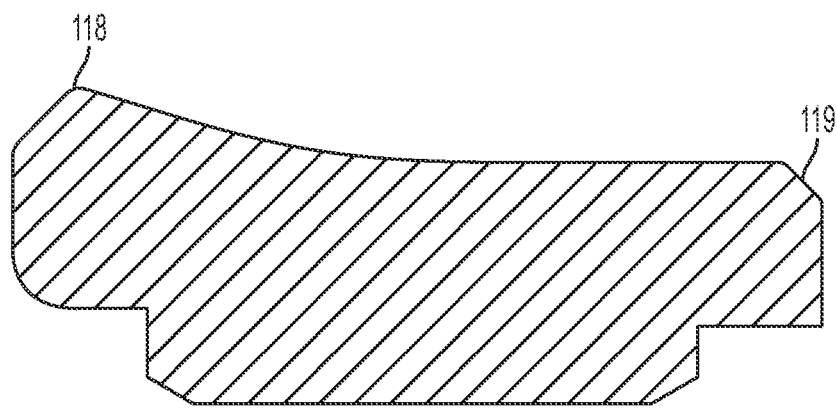
Figure 93I:
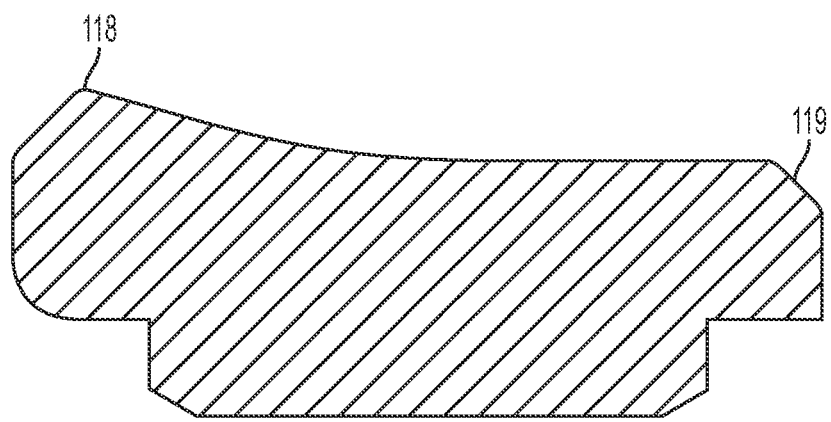
Figure 93J:
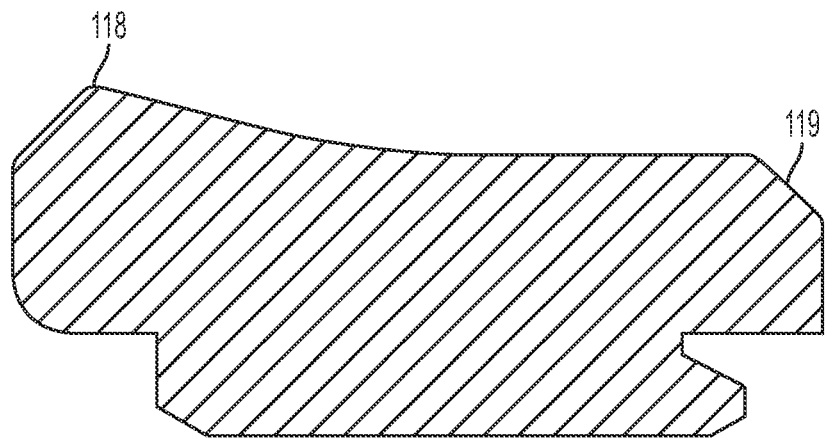
Figure 93K:
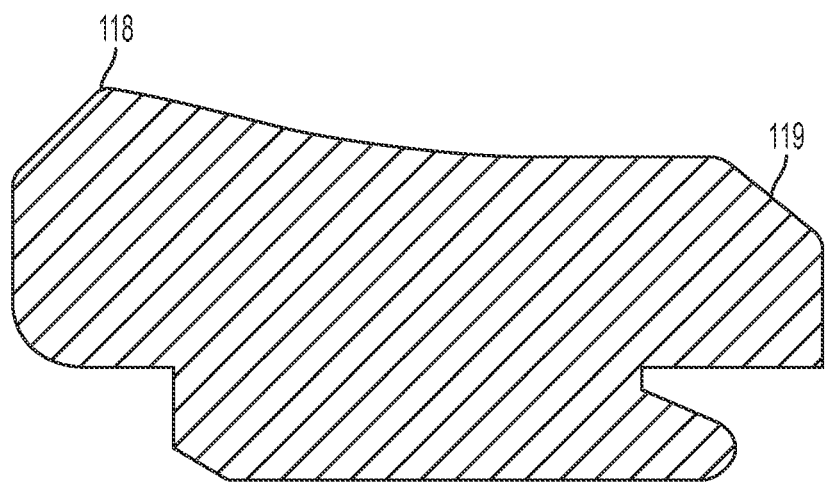
Figure 93L:
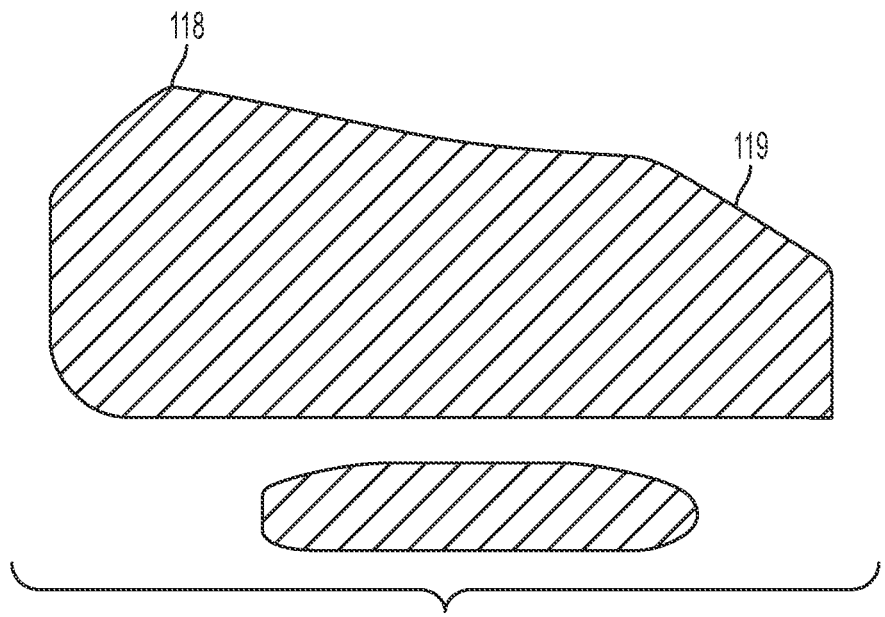
Figure 93M:
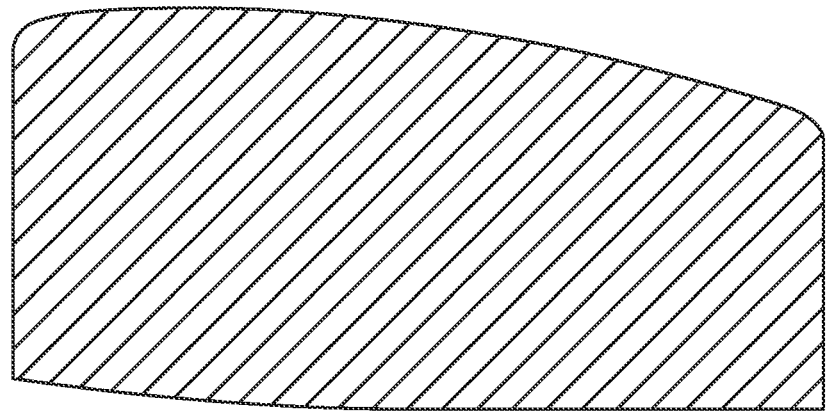

FIGS. 59-63 illustrate an embodiment of a medial insert 110, which defines a superior articulation surface, defining several different contours in various planes. For instance, FIG. 62 shows a coronal cross section of the medial insert 110 taken at a relatively middle portion of the insert 110, showing coronal contour 116a. FIG. 63 shows a sagittal cross section of the medial insert 110 taken at a relatively middle portion of the insert, showing contour 114b. FIGS. 92a-e are a series of sagittal cross sections of an embodiment of a left, medial insert illustrating the contours of that insert from relatively mesial (e.g. FIG. 92a) to relatively outer (e.g. FIG. 92e) portions of the insert. FIGS. 93a-m are a series of coronal cross sections of the same embodiment as shown in FIGS. 92a-e, the coronal cross sections of FIGS. 93a-m progressing from relatively anterior portions (e.g. FIG. 93a) to relatively posterior portions (e.g. FIG. 93m) of the insert.

Like the lateral insert, medial insert 110 also includes a mesial lip 118 and a circumferential chamfer 119 (e.g. FIG. 60). In some embodiments, anterior, mesial portions of the insert 110 are more conforming to an associated femoral component than other portions of the insert. As shown in FIG. 60, medial insert 110 also includes peripheral steps 117a, 117b. FIGS. 61 and 63 illustrate a lock mechanism 112 used to secure medial insert 110 to the tibial base member.

As shown in FIGS. 62-63 and 92-93, mesial lip 118 is raised relative to other portions and contours of the insert 120. As shown in FIG. 63, illustrating a sagittal cross section of the insert 110, such cross section taken through a middle portion of the insert 110, the raised mesial lip 118 extends from anterior to posterior portions of the insert 110. Mesial lip 118, in some embodiments, provides resistance to lateral femoral translation and prevents impingement between the femoral component 400 and the tibial eminence 222. The height of the mesial lip can be selected to provide a desired level of resistance, with a greater height providing more resistance. As shown in these embodiments, the height of the mesial lip relative to other portions of the insert 110 gradually decreases as it extends in an anterior to posterior direction. In the embodiments of FIGS. 62-63 and 92-93, outer side portions (near chamfer 119) of the medial insert 110 are substantially flat and have little to no coronal conformity with the femoral condylar articulation surfaces. In some embodiments, the maximum height of the mesial lip 118 is between a range of approximately 0.025 inches and approximately 0.125 inches relative to the substantially flat outer side portions. In some embodiments, the maximum height of the mesial lip 118 is between approximately 0.035 inches and approximately 0.065 inches for the medial insert 118.

FIGS. 64-67 illustrate graphically and pictorially the kinematics of the medial and lateral inserts 110, 120 of FIGS. 54-63 when used with other components, such as a femoral component 400 and patellar component 600 in certain arthroplasty procedures. Using LifeMOD™ computer simulations, the inventors have determined that providing a mesial lip 118 on the medial tibial insert 110 serves to prevent the femoral component 400 from translating laterally in response to the lateral forces applied to the femoral component 400 by the patella due to the quadriceps angle, or "Q-angle." In some embodiments, without the mesial lip 118, the femoral component 400 may translate laterally in flexion due to patella shear, creating an environment where the medial condyle 408 moves too close to the attachment point of the posterior cruciate ligament 320 and surrounding bone 220, 222. In addition to increasing the overall performance of the prosthesis over prior art designs, in some embodiments, the raised mesial lip 118 further provides additional tibio-femoral contact when the leg is in extension. In some embodiments, it is envisaged that the medial insert 110 comprises a mesial lip 118 and the lateral insert 120 does not comprise a mesial lip 128, although mesial lips 118, 128 may be added to both inserts 110, 120 for additional stabilization.

Figure 64:
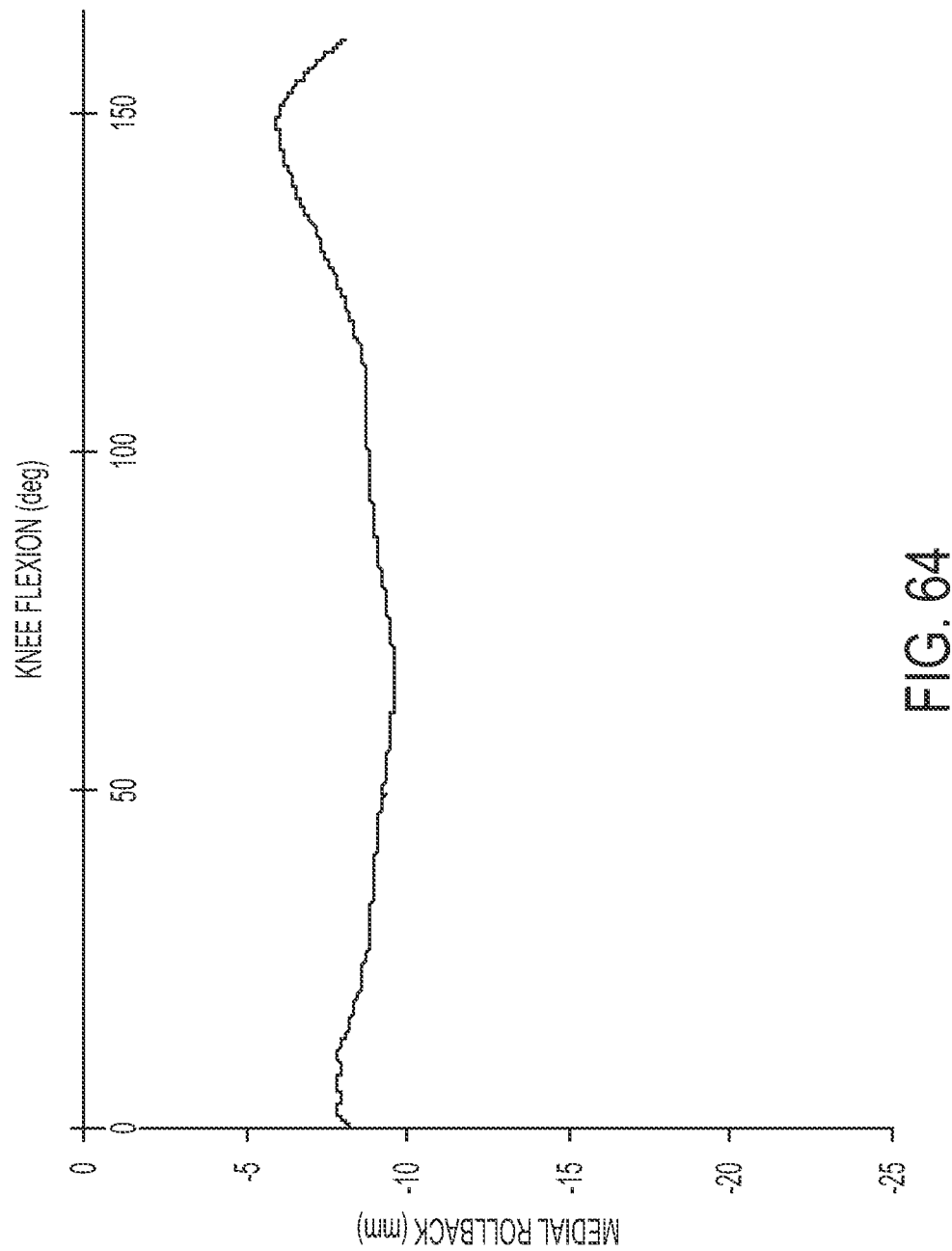
FIGS. 64-66 graphically illustrate the kinematics of one embodiment of a femoral implant when used in conjunction with the bicruciate-retaining tibial prosthesis shown in FIGS. 38-46.
Figure 65:
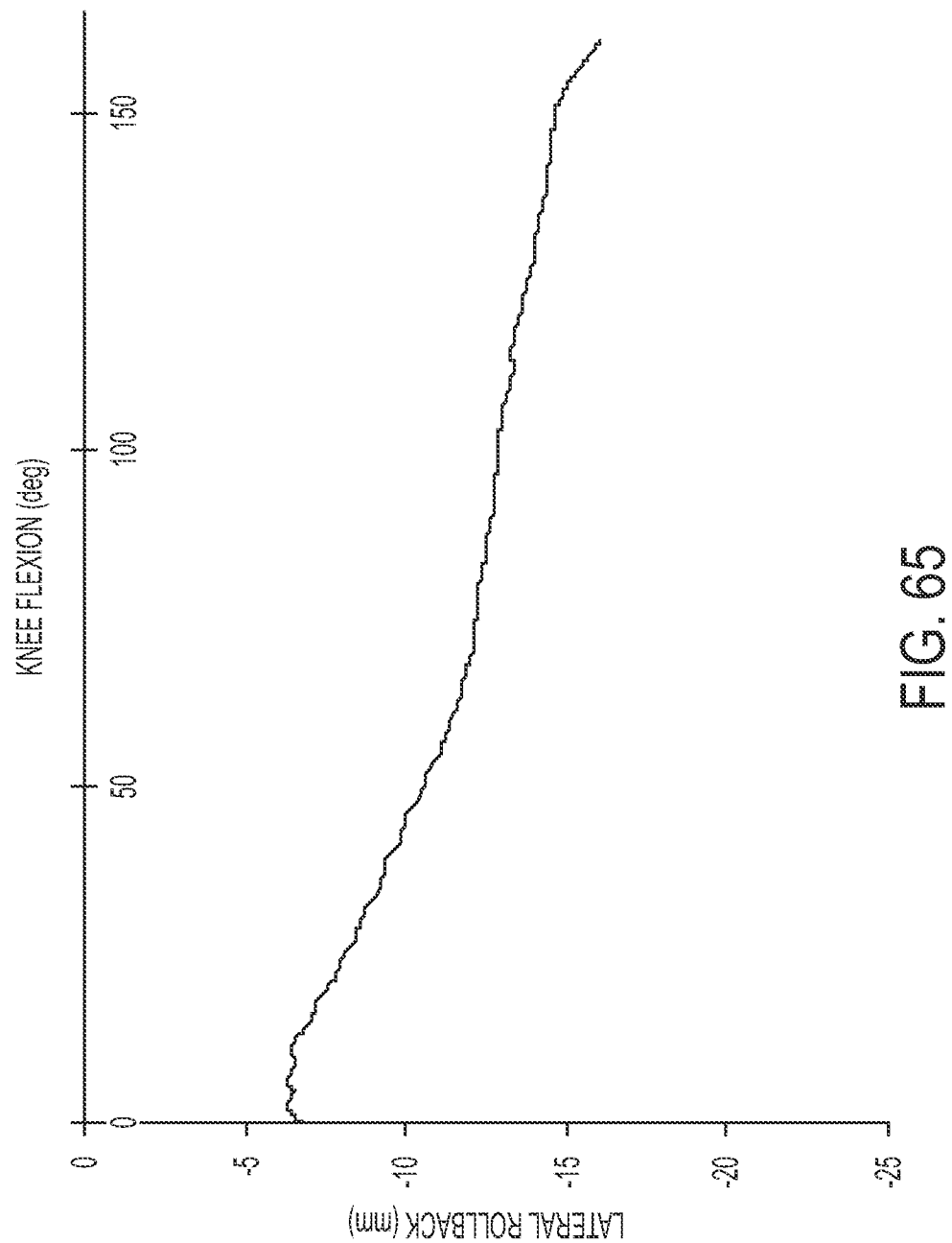
Figure 66:
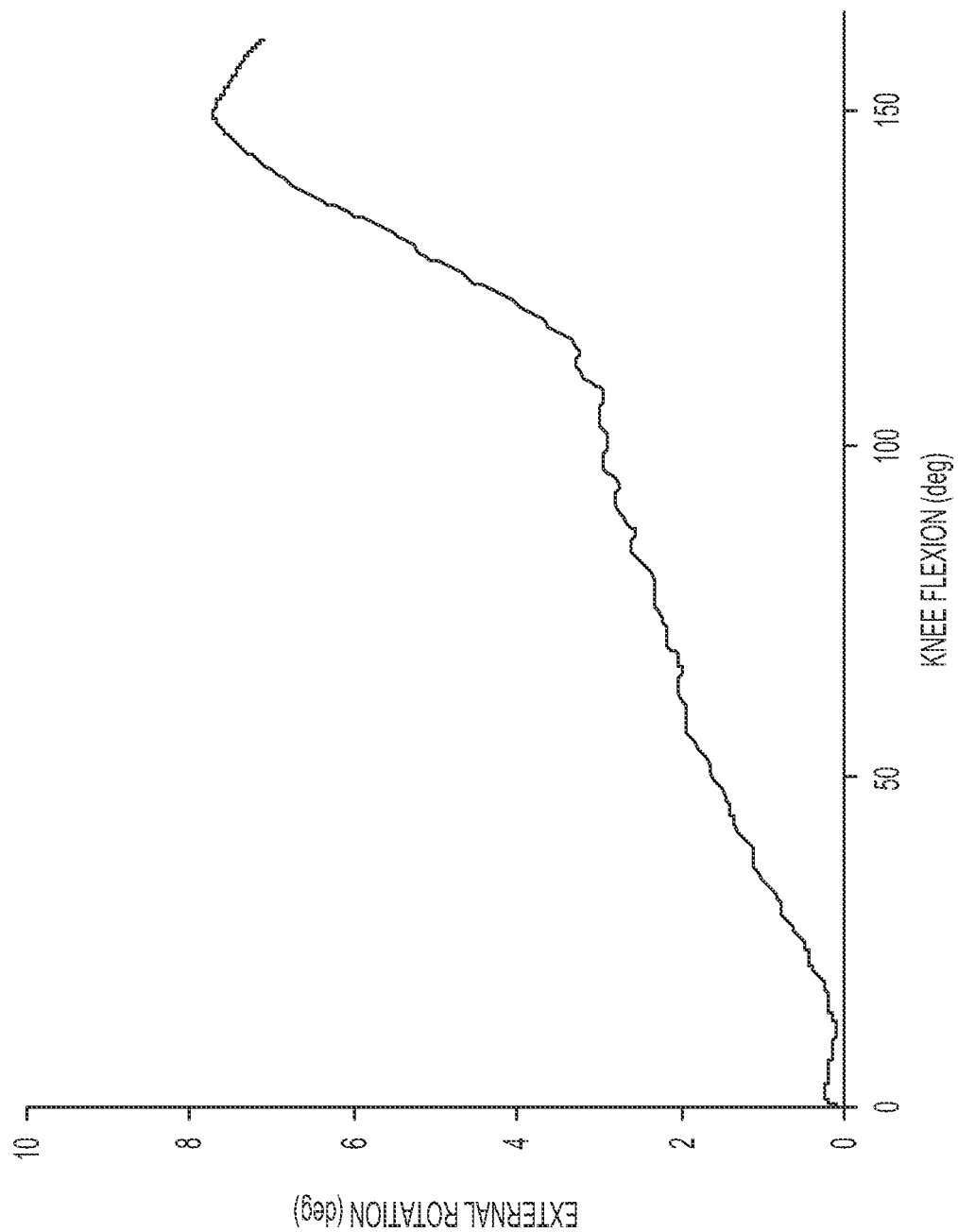
Figure 67A:
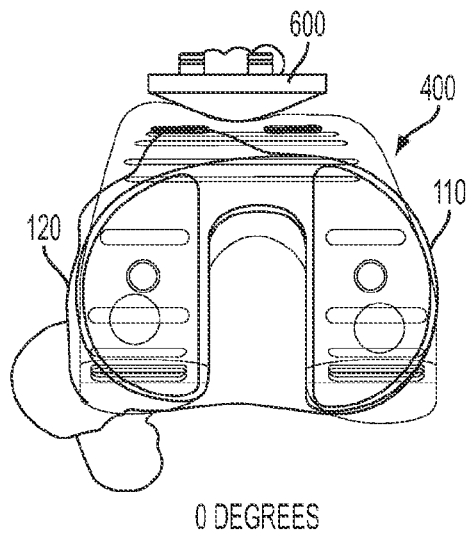
FIGS. 67*a*-67*q* illustrate the kinematics of FIGS. 64-66 for various angles of flexion.
Figure 67B:
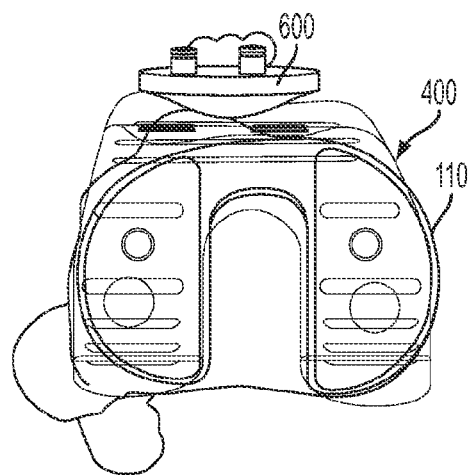
Figure 67C:
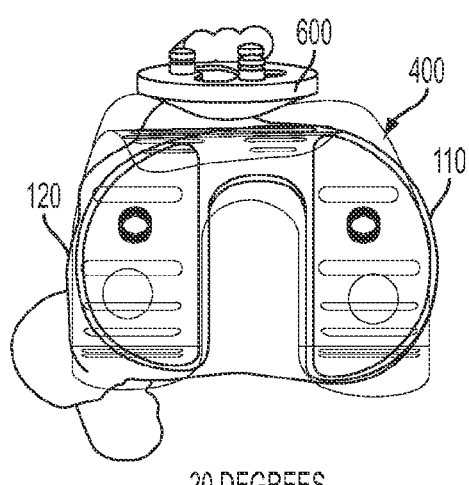
Figure 67D:
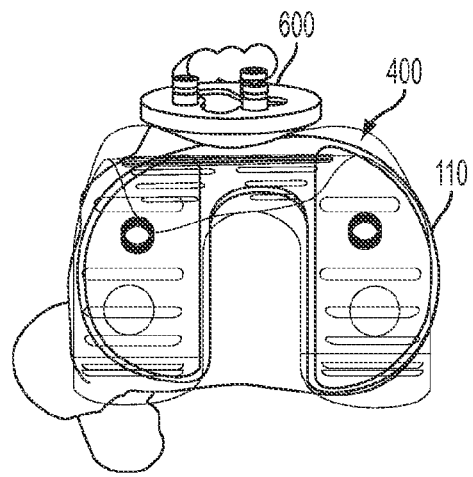
Figure 67E:
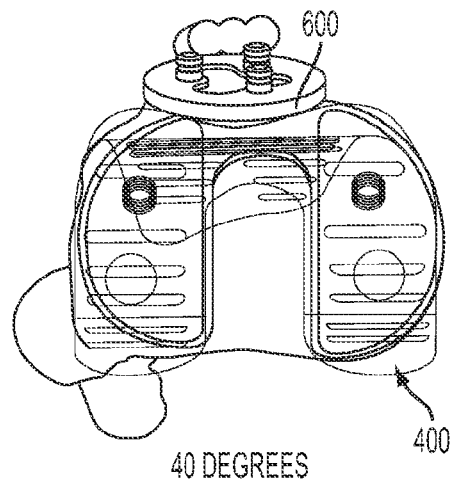
Figure 67F:
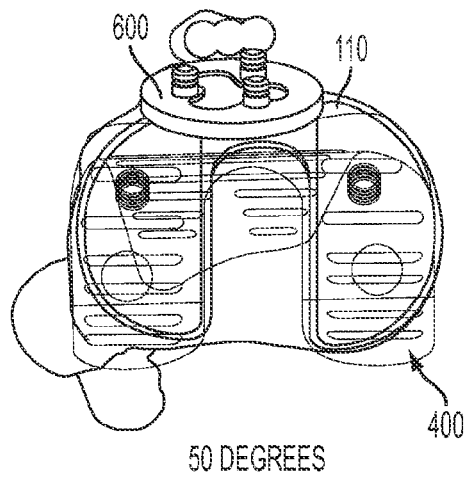
Figure 67G:
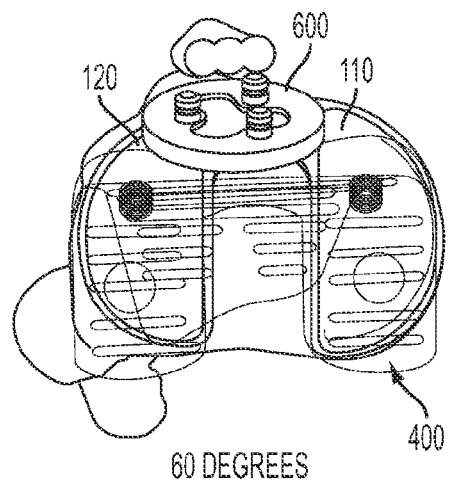
Figure 67H:
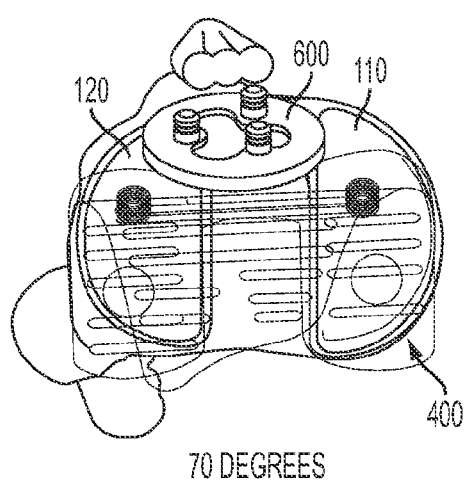
Figure 67I:
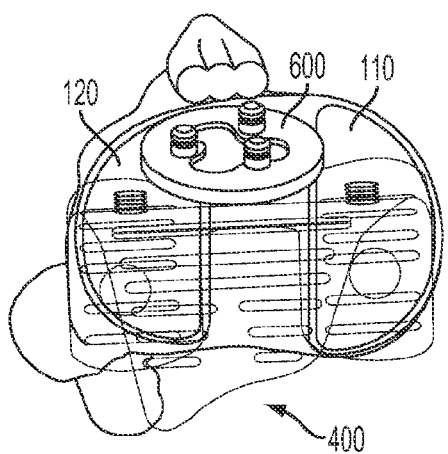
Figure 67J:
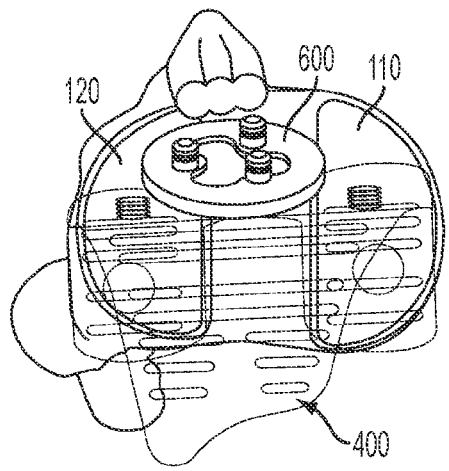
Figure 67K:
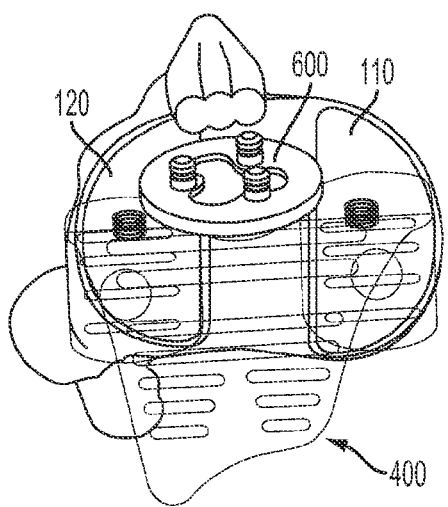
Figure 67L:
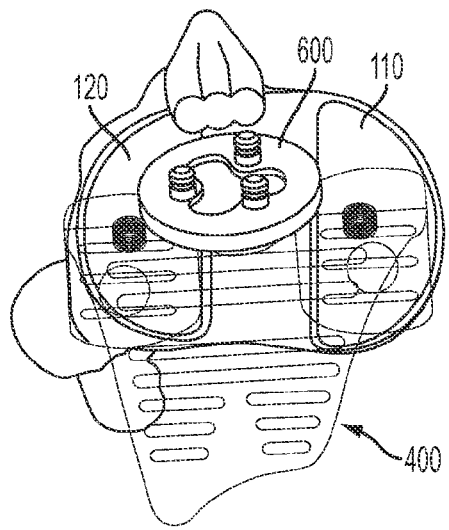
Figure 67M:
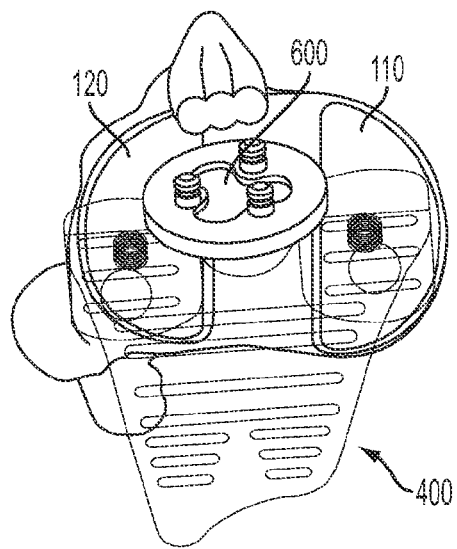
Figure 67N:
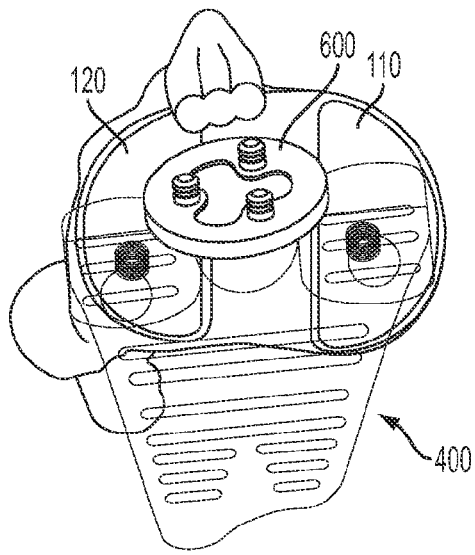
Figure 67O:
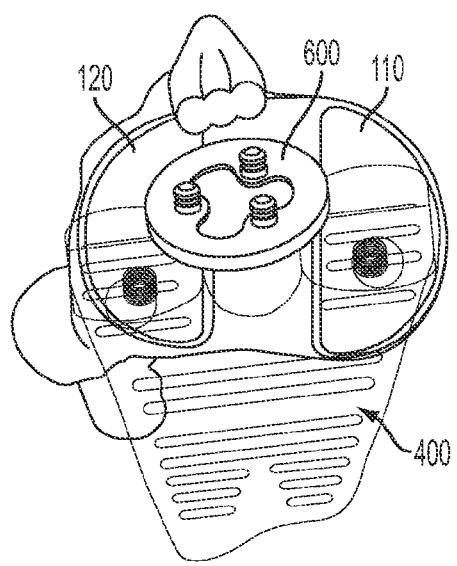
Figure 67P:
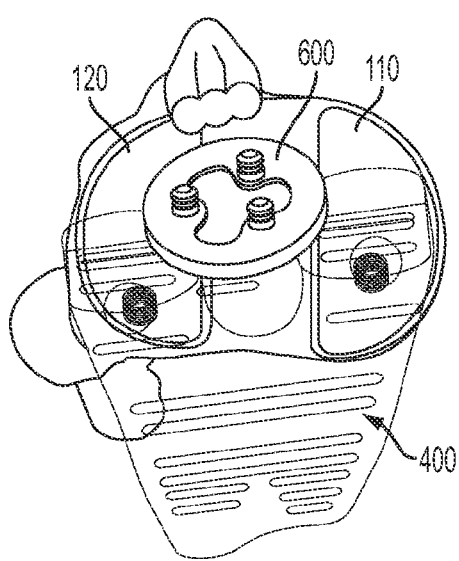
Figure 67Q:
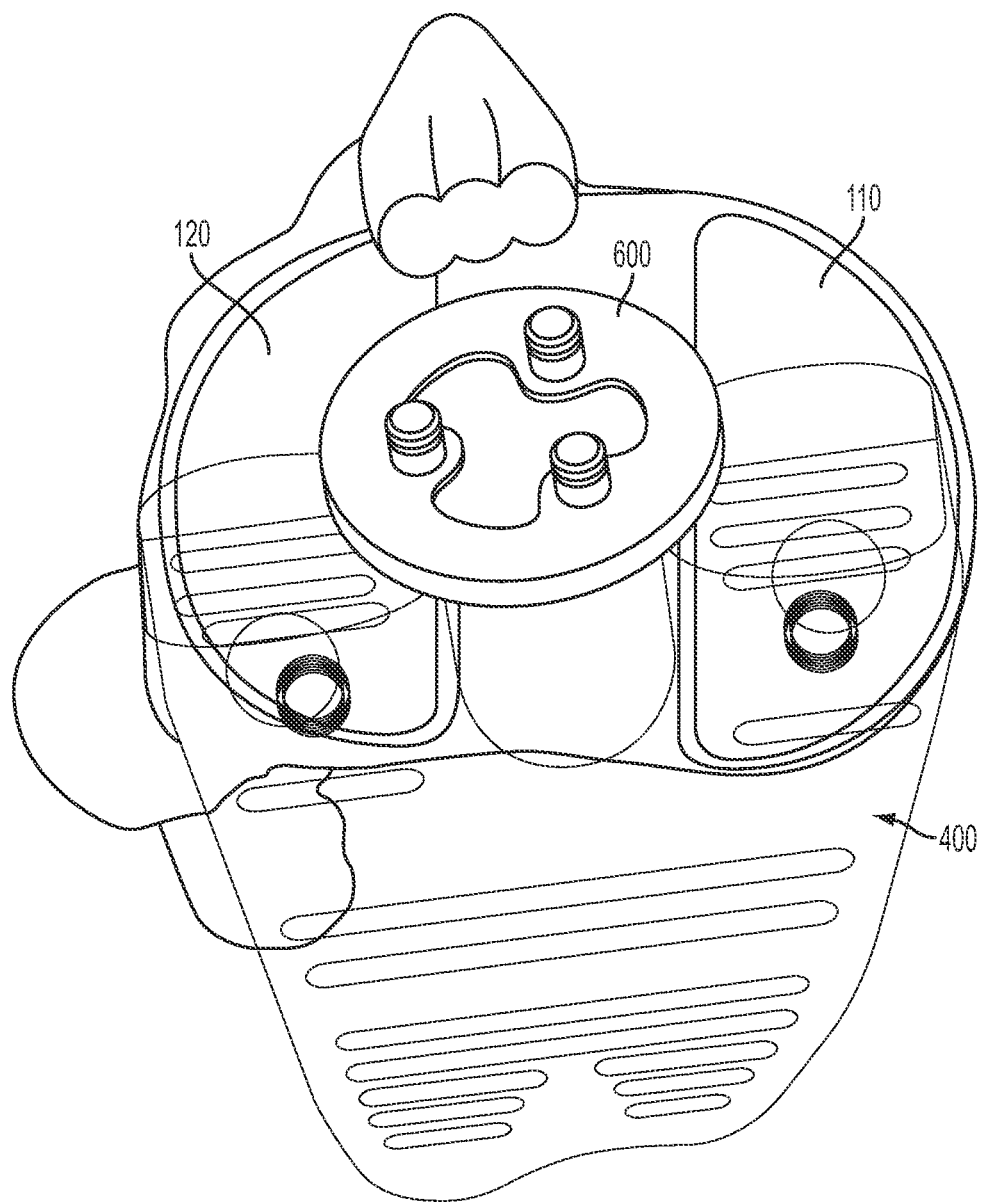

FIGS. 64-66 graphically illustrate the medial femoral rollback, lateral femoral rollback, and external femoral rotation respectively of femoral implant 400 when used in conjunction with the implant 100 shown in the embodiment of FIGS. 38-46. This, in some embodiments, may be in contrast to at least some previous bicruciate-retaining designs, which employed overly-conforming coronal profiles in regions adjacent to the femoral component towards the midline and outer peripheral edges of the tibial insert. This over-conformity present in some prior art designs negatively constrains internal-external rotation of the femoral component and reduces or eliminates medial-lateral translation. At least some known designs have also demonstrated high amounts of conformity at anterior and posterior portions of the insert, which negatively limit femoral rotation during knee extension and flexion. The design shown in FIG. 68, in this particular embodiment, generally only provides coronal conformity towards a midline of the tibia, said coronal conformity gradually reducing towards the posterior edges of the insert. Because of this reduction in conformity, this particular design more freely allows internal and external rotation of the femoral component 400 and more closely replicates normal knee kinematics in flexion, where the femoral component 400 is rotated externally relative to the tibial prosthesis 100. Other embodiments, however, may feature relatively highly conforming inserts similar to those of other prior art designs.

In some instances, a plurality of different posterior slope angle options may be provided to tibial inserts 110 and/or 120. In one embodiment, inserts such as 110 and/or 120 are thinned posteriorly by different amounts so as to effectively rotate the articular surfaces by a flexion-extension angle relative to the bottom surfaces of the inserts 110, 120 and provide more posterior slope. Such an option may, in some embodiments, allow a surgeon to selectively adjust joint laxity when the knee is in flexion. For instance, several pairs of medial 110 and lateral 120 inserts may be provided, each pair differing in posterior slope from the other pairs by a specified number of degrees between about 1-4 degrees, for instance 2 degrees.

Other options may include pairing medial 110 and lateral 120 inserts, wherein the posterior slope of the medial insert 110 differs from the posterior slope of the lateral insert 120. Such options may generally allow the flexion space to be adjusted without necessarily requiring a re-cut of tibial bone 220. Multiple thickness options for each of the medial 110 and lateral 120 inserts are also provided for the abovementioned options to afford proper ligament balance. Various combinations and configurations of insert thicknesses, medial-lateral slope, and anterior-posterior slope may be utilized to suit the particular anatomical needs of an individual patient. The options of multiple thickness, medial-lateral slope, and anterior-posterior slope may also be configured in the tibial base plate to provide these configurations while using a single insert.

Figure 80:
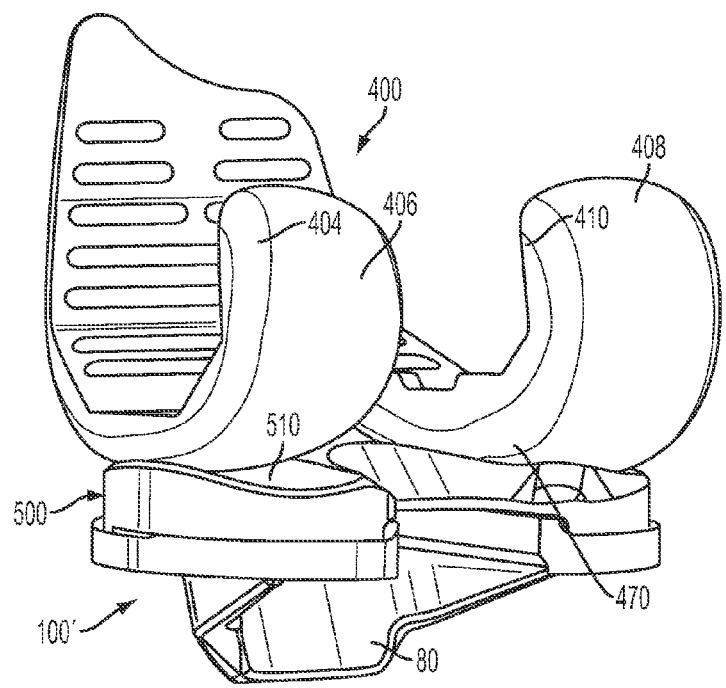
Figure 81:
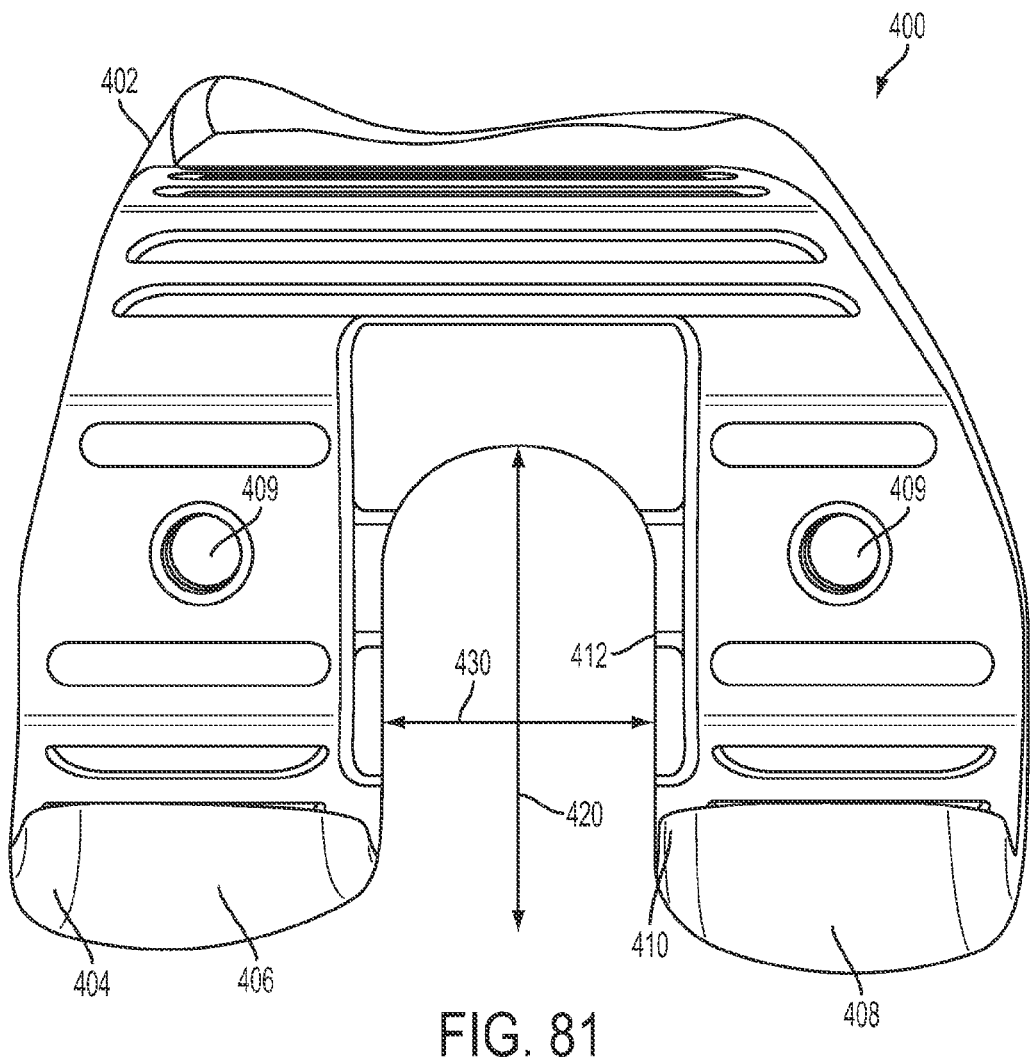
FIG. 81 is a superior view of the femoral component shown in FIGS. 67*a*-80.
Figure 82:
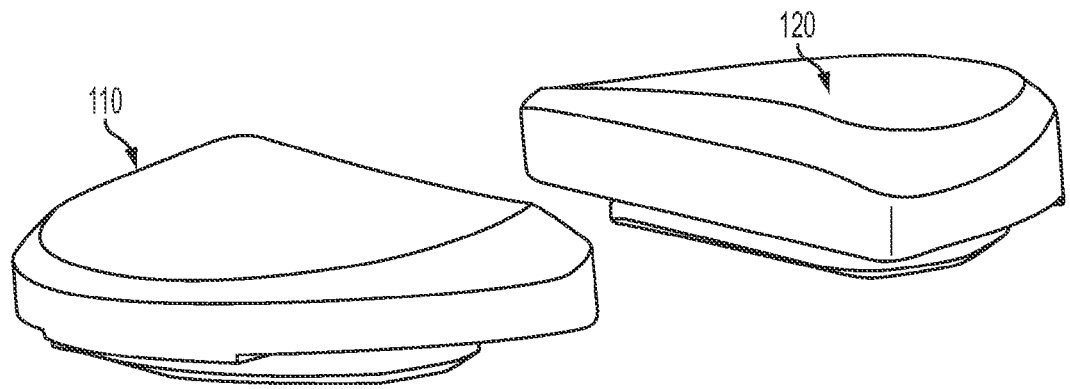
FIGS. 82-84 show various prospective views of the medial and lateral inserts of FIGS. 54-63.
Figure 83:
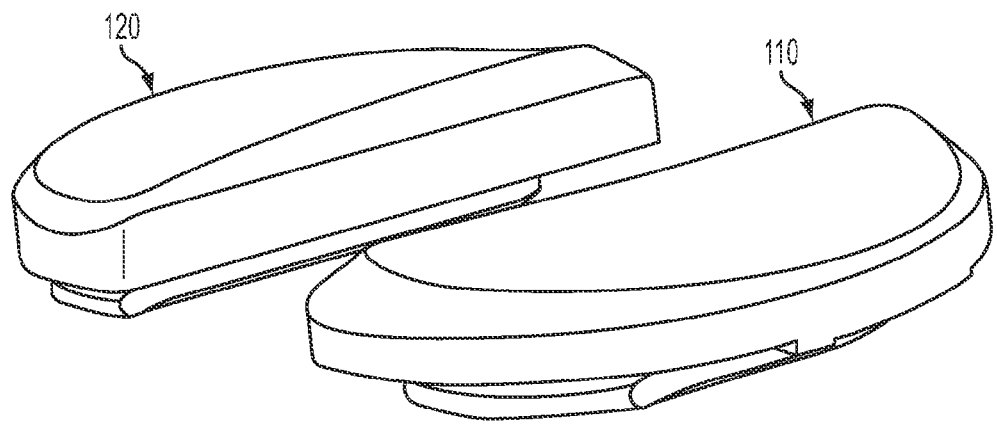
Figure 84:
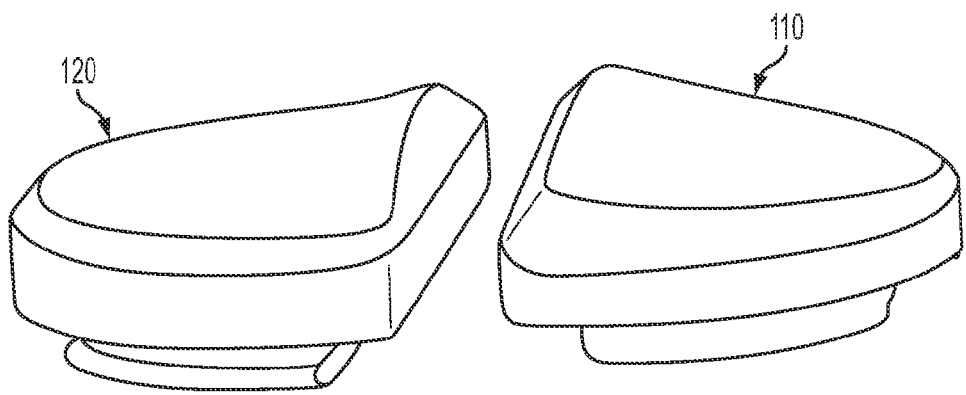
Figure 85:
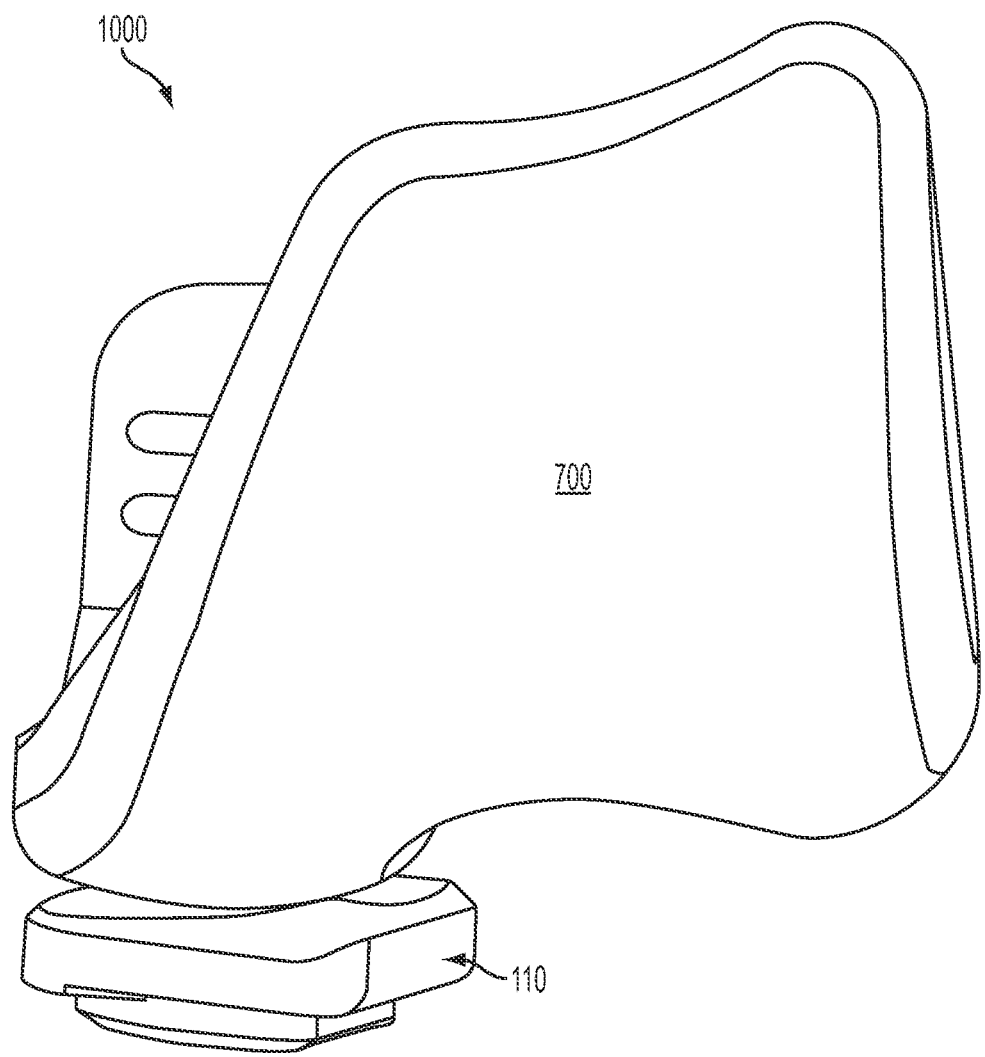
FIG. 85 shows a bicompartmental knee implant according to another embodiment that employs a medial insert according to some embodiments and that may be used in conjunction with a medial unicondylar tibial base member (not shown) and that alternatively may be configured as a lateral bicompartmental knee implant (not shown).
Figure 86:
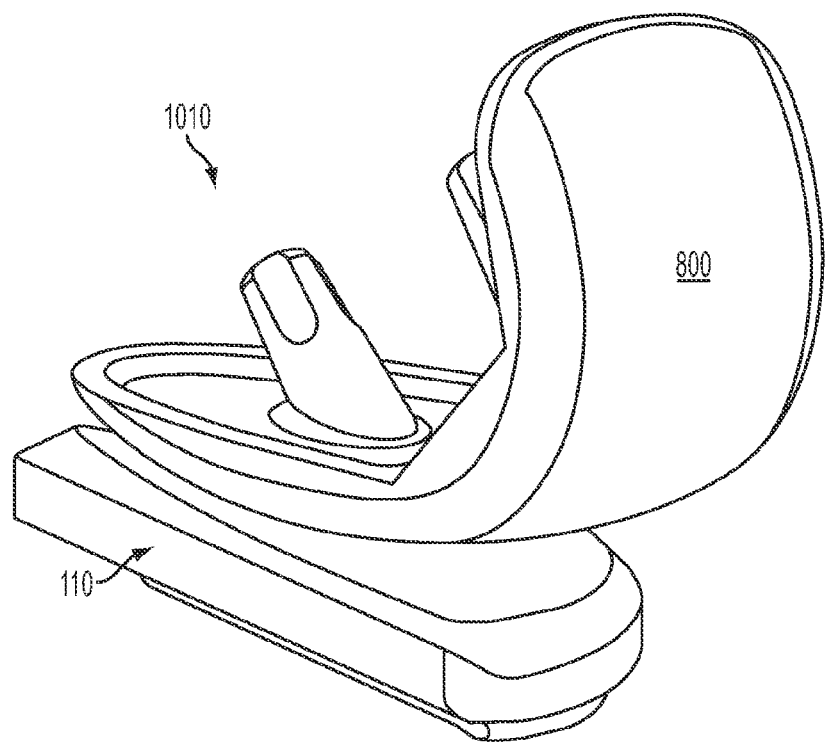
FIG. 86 shows a medial unicondylar knee implant according to another embodiment, which employs a medial insert according to some embodiments and which may be used in conjunction with a medial unicondylar tibial base member (not shown).
Figure 87:
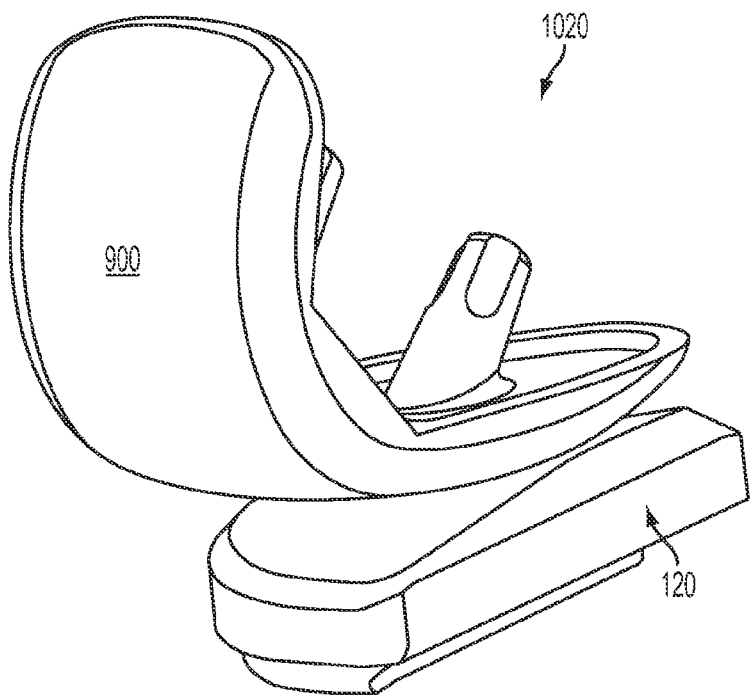
FIG. 87 shows a lateral unicondylar knee implant according to another embodiment, which employs a lateral insert according to some embodiments and which may be used in conjunction with a lateral unicondylar tibial base member (not shown).

In some embodiments, the articular geometries of the medial 110 and lateral 120 inserts may be provided by a single cruciate-containing insert 500, which, as shown in FIGS. 69, 71, 73, 75, 78, and 80, comprises concave medial and lateral articulating surfaces. As shown in FIG. 80, the lateral portion 510 of the insert 500 may be thicker (in some embodiments, approximately 2.5 mm thicker) than the medial portion to allow functionality with the femoral components 400 shown. The thicker lateral portion 510, in this particular embodiment, serves to match the varus joint line present on the femoral component 400.

In other embodiments, medial 110 and lateral 120 inserts may be provided, each having different posterior slope angles or thicknesses, and may be utilized in various combinations in order to address different medial and lateral collateral ligament balancing needs. In some instances, a set of inserts 110, 120 including a plurality of sizes may be provided in a surgical implant kit, wherein a general angle between a bottom plane of a particular insert 110, 120 and its corresponding articulating surface varies between inserts. This angle may increase or decrease in either or both of an anterior-posterior direction and a medial-lateral direction independently or collectively. Providing multiple posterior slope options may advantageously reduce the need for re-cutting the tibia 220.

Figure 68:
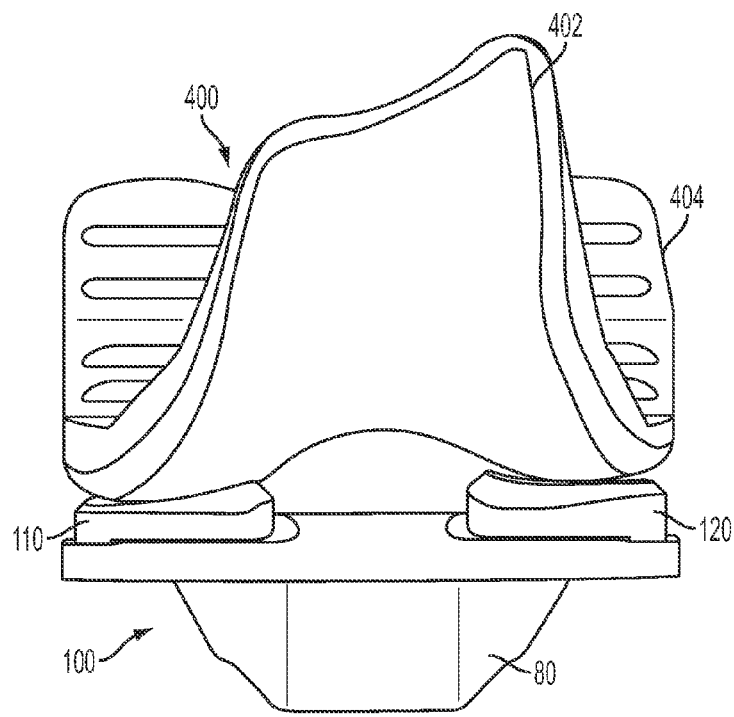
FIG. 68 is an anterior view of one embodiment of a bicruciate-retaining knee prosthesis (ACL and PCL sparing).
Figure 69:
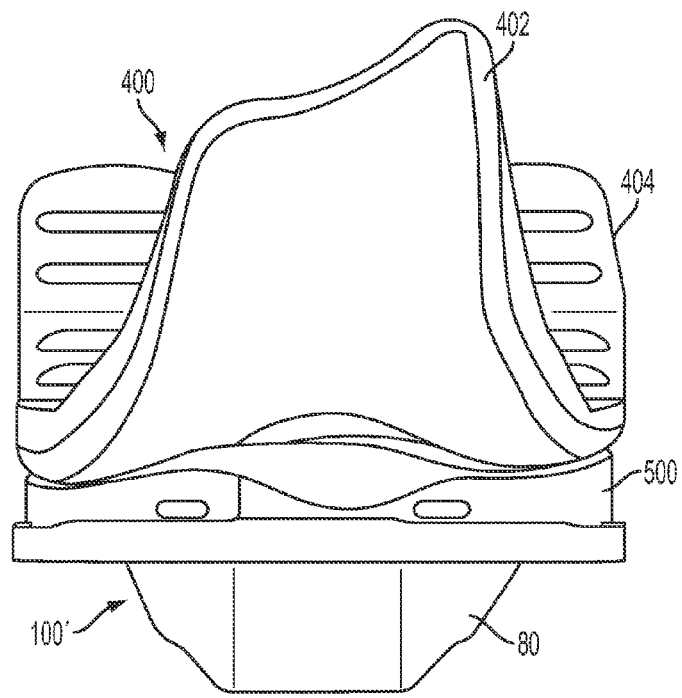
FIG. 69 is an anterior view of one embodiment of a cruciate-retaining knee prosthesis (PCL sparing).
Figure 70:
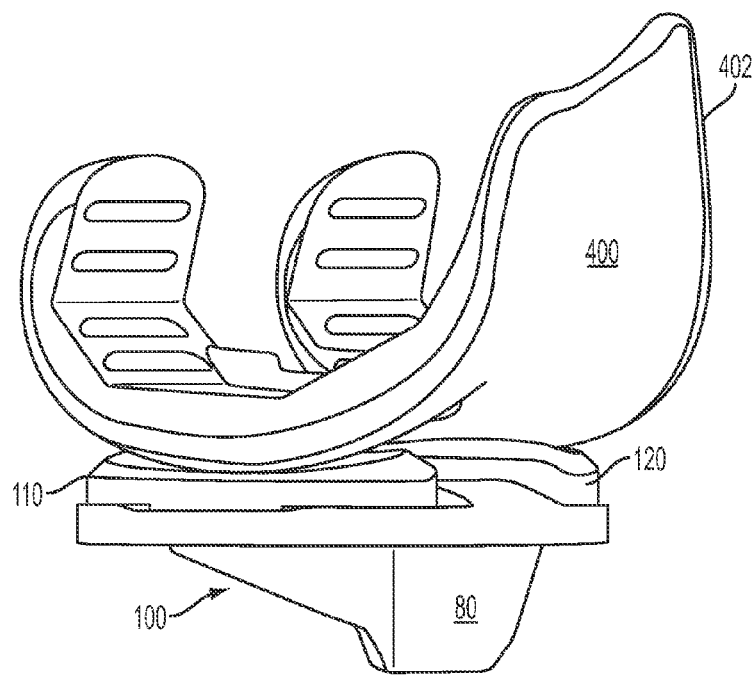
FIGS. 70 and 71 are anteromedial views of the bicruciate-retaining and cruciate-retaining knee prostheses of FIGS. 68 and 69, respectively.
Figure 71:
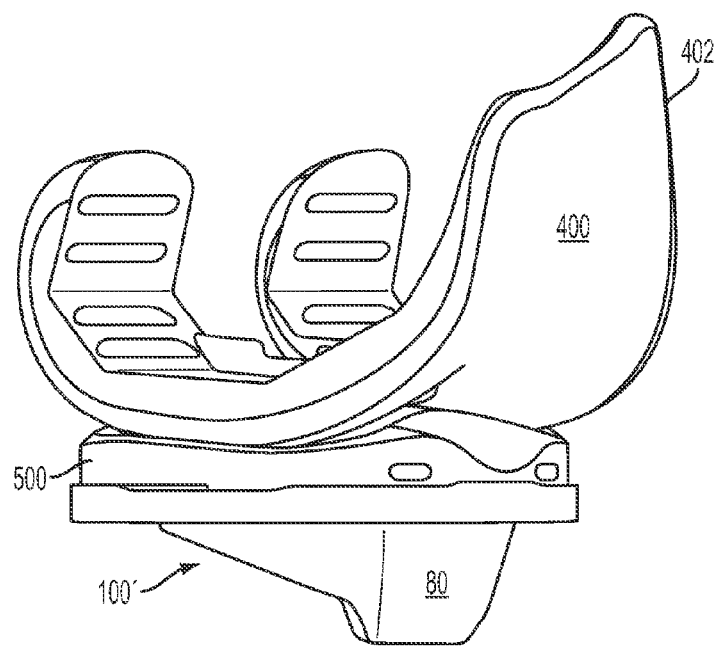
Figure 72:
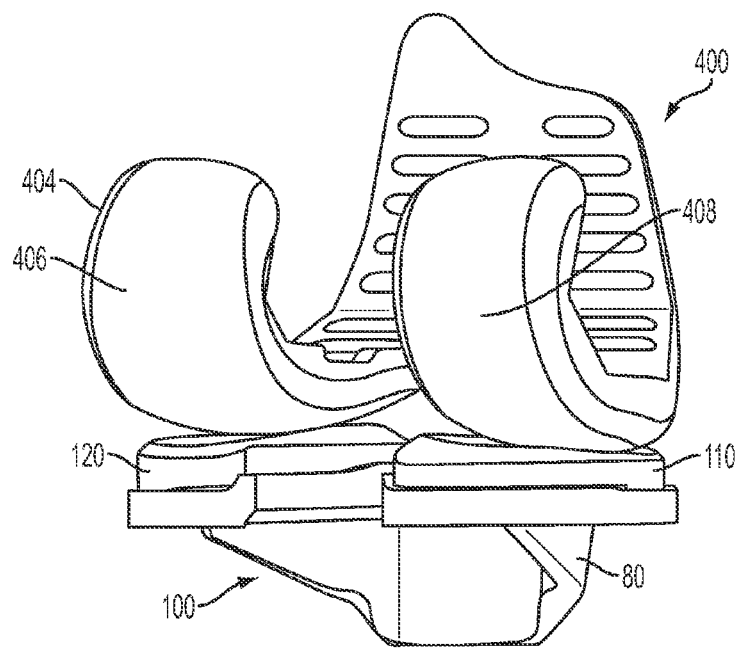
FIGS. 72 and 73 are posteromedial views of the bicruciate-retaining and cruciate-retaining knee prostheses of FIGS. 68 and 69, respectively.
Figure 73:
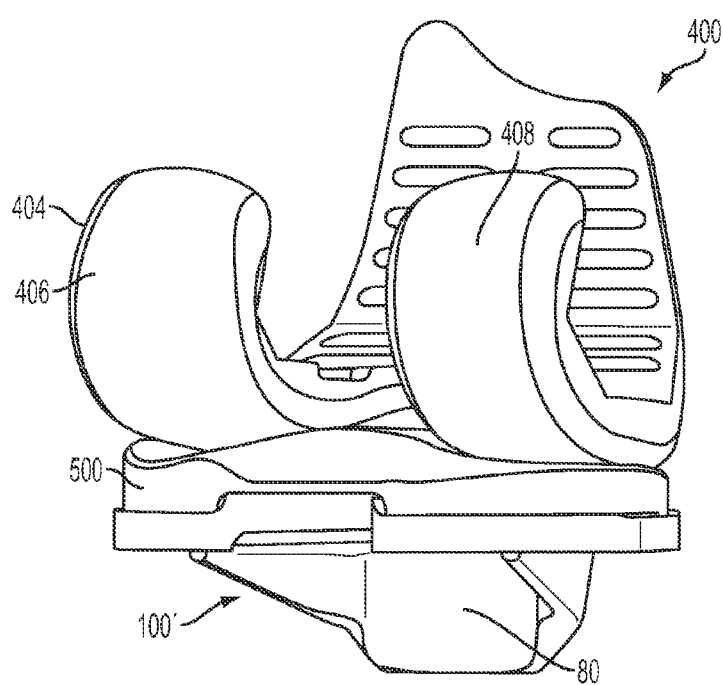

FIGS. 56 and 68 illustrates an example of a convex lateral insert 120, which facilitates external rotation of the femoral component 400 during flexion and through lateral femoral rollback, while the medial femoral condyle 408 is constrained by the sagittal concave geometry of the medial insert 110 as provided by some embodiments.

Figure 88:
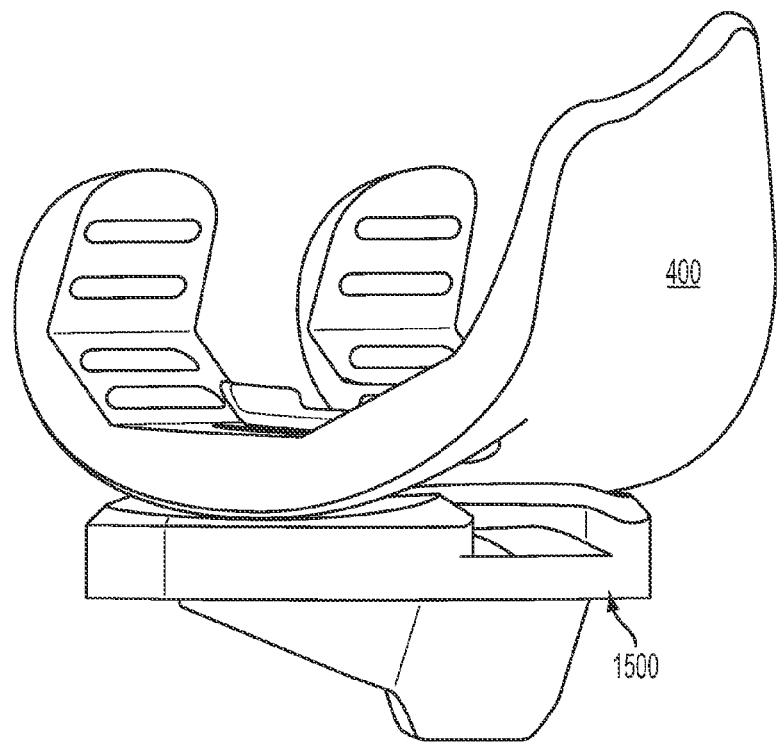
FIG. 88 shows a monolithic bicruciate-retaining prosthesis according to one embodiment, wherein the tibial base member comprises integrally-formed articulating surfaces.
Figure 89:
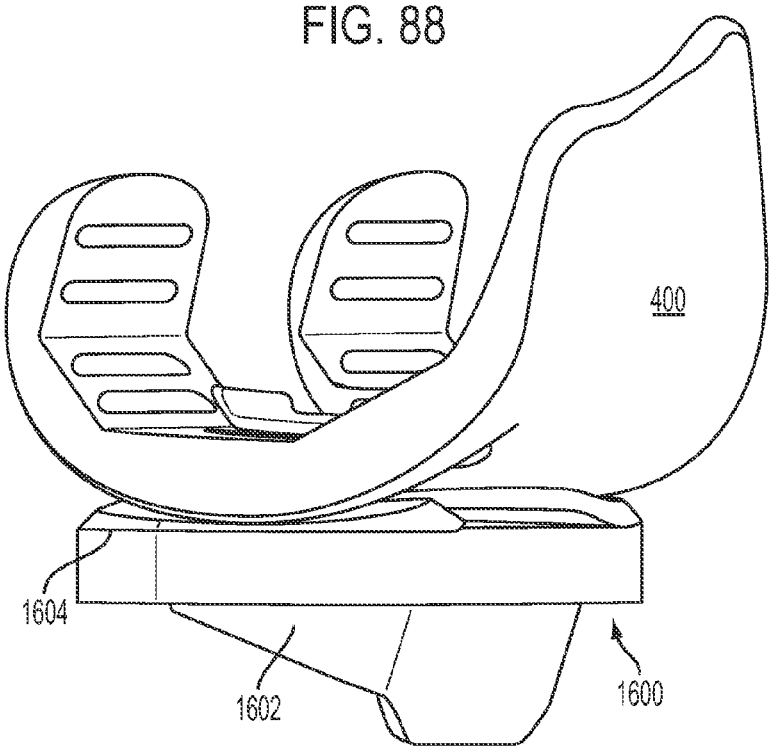
FIG. 89 shows a monolithic bicruciate-retaining prosthesis according to one embodiment, wherein the tibial base member is a fully or partially porous augment comprising integrally-formed articulating surfaces.
Figure 90A:
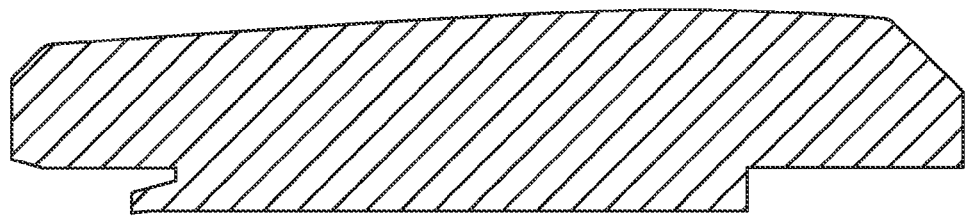
FIGS. 90*a*-90*e* show various sagittal cross-sectional views of a lateral insert when viewed from the medial side.
Figure 90B:
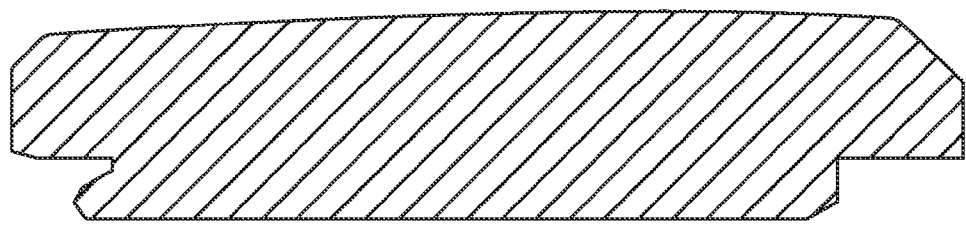
Figure 90C:
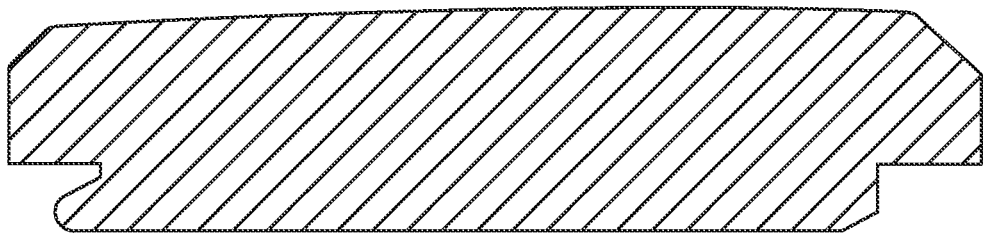
Figure 90D:
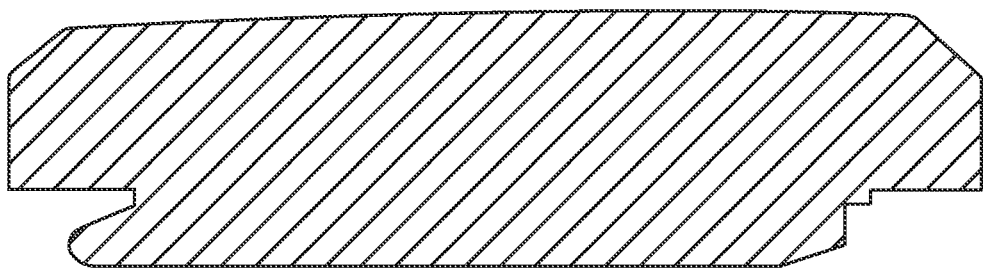
Figure 90E:
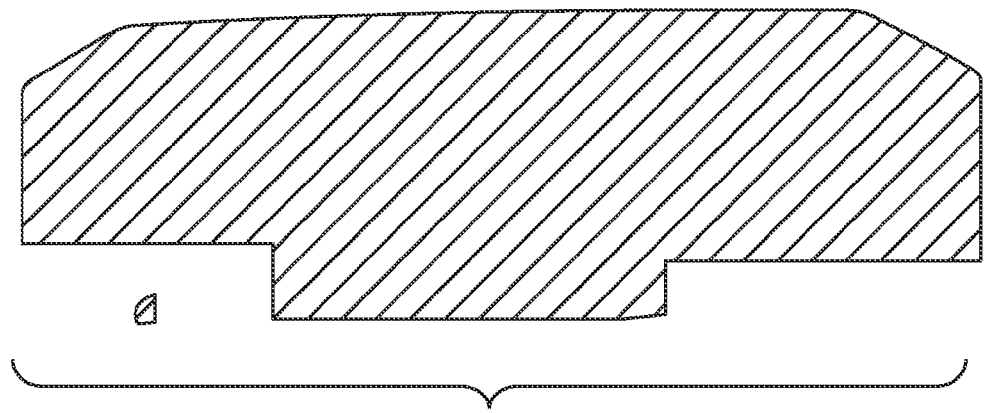
Figure 91A:
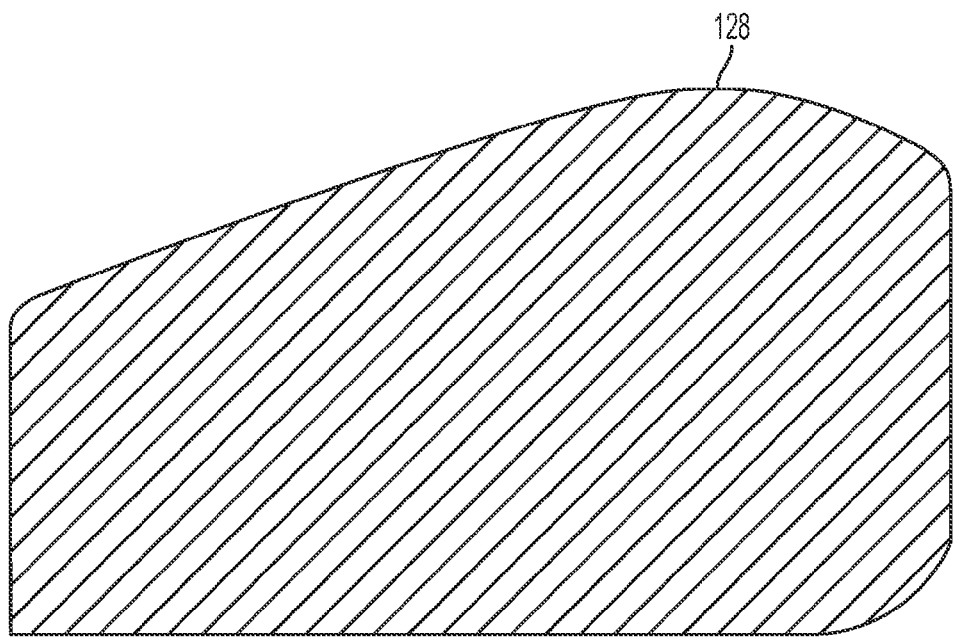
FIGS. 91*a*-91*k* show various coronal cross-sectional views of a lateral insert when viewed from the posterior side.
Figure 91B:
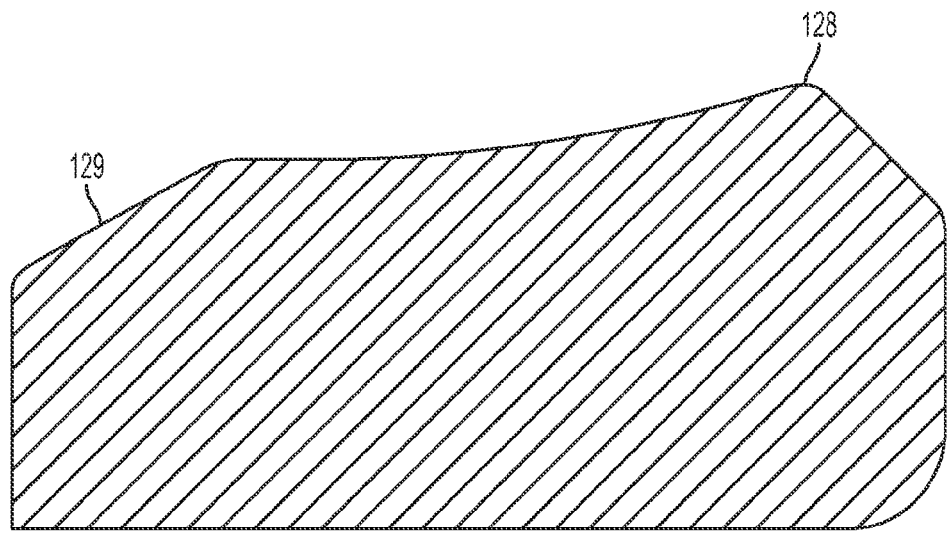
Figure 91C:
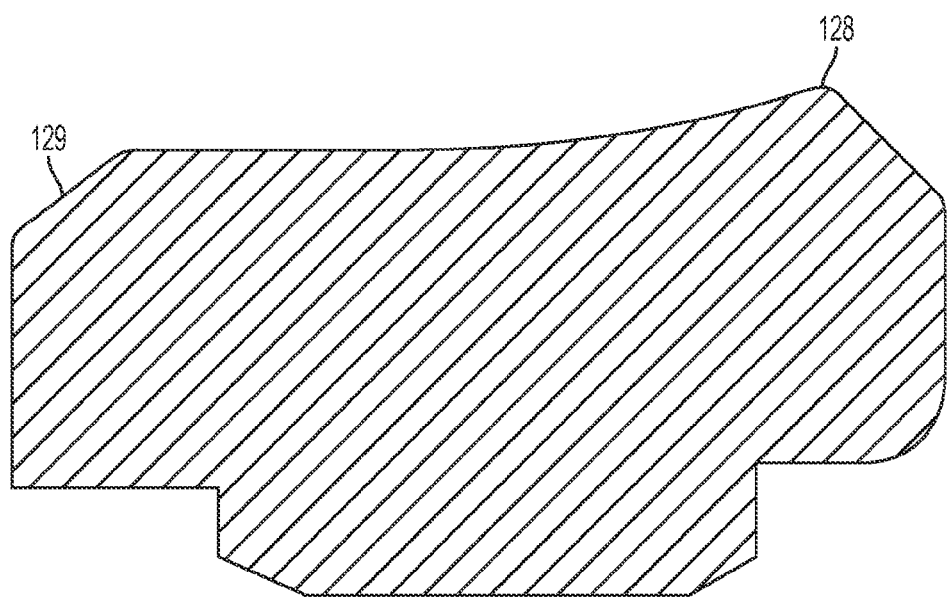
Figure 91D:
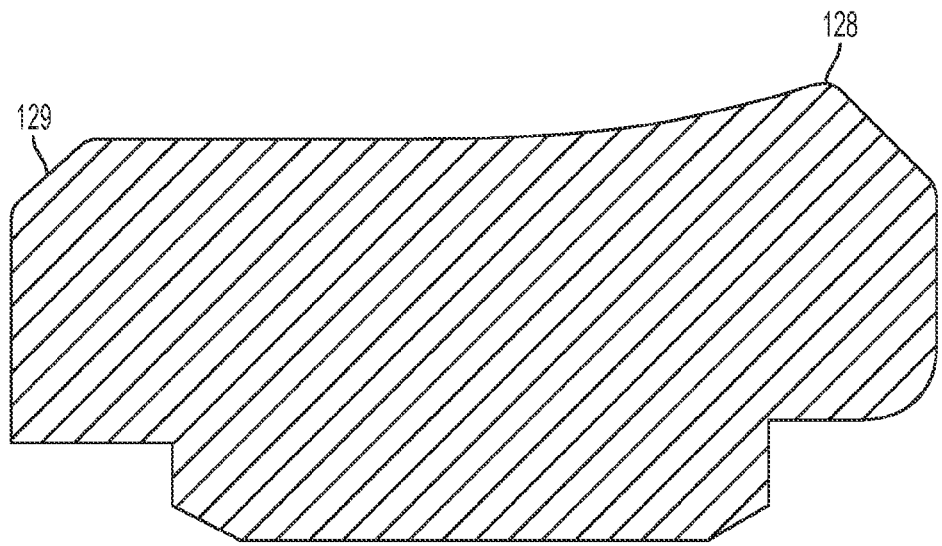
Figure 91E:
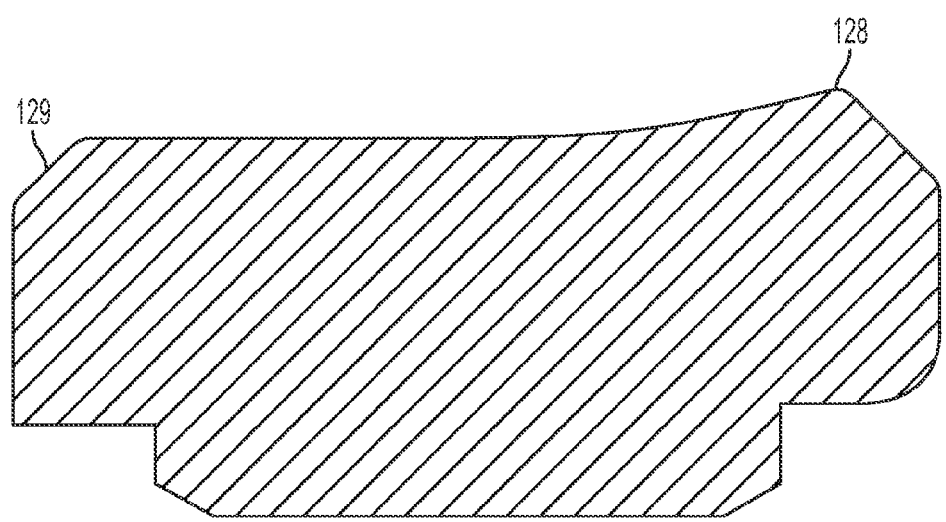
Figure 91F:
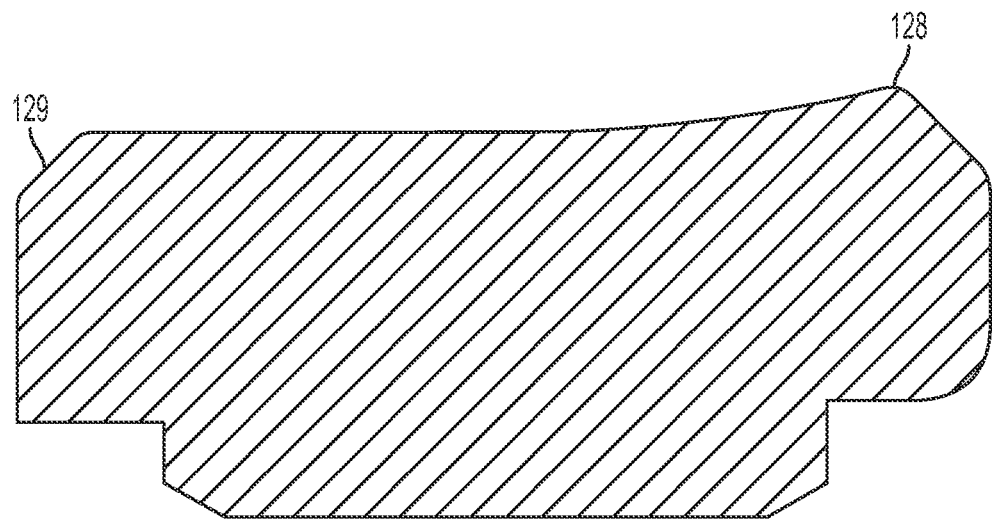
Figure 91G:
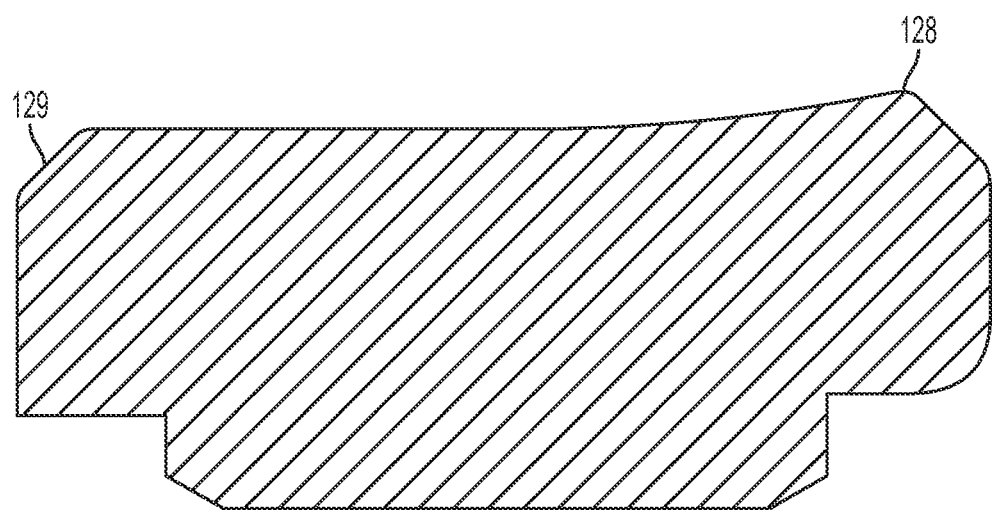
Figure 91H:
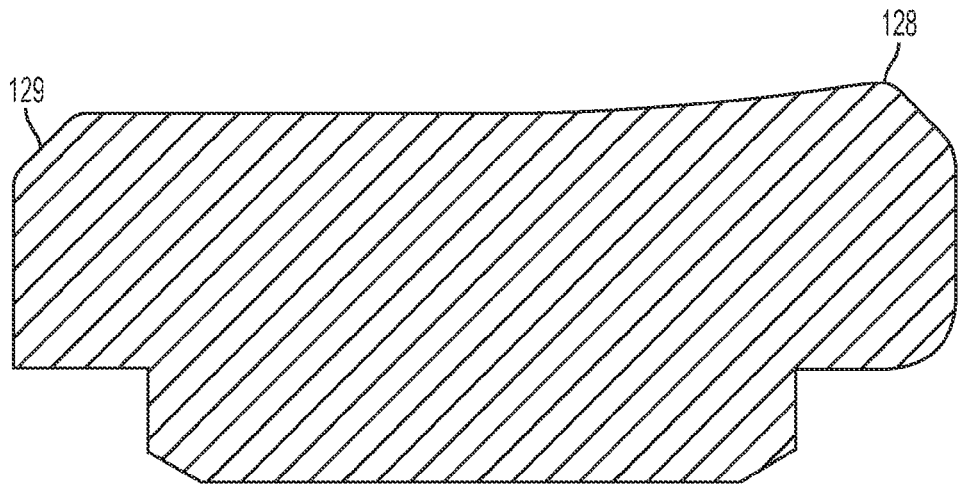
Figure 91I:
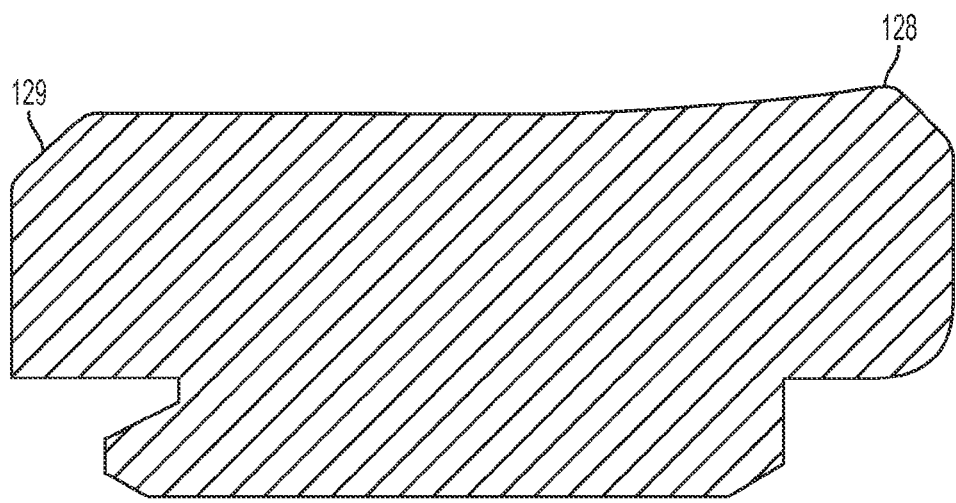
Figure 91J:
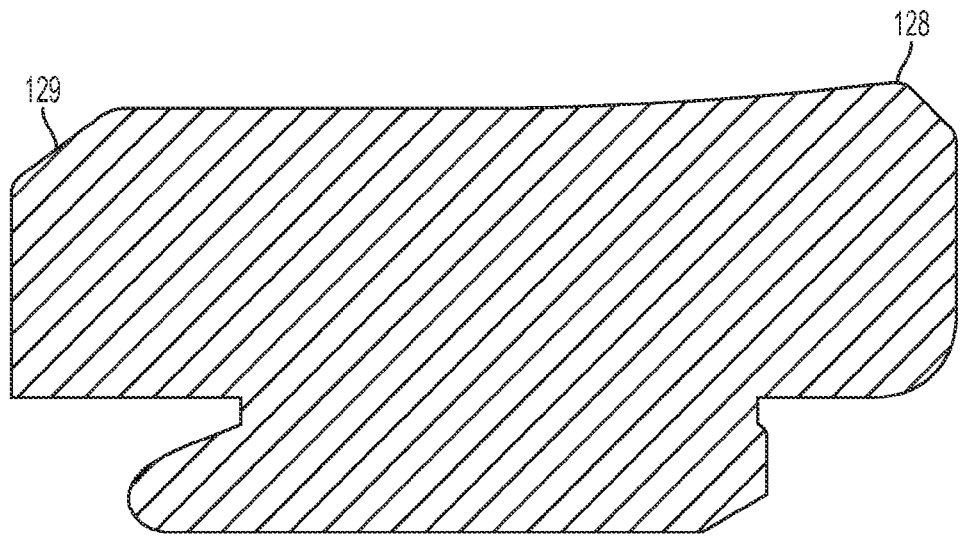
Figure 91K:
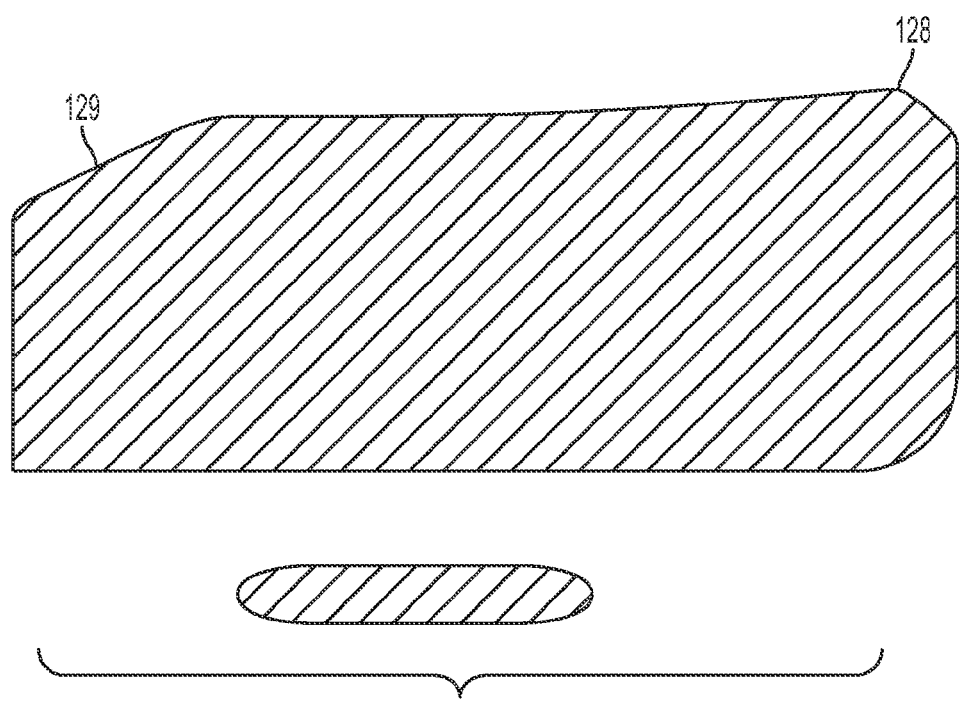
Figure 92A:
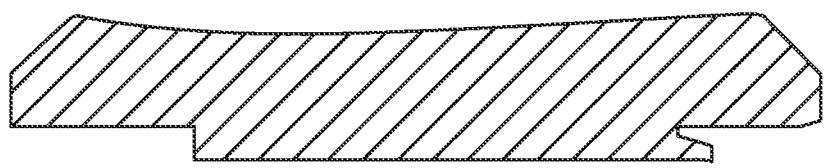
FIGS. 92*a*-92*e* show various sagittal cross-sectional views of a medial insert when viewed from the lateral side.
Figure 92B:
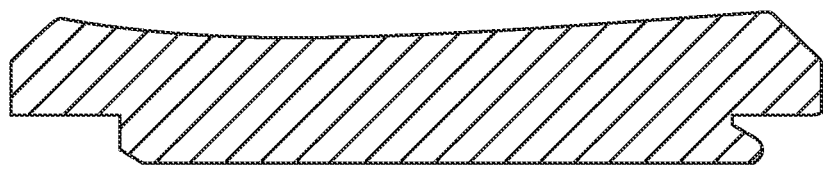
Figure 92C:
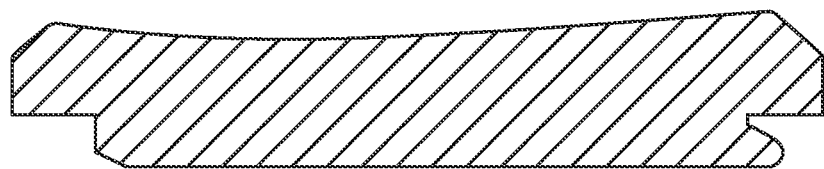
Figure 92D:
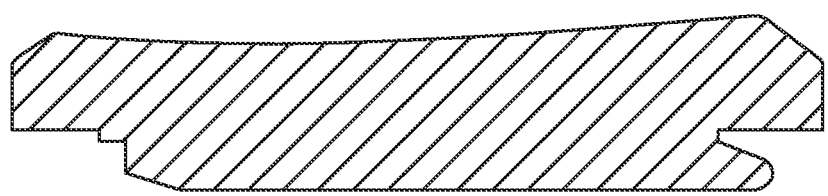
Figure 92E:
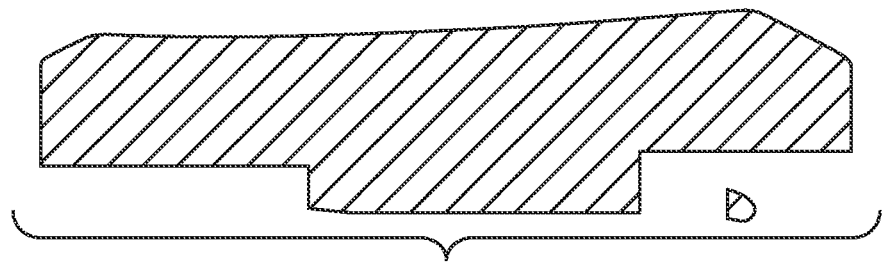

As another alternate to using separate tibial inserts 110, 120, a tibial base member 1500 shown in FIG. 88 may comprise integrally-formed monolithic articulating surfaces. Other embodiments, such as shown in FIG. 89, may include a tibial prosthesis 1600 formed of a porous structure material 1602 such as a metal foam, with articulating surfaces 1604 modularly or integrally provided at a proximal region of the porous structure 1602, as shown in FIG. 89. For instance, the articulating surfaces 1604 may be formed as a solid metal, ceramic, polymer, coating, or compliant material disposed on a proximal side of the porous structure. This may be accomplished using conventional rapid manufacturing techniques such as selective laser sintering (SLS), electron beam welding (EBM), 3D printing, or stereolithography. Alternatively, the porous structure 1602 may be overmoulded with a polymer to form a monolithic base member 1600 having a porous structure 1602 and an articulating surface 1604 of different materials.

3. Femoral Components

Figure 74:
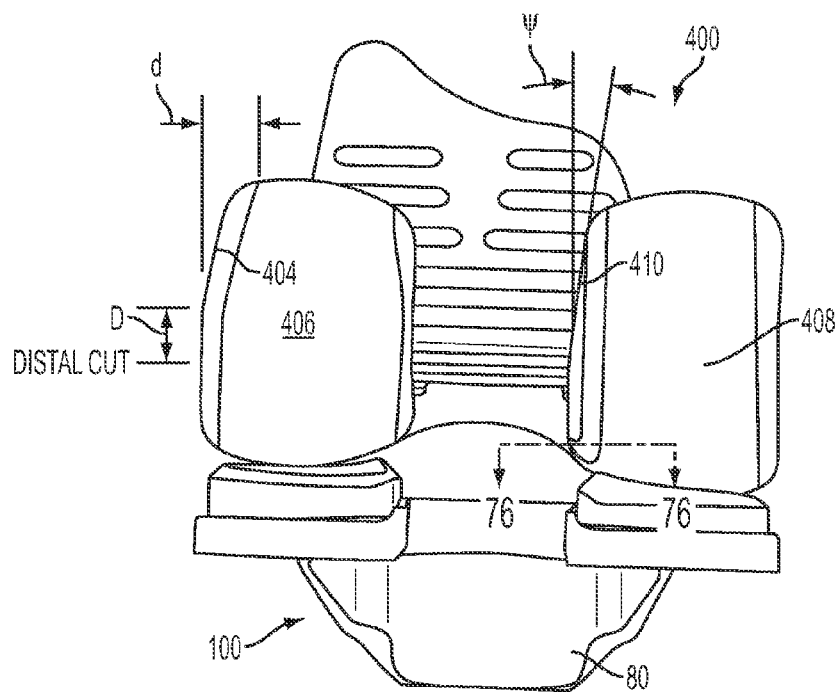
FIGS. 74 and 75 are posterior views of the bicruciate-retaining and cruciate-retaining knee prostheses of FIGS. 68 and 69, respectively, showing optional clearance chamfers provided to the femoral component.
Figure 75:
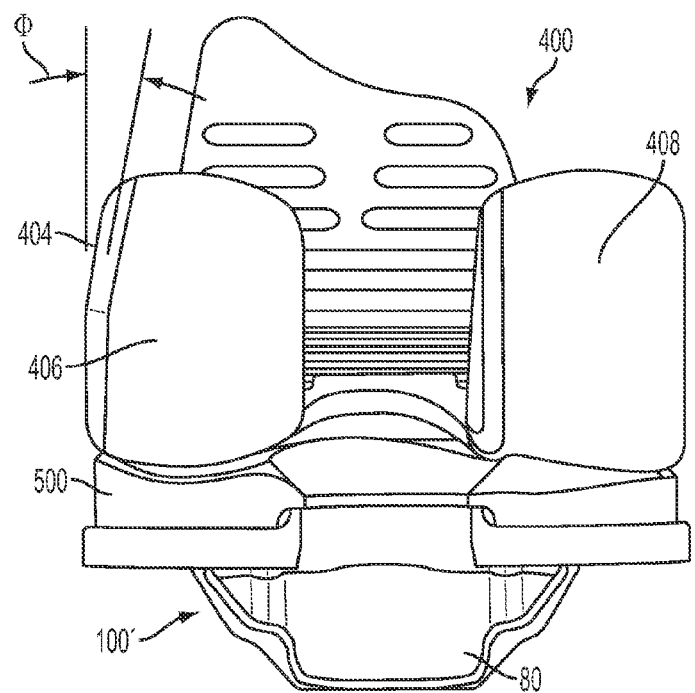
Figure 76:
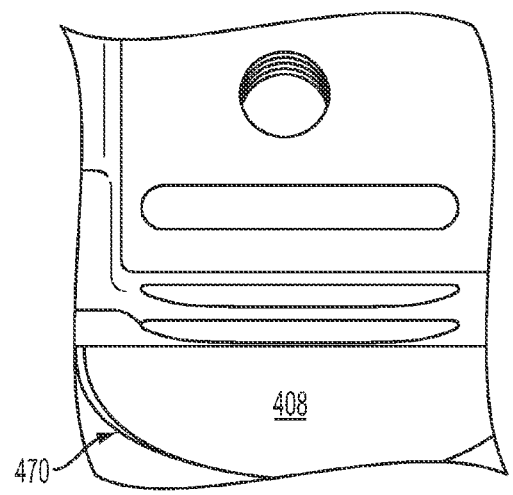
FIG. 76 is a superior view of a medial femoral condyle illustrating in partial cross-section an optional posterolateral chamfer according to some embodiments.
Figures 77, 78:
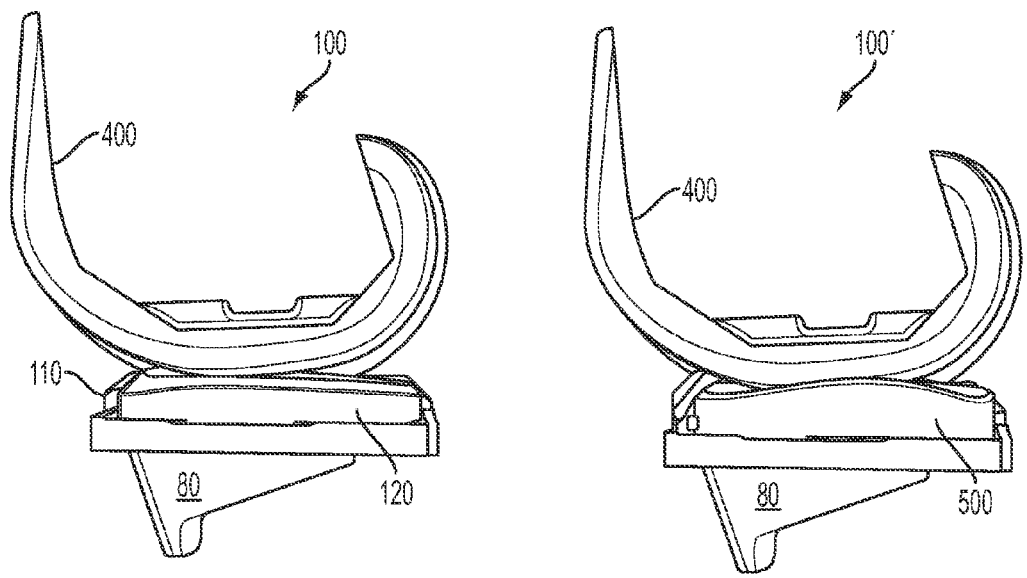
FIGS. 77 and 78 are lateral sagittal views of the bicruciate-retaining and cruciate-retaining knee prostheses of FIGS. 68 and 69, respectively.
Figure 79:
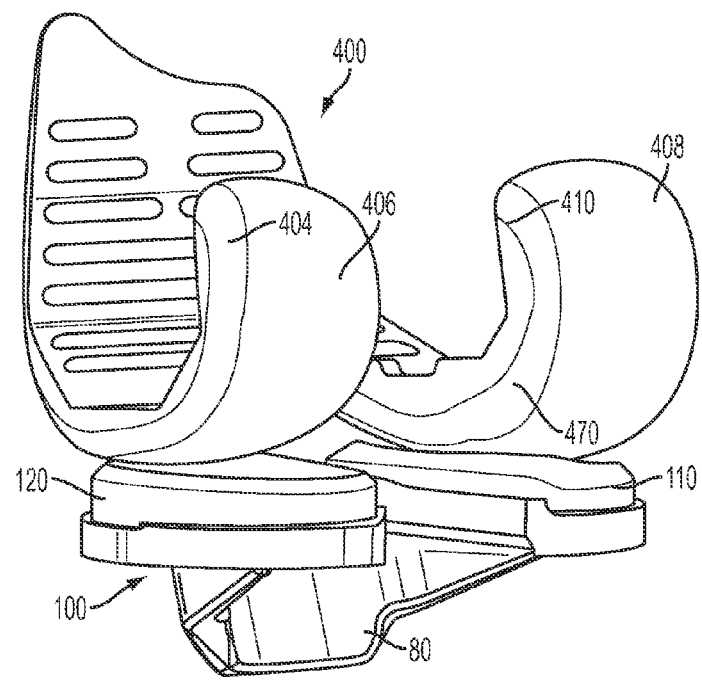
FIGS. 79 and 80 are posterolateral views of the bicruciate-retaining and cruciate-retaining knee prostheses of FIGS. 68 and 69, respectively.

Also provided are improved femoral components. For example, the femoral component 400 shown in FIGS. 67-75 includes a medial condyle 408 and a lateral posterior condyle 406 that comprises a posterolateral chamfer 404 (see, e.g., FIGS. 68-69, 72-74). As shown in FIGS. 74-75, in some embodiments, posterolateral chamfer 404 has a depth or distance d of between approximately 1 and approximately 5 mm, and more preferably between approximately 2 and approximately 4 mm, for example approximately 2.8 mm, and an angle Φ between approximately zero and approximately 25 degrees, and more preferably between approximately 5 and approximately 15 degrees, for example approximately 10 degrees, to create a clearance with the posterior lateral tissue such as the popliteal tendon in deep knee flexion. The chamfer 404 may originate a distance D from a proximal bone engaging surface configured to mate with a distal femoral bone cut, said distance D, for example, being between approximately 3 and approximately 20 mm, and more preferably between approximately 8 and approximately 15 mm, for example, approximately 11 mm. Distances d and D may increase proportionally or disproportionally with increasing femoral component 400 sizes. In some embodiments, for example, larger sizes of femoral component 400 may employ an angle Φ of approximately 10° and a distance D of approximately 11 mm, whereas smaller sizes of femoral component 400 may employ a smaller distance D of approximately 10 mm.

Similarly, medial posterior condyle 408 may comprise on its inner surface a posterolateral chamfer 410, shown in FIGS. 74, 76, 79-81, having an angle ψ between approximately 0 and approximately 10 degrees and more preferably between approximately 3 and approximately 7 degrees, for example approximately 5 degrees as shown in FIG. 74. Such a chamfer may be combined with another chamfer 470 that may be swept around an inner sagittal radius of posterior medial condyle 408 to provide additional clearance with the tibial eminence 222 and posterior cruciate ligament 320, without decreasing bone coverage. In some embodiments, the posterolateral chamfer 470 starts just posterior to patella contacting areas of the femoral component 400, and therefore, it may not sweep around intercondylar patellar contacting regions 412 of the femoral component. Rather, posterolateral chamfer 470 may be more pronounced in posterior portions of the medial femoral condyle 408. Top edges of the tibial eminence 222 may also be chamfered using a rongeur to further avoid impingement with the femoral component 400.

Figure 94:
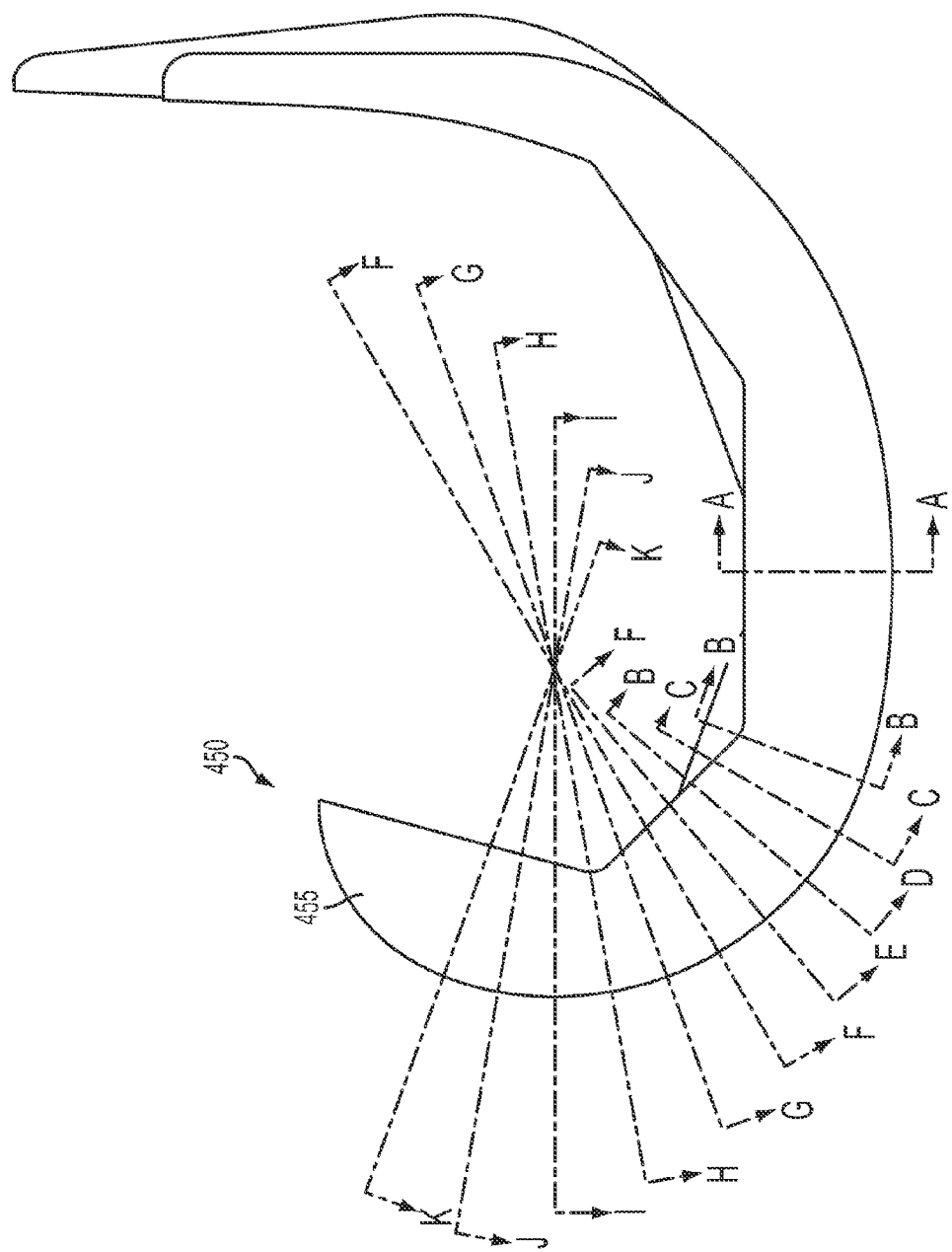
FIG. 94 is a medial sagittal view of a femoral component according to one embodiment.
Figure 95A:
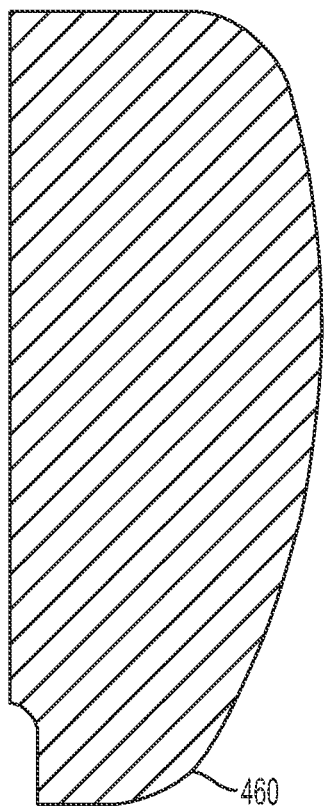
FIGS. 95*a*-95*k* are various coronal cross sectional views taken along the lines A-A through K-K, respectively, of FIG. 94.
Figure 95B:
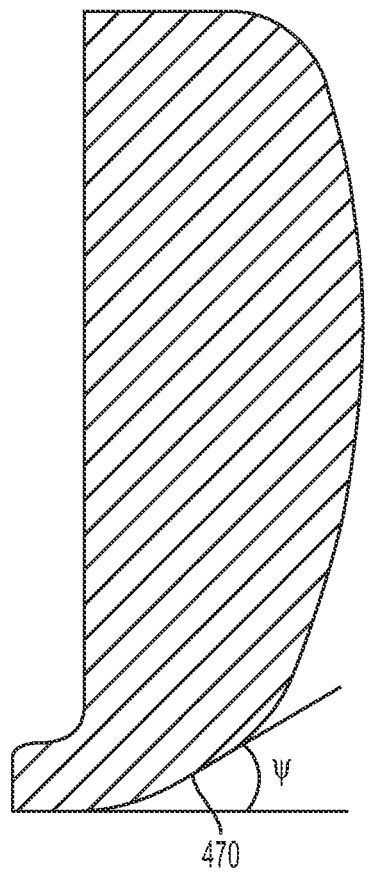
Figure 95C:
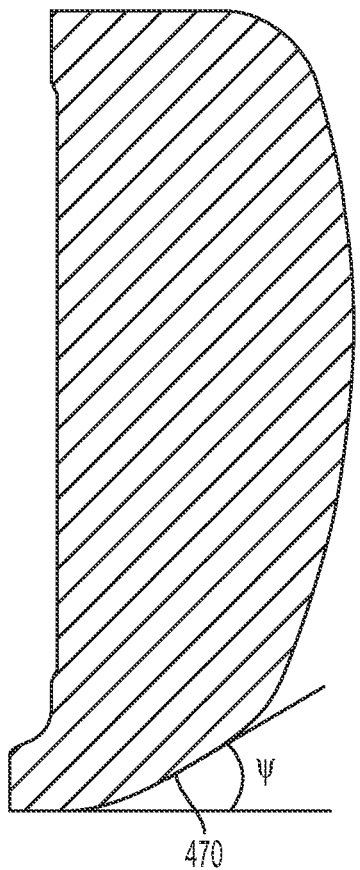
Figure 95D:
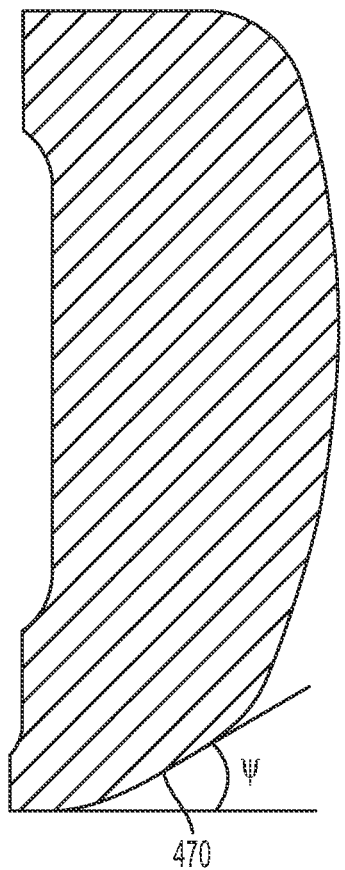
Figure 95E:
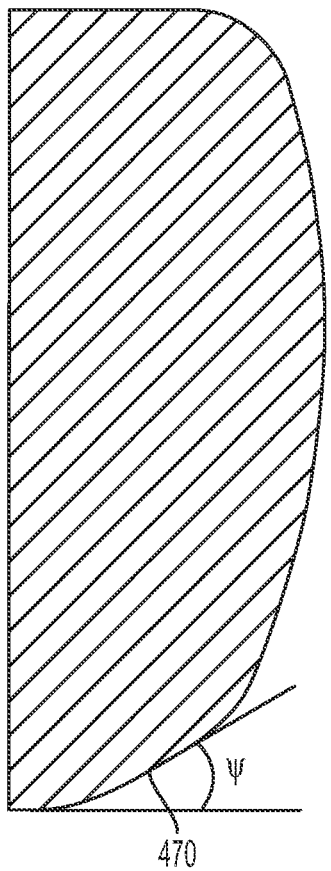
Figure 95F:
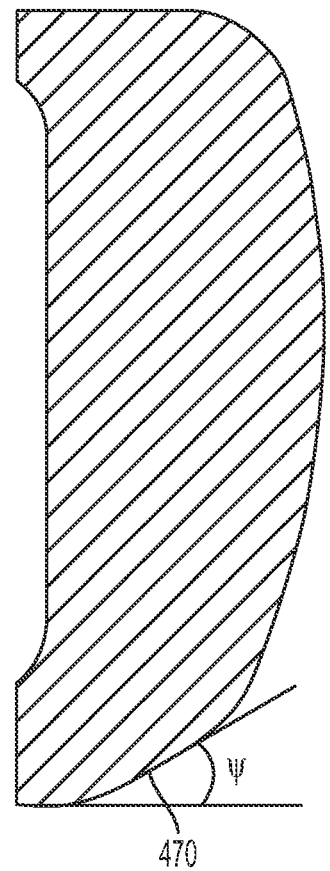
Figure 95G:
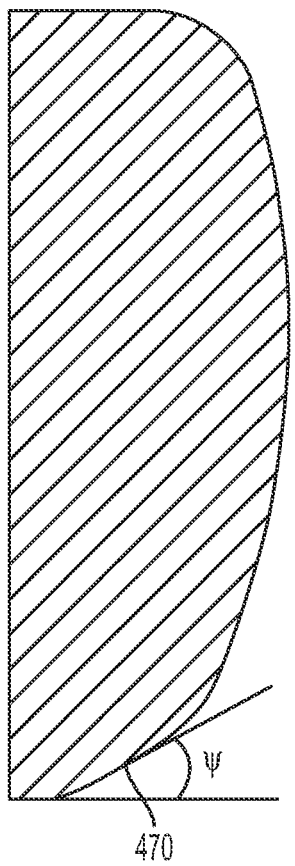
Figure 95H:
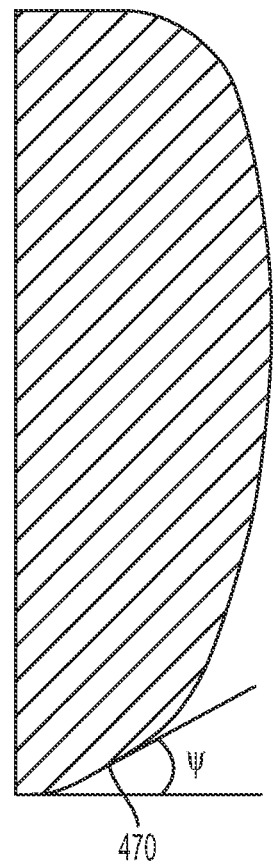
Figure 95I:
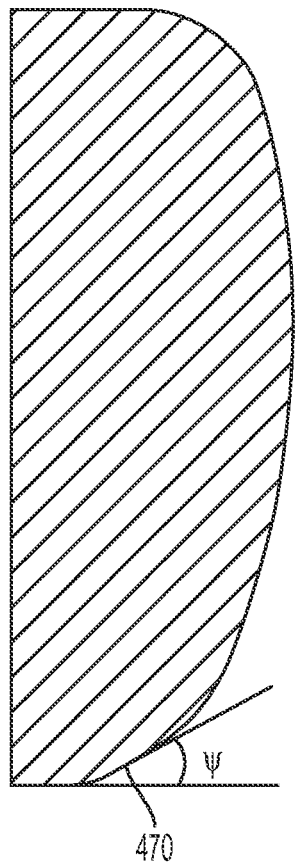
Figure 95J:
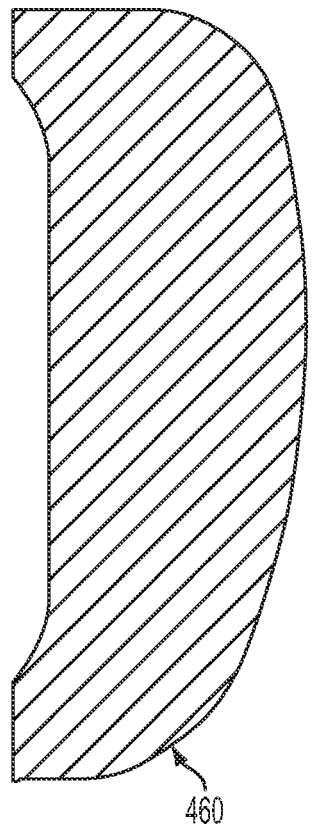
Figure 95K:
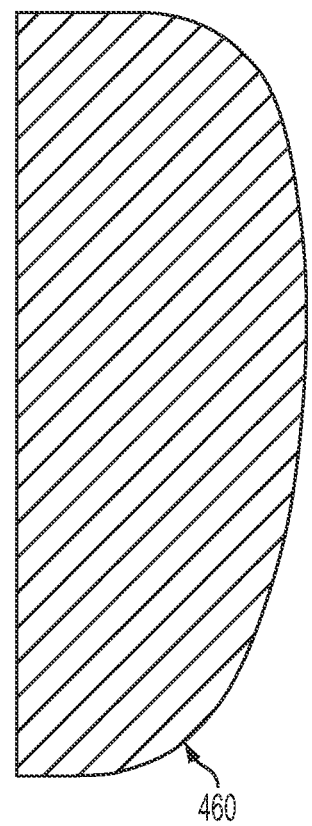

FIG. 94 is a medial sagittal view of a medial condyle 455 of a femoral component 450 according to one aspect. The medial posterior condyle 455 may comprise on its inner surface a posterolateral chamfer 470. FIGS. 95a-95k are various coronal cross sectional views taken along the lines A-A through K-K, respectively, of FIG. 94 illustrating posterolateral chamfer 470. As shown in FIGS. 95a-95k, femoral component includes a rounded edge 460 when viewed along lines A-A, J-J- and K-K, and includes a posterolateral chamfer 470 when viewed along lines B-B, C-C, D-D, E-E, F-F, G-G, H-H, I-I. The angle ψ of posterolateral chamfer 470 is between approximately 15 and approximately 40 degrees in some embodiments.

As shown in FIG. 68, the anterior flange of the femoral component 400 may comprise an anterolateral chamfer 402 on lateral and/or medial sides to reduce tension on the retinaculum tissue, which may be common with some prior art femoral designs.

Various modifications could be made to the exemplary embodiments, as described above with reference to the corresponding illustrations, without departing from the scope of the invention, and therefore, it is intended that all matter contained in the foregoing description and shown in the accompanying drawings shall be interpreted as illustrative rather than limiting. For example, the novel features of the tibial inserts disclosed may be readily applied to instrumentation such as tibial insert trials, as well as implants designed to be implanted. Thus, the breadth and scope of the invention should not be limited by any of the above-described exemplary embodiments, but should be instead defined only in accordance with any claims which may be appended hereto and their equivalents.

The invention claimed is:

1. A tibial prosthesis for at least partially replacing a proximal portion of a tibia, the tibial prosthesis comprising:
   (a) a medial baseplate portion comprising a medial inferior surface for contact with a medial resected surface on the proximal portion of the tibia;
   (b) a lateral baseplate portion comprising a lateral inferior surface for contact with a lateral resected surface on the proximal portion of the tibia;
   (c) a connection baseplate portion extending between the medial and lateral baseplate portions, the connection baseplate portion comprising a connection inferior surface; and
   (d) a keel for penetration into a cavity formed in the proximal tibia, wherein the keel extends at an inferior-posterior angle away from at least one of the medial inferior surface, the lateral inferior surface, and the connection inferior surface, the keel including an anterior keel portion, a medial keel portion extending from the medial inferior surface, and a lateral keel portion extending from the lateral inferior surface, the anterior keel portion having an overall length in a medial-lateral direction;
   wherein the tibial prosthesis defines a notch between the medial and lateral baseplate portions posterior to the connection baseplate portion, the notch having a length in the medial-lateral direction, wherein the overall length of the anterior keel portion in the medial-lateral direction is greater than the length of the notch in the medial-lateral direction; and
   wherein the anterior keel portion extends across the connection baseplate portion such that medial portions of the anterior keel portion are positioned further anteriorly than corresponding lateral portions of the anterior keel portion.

2. The tibial prosthesis of claim 1, wherein the anterior keel portion extends at the inferior-posterior angle away from the connection inferior surface.

3. The tibial prosthesis of claim 2, wherein at least a part of the anterior keel portion extends generally in the medial-lateral direction on the connection baseplate portion, wherein at least a part of the medial keel portion extends generally in an anterior-posterior direction on the medial baseplate portion, and wherein at least a part of the lateral keel portion extends generally in the anterior-posterior direction on the lateral baseplate portion.

4. The tibial prosthesis of claim 2, wherein the anterior keel portion joins the medial and lateral keel portions at areas of increased thickness.

5. The tibial prosthesis of claim 2, wherein the anterior keel portion joins the medial and lateral keel portions at areas of increased width.

6. The tibial prosthesis of claim 2, wherein the connection baseplate portion increases in thickness from anterior to posterior in an anterior-posterior direction.

7. The tibial prosthesis of claim 2, wherein the medial and lateral keel portions decrease in height as the medial and lateral keel portions extend from anterior to posterior in an anterior-posterior direction.

8. The tibial prosthesis of claim 2, wherein a posterior face of the anterior keel portion is offset from a posterior face of the connection baseplate portion.

9. The tibial prosthesis of claim 2, wherein the notch is a central notch that has a sufficient width and length to receive a portion of a tibial eminence including an anterior cruciate ligament attachment site and a posterior cruciate ligament attachment site.

10. The tibial prosthesis of claim 9, wherein the central notch comprises a medial edge and a lateral edge, wherein an angle defined by the medial edge and a base of the anterior keel portion is acute; and wherein an angle defined by the lateral edge and the base of the anterior keel portion is obtuse.

11. The tibial prosthesis of claim 1, wherein the tibial prosthesis is asymmetric about a midline extending in an anterior-posterior direction between the medial and lateral baseplate portions and the medial baseplate portion extends further anteriorly than the lateral baseplate portion.

12. The tibial prosthesis of claim 1, further comprising at least one tibial articulation surface for articulation with a femoral condylar articulation surface of a femoral component,
wherein the tibial articulation surface defines a mesial lip extending in an anterior to posterior direction along a mesial edge of the articulation surface;
wherein the mesial lip is raised by a height relative to a corresponding central portion of the articulation surface.

13. The tibial prosthesis of claim 12, wherein the femoral component comprises a medial condyle and a lateral condyle and wherein at least one of the medial condyle and the lateral condyle comprises a posterolateral chamfer.

14. The tibial prosthesis of claim 12, wherein the at least one tibial articulation surface generally slopes in an anterior-posterior direction.

15. The tibial prosthesis of claim 14, wherein the at least one tibial articulation surface comprises a medial articulation surface and a lateral articulation surface, and wherein a slope of the medial articulation surface in the anterior-posterior direction is different from a slope of the lateral articulation surface in the anterior-posterior direction.

16. The tibial prosthesis of claim 15, wherein the medial articulation surface is associated with a medial insert and the lateral articulation surface is associated with a lateral insert, wherein a thickness of the medial insert at an anterior portion of the medial insert is different than a thickness of the lateral insert at a posterior portion of the lateral insert.

17. The tibial prosthesis of claim 16, wherein the thickness of the medial insert at the anterior portion of the medial insert is greater than the thickness of the medial insert at a posterior portion of the medial insert.

18. The tibial prosthesis of claim 16, wherein a thickness of the medial insert at a posterior portion of the medial insert is different than a thickness of the lateral insert at a posterior portion of the lateral insert.

19. The tibial prosthesis of claim 16, wherein the thickness of the lateral insert at the anterior portion of the lateral insert is greater than the thickness of the lateral insert at a posterior portion of the lateral insert.

20. The tibial prosthesis of claim 14, wherein the at least one tibial articulation surface generally slopes in the medial-lateral direction.

21. The tibial prosthesis of claim 20, wherein the at least one tibial articulation surface comprises a medial articulation surface and a lateral articulation surface, and wherein a slope of the medial articulation surface in the medial-lateral direction is different from a slope of the lateral articulation surface in the medial-lateral direction.

22. The tibial prosthesis of claim 21, wherein the medial articulation surface is associated with a medial insert and the lateral articulation surface is associated with a lateral insert, wherein a thickness of the medial insert at an anterior portion of the medial insert is greater than a thickness of the lateral insert at an anterior portion of the lateral insert, and wherein the thickness of the medial insert at a posterior portion of the medial insert is different than the thickness of the lateral insert at a posterior portion of the lateral insert.

23. The tibial prosthesis of claim 16, wherein the medial insert and the lateral insert are part of a kit of inserts having varying slopes in the anterior-posterior direction.

24. The tibial prosthesis of claim 2, wherein the anterior keel portion is positioned anteriorly on the connection inferior surface to engage anterior cortical bone when implanted in a patient.

25. The tibial prosthesis of claim 14, wherein the at least one tibial articulation surface is associated with a tibial base plate.

26. The tibial prosthesis of claim 1, wherein the inferior-posterior angle is in the range of 65 to 75 degrees.

27. The tibial prosthesis of claim 1, wherein the anterior keel portion comprises an anterior fin.

28. The tibial prosthesis of claim 27, wherein the medial keel portion comprises a medial fin and the lateral keel portion comprises a lateral fin.

29. The tibial prosthesis of claim 1, wherein the lateral keel portion comprises a lateral fin and an oblique fin extending from the lateral fin; and
wherein the medial keel portion comprises a medial fin and an oblique fin extending from the medial fin.

30. A tibial prosthesis for at least partially replacing a proximal portion of a tibia, the tibial prosthesis comprising:
(a) a medial baseplate portion comprising a medial inferior surface for contact with a medial resected surface on the proximal portion of the tibia;
(b) a lateral baseplate portion comprising a lateral inferior surface for contact with a lateral resected surface on the proximal portion of the tibia;
(c) a connection baseplate portion extending between the medial and lateral baseplate portions, the connection baseplate portion comprising a connection inferior surface; and
(d) a keel for penetration into a cavity formed in the proximal tibia, wherein the keel extends at an inferior-posterior angle away from at least one of the medial inferior surface, the lateral inferior surface, and the connection inferior surface, the keel including an anterior keel portion, a medial keel portion extending from the medial inferior surface, and a lateral keel portion extending from the lateral inferior surface;
wherein the tibial prosthesis defines a notch between the medial and lateral baseplate portions posterior to the connection baseplate portion, the notch having a medial edge along the medial baseplate portion, and a lateral edge along the lateral baseplate portion;
wherein the anterior keel portion extends medially of the medial edge of the notch and extends laterally of the lateral edge of the notch; and
wherein the anterior keel portion extends across the connection baseplate portion such that medial portions of the anterior keel portion are positioned further anteriorly than corresponding lateral portions of the anterior keel portion.

31. The tibial prosthesis of claim 30, wherein the anterior keel portion extends at the inferior-posterior angle away from the connection inferior surface.

32. The tibial prosthesis of claim 31, wherein the anterior keel portion joins the medial and lateral keel portions at areas of increased thickness.

33. The tibial prosthesis of claim 32, wherein the areas of increased thickness comprise:
a connecting member at a transition from the anterior keel portion to the medial keel portion; and
a connecting member at a transition of the anterior keel portion to the lateral keel portion.

34. The tibial prosthesis of claim 31, wherein the medial and lateral keel portions decrease in height as the medial and lateral keel portions extend from anterior to posterior in an anterior-posterior direction.

35. The tibial prosthesis of claim 31, wherein the anterior keel portion extends across the connection baseplate portion such that medial portions of the anterior keel portion are positioned further anteriorly than lateral portions of the anterior keel portion.

36. The tibial prosthesis of claim 30, wherein the notch is a central notch that has a sufficient width and length to receive a portion of a tibial eminence including an anterior cruciate ligament attachment site and a posterior cruciate ligament attachment site.

37. The tibial prosthesis of claim 30, wherein the lateral keel portion comprises a lateral fin and an oblique fin extending from the lateral fin; and
wherein the medial keel portion comprises a medial fin and an oblique fin extending from the medial fin.

38. A tibial prosthesis for at least partially replacing a proximal portion of a tibia, the tibial prosthesis comprising:
(a) a medial baseplate portion comprising a medial inferior surface for contact with a medial resected surface on the proximal portion of the tibia;
(b) a lateral baseplate portion comprising a lateral inferior surface for contact with a lateral resected surface on the proximal portion of the tibia;
(c) a connection baseplate portion extending between the medial and lateral baseplate portions, the connection baseplate portion comprising a connection inferior surface; and
(d) a keel for penetration into a cavity formed in the proximal tibia, wherein the keel extends at an inferior-posterior angle away from at least one of the medial inferior surface, the lateral inferior surface, and the connection inferior surface, the keel including an anterior keel portion, a medial keel portion extending from the medial inferior surface, and a lateral keel portion extending from the lateral inferior surface;
wherein the anterior keel portion comprises an anterior-most surface of the keel and the anterior keel portion extends from the anterior-most surface to the lateral keel portion and the medial keel portion, the anterior keel portion having an overall length in a medial-lateral direction and an overall thickness in an anterior-posterior direction, the overall length being greater than the overall thickness; and
wherein the anterior keel portion extends across the connection baseplate portion such that medial portions of the anterior keel portion are positioned further anteriorly than corresponding lateral portions of the anterior keel portion.

39. The tibial prosthesis of claim 38, wherein the anterior keel portion extends at the inferior-posterior angle away from the connection inferior surface.

40. The tibial prosthesis of claim 39, wherein the anterior keel portion joins the medial and lateral keel portions at areas of increased thickness.

41. The tibial prosthesis of claim 40, wherein the areas of increased thickness comprise:
a connecting member at a transition from the anterior keel portion to the medial keel portion; and
a connecting member at a transition of the anterior keel portion to the lateral keel portion.

42. The tibial prosthesis of claim 39, wherein the medial and lateral keel portions decrease in height as the medial and lateral keel portions extend from anterior to posterior in the anterior-posterior direction.

43. The tibial prosthesis of claim 38, wherein the notch is a central notch that has a sufficient width and length to receive a portion of a tibial eminence including an anterior cruciate ligament attachment site and a posterior cruciate ligament attachment site.

44. The tibial prosthesis of claim 38, wherein the lateral keel portion comprises a lateral fin and an oblique fin extending from the lateral fin; and
wherein the medial keel portion comprises a medial fin and an oblique fin extending from the medial fin.

45. A tibial prosthesis for at least partially replacing a proximal portion of a tibia, the tibial prosthesis comprising:
(a) a medial baseplate portion comprising a medial inferior surface for contact with a medial resected surface on the proximal portion of the tibia;
(b) a lateral baseplate portion comprising a lateral inferior surface for contact with a lateral resected surface on the proximal portion of the tibia;
(c) a connection baseplate portion extending between the medial and lateral baseplate portions, the connection baseplate portion comprising a connection inferior surface; and
(d) a keel for penetration into a cavity formed in the proximal tibia, wherein the keel extends at an inferior-posterior angle away from at least one of the medial inferior surface, the lateral inferior surface, and the connection inferior surface, the keel including an anterior keel portion, a medial keel portion extending from the medial inferior surface, and a lateral keel portion extending from the lateral inferior surface, the anterior keel portion having an overall length in a medial-lateral direction;
wherein the tibial prosthesis defines a notch between the medial and lateral baseplate portions posterior to the connection baseplate portion, the notch having a length in the medial-lateral direction, wherein the overall length of the anterior keel portion in the medial-lateral direction is greater than the length of the notch in the medial-lateral direction;
wherein the anterior keel portion has an anterior surface that extends along the connection baseplate portion, the anterior surface having a medial region located medial to the notch and a lateral region located lateral to the notch, the medial region and the lateral region being in a plane parallel to the connection inferior surface, wherein the medial region of the anterior surface is positioned anterior to the lateral region of the anterior surface.

* * * * *